US012779042B2

(12) United States Patent
You et al.

(10) Patent No.: US 12,779,042 B2
(45) Date of Patent: Nov. 3, 2026

(54) ERK5 DEGRADERS AND USES THEREOF

(71) Applicant: DANA-FARBER CANCER INSTITUTE, INC., Boston, MA (US)

(72) Inventors: Inchul You, Boston, MA (US); Eric Wang, Brookline, MA (US); Nathanael S. Gray, Stanford, CA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 316 days.

(21) Appl. No.: 18/691,268

(22) PCT Filed: Sep. 19, 2022

(86) PCT No.: PCT/US2022/076655

§ 371 (c)(1),
(2) Date: Mar. 12, 2024

(87) PCT Pub. No.: WO2023/044482

PCT Pub. Date: Mar. 23, 2023

(65) Prior Publication Data

US 2024/0374737 A1 Nov. 14, 2024

Related U.S. Application Data

(60) Provisional application No. 63/246,051, filed on Sep. 20, 2021.

(51) Int. Cl.

| | |
|---|---|
| ***A61K 47/55*** | (2017.01) |
| ***A61K 31/506*** | (2006.01) |
| ***A61K 31/519*** | (2006.01) |
| ***A61K 39/395*** | (2006.01) |
| ***A61K 47/54*** | (2017.01) |

(52) U.S. Cl.

CPC ............ *A61K 47/55* (2017.08); *A61K 31/506* (2013.01); *A61K 31/519* (2013.01); *A61K 39/3955* (2013.01); *A61K 47/545* (2017.08)

(58) Field of Classification Search

CPC .... A61K 47/55; A61K 47/545; A61K 31/506; A61K 31/519; A61K 39/3955
USPC .................................................... 514/252.17
See application file for complete search history.

(56) References Cited

U.S. PATENT DOCUMENTS

| | | | |
|---|---|---|---|
| 2015/0344486 | A1 | 12/2015 | Hollick et al. |
| 2022/0378919 | A1 | 12/2022 | Gray et al. |

FOREIGN PATENT DOCUMENTS

| | | | |
|---|---|---|---|
| WO | 2008113711 | A1 | 9/2008 |
| WO | 2010080712 | A2 | 7/2010 |
| WO | 2016105518 | A1 | 6/2016 |
| WO | 2017007612 | A1 | 1/2017 |
| WO | 2018148443 | A1 | 8/2018 |
| WO | 2019170543 | A1 | 9/2019 |
| WO | 2021061894 | A1 | 4/2021 |
| WO | 2021194318 | A1 | 9/2021 |

OTHER PUBLICATIONS

Nguyen et al., "Discovery and Characterization of the Potent and Highly Selective (Piperidin-4-yl)pyrido[3,2-d]. Pyrimidine Based in Vitro Probe BAY-885 for the Kinase ERK5," Journal of Medicinal Chemistry, 2019, vol. 62, pp. 928-940.

Atilaw, et al., "Solution Conformations Shed Light on PROTAC Cell Permeability", ACS Med. Chem. Lett., 2021, vol. 12, pp. 107-114.

Hatcher, et al., "Development of Highly Potent and Selective Steroidal Inhibitors and Degraders of CDK8," ACS Med. Chem. Lett., 2018, vol. 9, pp. 540-545.

Lin, et al., "ERK5 Kinase Activity is Dispensable for Cellular Immune Response and Proliferation," PNAS, 2016, vol. 113, No. 42, pp. 11865-11870.

*Primary Examiner* — Kristin A Vajda

(74) *Attorney, Agent, or Firm* — Arent Fox Schiff LLP; Daniel W. J. Clarke D.; Shawn P. Foley

(57) ABSTRACT

Described are the bifunctional compounds, compositions and methods of treating a disease or disorder characterized by aberrant extracellular-signal-regulated kinase 5 (ERK5) activity.

26 Claims, 7 Drawing Sheets

ERK5 DEGRADERS AND USES THEREOF

RELATED APPLICATIONS

This application is a national stage application, filed under 35 U.S.C. § 371, of International Application No. PCT/US2022/076655, filed Sep. 19, 2022, which claims the benefit of priority under 35 U.S.C. § 119 (e) to U.S. Provisional Application No. 63/246,051, filed Sep. 20, 2021, which is incorporated herein by reference in its entirety.

GOVERNMENT LICENSE RIGHTS

This invention was made with government support under grant number R01 CA218278-02 awarded by the National Institutes of Health (NIH). The government has certain rights in the invention.

BACKGROUND OF THE DISCLOSURE

Extracellular signal-regulated kinase 5 (ERK5), a recently discovered mitogen-activated protein (MAP) kinase family member, is activated by the upstream kinase mitogen/extracellular signal regulated kinase kinase-5 (MEK5) in response to growth factors and stress stimulation. ERK5 is a key integrator of cellular signal transduction. It has been shown to play a crucial role in various cellular processes such as proliferation, differentiation, apoptosis and cell survival. It has been reported that ERK5 silencing/inhibition decreases the proliferation and increases cell death in different tumor models (Yang et al., Cancer Cell 18:258-267 (2010); Rovida et al., Gut 64:1454-1465 (2015)). Several models have also demonstrated that knockdown of ERK5 suppresses cytokine release upon cellular stimulation (Wilhelmsen et al., J. Biol. Chem. 287:26478-26494 (2012); Wilhelmsen et al., Sci. Signal. 8:ra86 (2015)). Multiple reports have corroborated the effects of ERK5 knockdown and pharmacological inhibition in controlling inflammation and tumor growth (see, e.g., Lin et al., PNAS 113:11865-11870 (2016)). These studies highlight the potential of ERK5 as a therapeutic target in cancer and inflammatory diseases.

SUMMARY OF THE DISCLOSURE

A first aspect of the present disclosure is directed to a bifunctional compound (also referred to herein as a "degrader" or PROTAC), or a pharmaceutically acceptable salt or stereoisomer thereof, having a structure represented by formula (I):

(I)

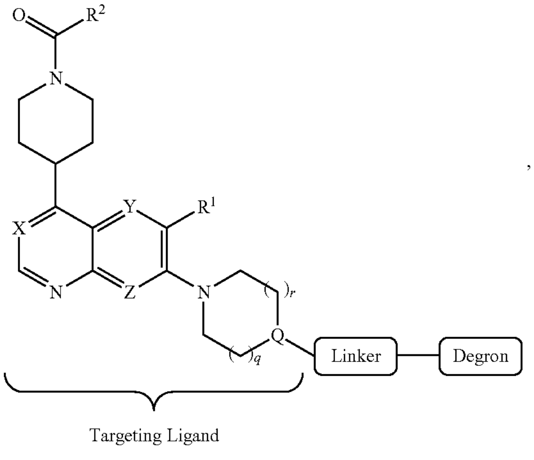

, wherein X is CH, $CR^3$, or N; Y is CH, $CR^3$, or N; Z is CH, $CR^3$, or N; Q is CH or N; $R^1$ is H, $C_1$-$C_6$ alkyl, or $C_1$-$C_6$ alkoxy; $R^2$ is a phenyl or pyridyl ring which is optionally substituted once or twice identically or differently with a substituent selected from halogen, OH, CN, $C_1$-$C_6$ alkyl, $C_1$-$C_6$ alkoxy, $C_1$-$C_6$ haloalkoxy, $C_1$-$C_6$ alkyl which is optionally substituted with a $C_1$-$C_6$ alkoxy- or $C_1$-$C_6$ haloalkoxy-substituent, $C_2$-$C_6$-alkenyl, $C_2$-$C_6$-alkynyl, $C_3$-$C_8$-cycloalkyl, —C(=O)$NR^4R^5$, —$NH_2$, —NH—C(=O)—$C_1$-$C_6$-alkyl, $C_1$-$C_6$-alkoxy which is optionally substituted with a hydroxyl or $C_1$-$C_6$-alkyl substituent, —O—$C_3$-$C_8$-cycloalkyl, —O-(4- to 7-membered heterocycloalkyl), $C_1$-$C_6$-alkylthio, $C_1$-$C_6$-haloalkylthio, or —S(=O)$_2$—$C_1$-$C_6$-alkyl group; $R^3$ is H, or $C_1$-$C_6$ alkyl; $R^4$ and $R^5$ independently represent hydrogen, a $C_1$-$C_6$-alkyl or phenyl group; each occurrence of q and r is independently 0 or 1; the targeting ligand binds ERK5; the degron ("Degron") represents a moiety that binds an E3 ubiquitin ligase; and the linker ("Linker") provides a covalent attachment between the targeting ligand and the degron.

Another aspect of the present disclosure is directed to a pharmaceutical composition that includes a therapeutically effective amount of a bifunctional compound of formula (I) or a pharmaceutically acceptable salt or stereoisomer thereof, and a pharmaceutically acceptable carrier.

A further aspect of the present disclosure is directed to a method of treating a disease or disorder that is characterized or mediated by aberrant ERK5 activity that entails administering to a subject in need thereof a therapeutically effective amount of a bifunctional compound of formula (I) or a pharmaceutically acceptable salt or stereoisomer thereof.

In some embodiments, the disease or disorder is a cancer. In some embodiments, the cancer is leukemia, breast cancer, multiple myeloma, colon cancer, renal cancer, mesothelioma, pancreatic cancer, liver cancer, melanoma, or lung cancer.

In some embodiments, the disease or disorder is an inflammatory disease. In some embodiments, the inflammatory disease is rheumatoid arthritis, coeliac disease scleroderma, Sjogren's syndrome, lupus, vasculitis, myositis, gout, ankylosing spondylitis, or inflammatory bowel disease.

A further aspect of the present disclosure is directed to co-administering a therapeutically effective amount of an immunotherapy and/or chemotherapy. In some embodiments, the immunotherapy is a checkpoint inhibitor, a cell-cycle inhibitor, or a targeted therapy. In some embodiments, the checkpoint inhibitor is anti-PD-1 or anti-PD-L1. In some embodiments, the cell-cycle inhibitor is palbociclib, ribociclib, or abemaciclib. In some embodiments, the targeted therapy is a kinase inhibitor.

A further aspect of the present disclosure is directed to methods of reducing the levels of ERK5 in a cell, either in vitro or in vivo, comprising contacting the cell with an effective amount of the bifunctional compound or pharmaceutically acceptable salt or stereoisomer thereof of the present disclosure.

While degraders can show remarkable efficacy and sustained target depletion, some proteins, including ERK5, have proven recalcitrant to this approach. As demonstrated in the working examples, bifunctional compounds of the present disclosure are potent and selective degraders of ERK5.

DETAILED DESCRIPTION OF THE DISCLOSURE

Figure 1A:
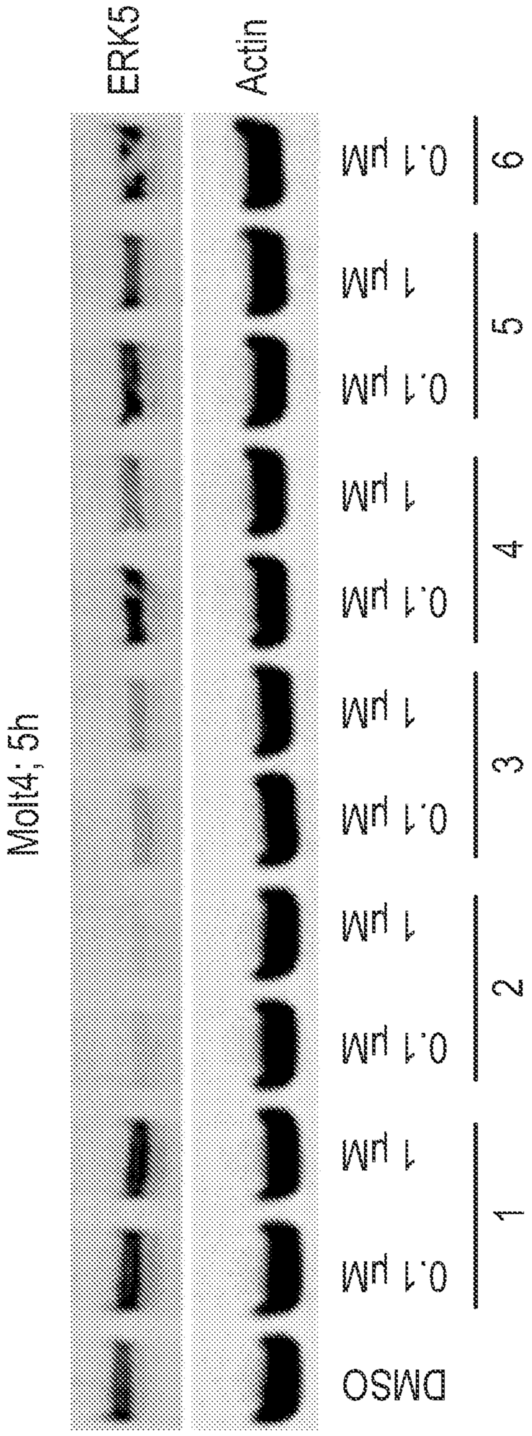
FIG. 1A is an immunoblot showing ERK5 degradation for compounds 1-6 at the indicated concentrations (0.1 μM and/or 1 μM) in Molt4 cells after 5 hours.
Figure 1B:
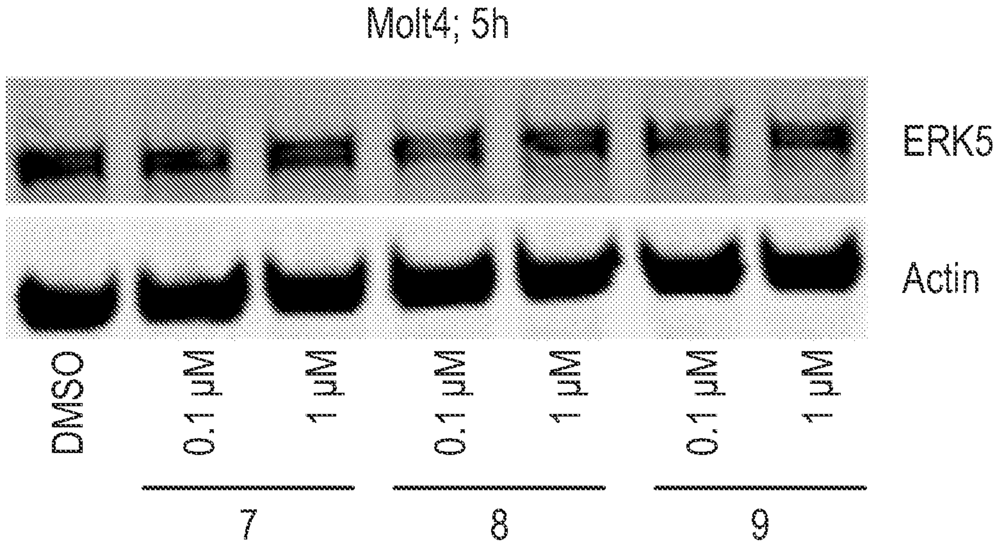
FIG. 1B is an immunoblot showing ERK5 degradation for compounds 7-9 at 0.1 μM and 1 μM in Molt4 cells after 5 hours.
Figure 1C:
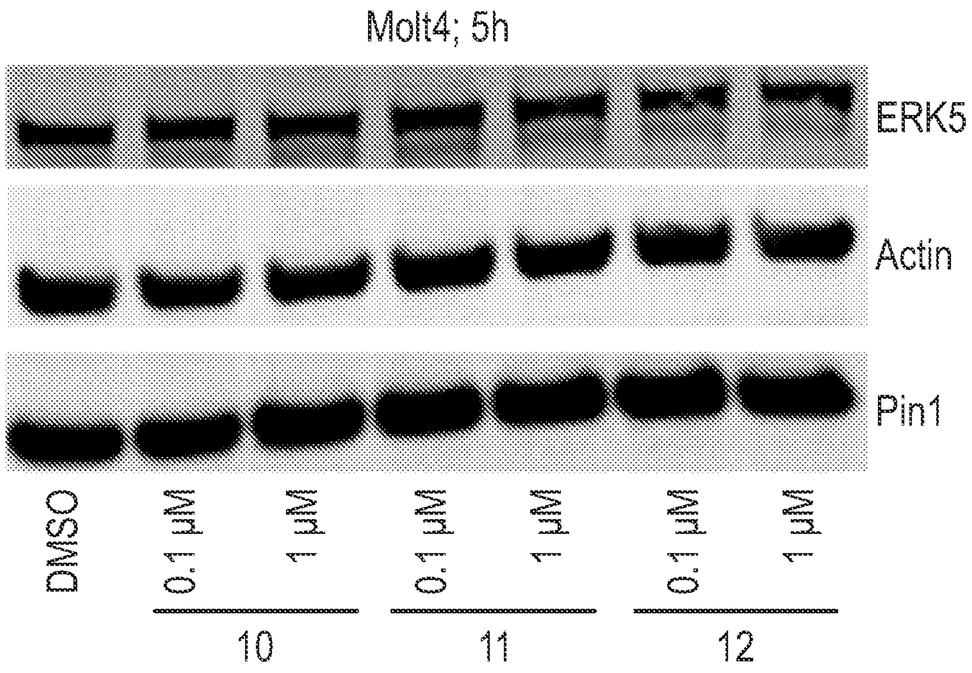
FIG. 1C is an immunoblot showing ERK5 degradation for compounds 10-12 at 0.1 μM and 1 μM in Molt4 cells after 5 hours.

It has been reported that ERK5 may play a critical role in regulating immune cell functions, specifically in the inflammatory response and in macrophage phenotype and polarization. While promising anti-inflammation and anti-cancer phenotypes have been reported due to knockdown or knockout of ERK5, selective ATP-competitive inhibitors of ERK5 were unable to recapitulate these phenotypes. This suggests that there are noncatalytic functions of ERK5 which are not affected by ATP-competitive ERK5 kinase inhibitors, but which could be targeted via degradation of the ERK5 protein. Therefore, it is envisioned that ERK5 degraders have anti-inflammation and anti-cancer activities in contrast to phenotypically quiet ERK5 inhibitors. Herein is demonstrated that degradation of ERK5 is possible through reprogramming the substrate specificity of E3 ligase complexes such as Von Hippel-Lindau tumor suppressor (VHL) or CRL4(CRBN) to target ERK5 for ubiquitination and subsequent proteasomal degradation.

Unless defined otherwise, all technical and scientific terms used herein have the same meaning as is commonly understood by one of skill in the art to which the subject matter herein belongs. As used in the specification and the appended claims, unless specified to the contrary, the following terms have the meaning indicated in order to facilitate the understanding of the present disclosure.

As used in the description and the appended claims, the singular forms "a", "an", and "the" include plural referents unless the context clearly dictates otherwise. Thus, for example, reference to "a composition" includes mixtures of two or more such compositions, reference to "an inhibitor" includes mixtures of two or more such inhibitors, and the like.

Unless stated otherwise, the term "about" means within 10% (e.g., within 5%, 2% or 1%) of the particular value modified by the term "about."

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed disclosure.

With respect to bifunctional compounds of the present disclosure, and to the extent the following terms are used herein to further describe them, the following definitions apply.

As used herein, the term "alkyl" refers to a saturated linear or branched-chain monovalent hydrocarbon radical. To the extent not defined otherwise for any particular group in the compounds of formula (I), in one embodiment, the alkyl radical is a $C_1$-$C_{18}$ group. In other embodiments, the alkyl radical is a $C_0$-$C_6$, $C_0$-$C_5$, $C_0$-$C_3$, $C_1$-$C_{12}$, $C_1$-$C_8$, $C_1$-$C_6$, $C_1$-$C_5$, $C_1$-$C_4$ or $C_1$-$C_3$ group (wherein $C_0$ alkyl refers to a bond). Examples of alkyl groups include methyl, ethyl, 1-propyl, 2-propyl, i-propyl, 1-butyl, 2-methyl-1-propyl, 2-butyl, 2-methyl-2-propyl, 1-pentyl, n-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, heptyl, octyl, nonyl, decyl, undecyl and dodecyl. In some embodiments, an alkyl group is a $C_1$-$C_3$ alkyl group. In some embodiments, an alkyl group is a $C_3$-$C_5$ branched-chain alkyl group.

As used herein, the term "alkylene" refers to a straight or branched divalent hydrocarbon chain linking the rest of the molecule to a radical group, consisting solely of carbon and hydrogen, containing no unsaturation and having from one to 12 carbon atoms, for example, methylene, ethylene, propylene, n-butylene, and the like. In some embodiments, the linker comprises an alkylene chain which may be interrupted by, and/or terminate (at either or both termini) in at least one other group. In some embodiments, the alkylene chain may be attached to the rest of the molecule through a single bond and to the radical group through a single bond.

As used herein, the term "alkenyl" refers to a linear or branched-chain monovalent hydrocarbon radical with at least one carbon-carbon double bond. To the extent not defined otherwise for any particular group in the compounds of formula (I), an alkenyl includes radicals having "cis" and "trans" orientations, or alternatively, "E" and "Z" orientations. In one example, the alkenyl radical is a $C_2$-$C_{18}$ group. In other embodiments, the alkenyl radical is a $C_2$-$C_{12}$, $C_2$-$C_{10}$, $C_2$-$C_8$, $C_2$-$C_6$ or $C_2$-$C_3$ group. Examples include ethenyl or vinyl, prop-1-enyl, prop-2-enyl, 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl and hexa-1,3-dienyl.

The terms "alkoxyl" or "alkoxy" as used herein refer to an alkyl group, as defined above, having an oxygen radical attached thereto. Representative alkoxyl groups include methoxy, ethoxy, propyloxy, tert-butoxy and the like. An "ether" is two hydrocarbyl groups covalently linked by an oxygen. Accordingly, the substituent of an alkyl that renders that alkyl an ether is or resembles an alkoxyl, such as can be represented by one of —O-alkyl, —O-alkenyl, and —O-alkynyl.

The term "$C_1$-$C_6$ haloalkoxy" means a linear or branched, saturated, monovalent $C_1$-$C_6$-alkoxy group, as defined supra, in which one or more of the hydrogen atoms is replaced, identically or differently, with a halogen atom. Particularly, said halogen atom is a fluorine atom. Said $C_1$-$C_6$-haloalkoxy group is, for example, fluoromethoxy, difluoromethoxy, trifluoromethoxy, 2,2,2-trifluoroethoxy or pentafluoroethoxy.

As used herein, the term "alkoxylene" refers to a saturated monovalent aliphatic radicals of the general formula (—O—$C_nH_{2n}$—) where n represents an integer (e.g., 1, 2, 3, 4, 5, 6, or 7) and is inclusive of both straight-chain and branched-chain radicals. The alkoxylene chain may be attached to the rest of the molecule through a single bond and to the radical group through a single bond. In some embodiments, the alkoxylene group contains one to 3 carbon atoms (—O—$C_1$-$C_3$ alkoxylene). In other embodiments, an alkoxylene group contains one to 5 carbon atoms (—O—$C_1$-$C_5$ alkoxylene).

As used herein, the term "cyclic group" broadly refers to any group that used alone or as part of a larger moiety, contains a saturated, partially saturated or aromatic ring system e.g., carbocyclic (cycloalkyl, cycloalkenyl), heterocyclic (heterocycloalkyl, heterocycloalkenyl), aryl and heteroaryl groups. To the extent not defined otherwise for any particular group in the compounds of formula (I), cyclic groups may have one or more (e.g., fused) ring systems. Thus, for example, a cyclic group can contain one or more carbocyclic, heterocyclic, aryl or heteroaryl groups.

As used herein, the term "carbocyclic" (also "carbocyclyl") refers to a group that used alone or as part of a larger moiety, contains a saturated, partially unsaturated, or aromatic ring system having 3 to 20 carbon atoms, that is alone or part of a larger moiety (e.g., an alkcarbocyclic group). To the extent not defined otherwise for any particular group in the compounds of formula (I), the term carbocyclyl includes mono-, bi-, tri-, fused, bridged, and spiro-ring systems, and combinations thereof. In one embodiment, carbocyclyl includes 3 to 15 carbon atoms ($C_3$-$C_{15}$). In one embodiment, carbocyclyl includes 3 to 12 carbon atoms ($C_3$-$C_{12}$). In another embodiment, carbocyclyl includes $C_3$-$C_8$, $C_3$-$C_{10}$ or $C_5$-$C_{10}$. In another embodiment, carbocyclyl, as a monocycle, includes $C_3$-$C_8$, $C_3$-$C_6$ or $C_5$-$C_6$. In some embodiments, carbocyclyl, as a bicycle, includes $C_7$-$C_{12}$. In another embodiment, carbocyclyl, as a spiro system, includes $C_5$-$C_{12}$. Representative examples of monocyclic carbocyclyls include cyclopropyl, cyclobutyl, cyclopentyl, 1-cyclopent-1-enyl, 1-cyclopent-2-enyl, 1-cyclopent-3-enyl, cyclohexyl, perdeuteriocyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, phenyl, and cyclododecyl; bicyclic carbocyclyls having 7 to 12 ring atoms include [4,3], [4,4], [4,5], [5,5], [5,6] or [6,6] ring systems, such as for example bicyclo[2.2.1]heptane, bicyclo[2.2.2]octane, naphthalene, and bicyclo[3.2.2]nonane. Representative examples of spiro carbocyclyls include spiro[2.2]pentane, spiro[2.3]hexane, spiro[2.4]heptane, spiro[2.5]octane and spiro[4.5]decane. The term carbocyclyl includes aryl ring systems as defined herein. The term carbocycyl also includes cycloalkyl rings (e.g., saturated or partially unsaturated mono-, bi-, or spiro-carbocycles). The term carbocyclic group also includes a carbocyclic ring fused to one or more (e.g., 1, 2 or 3) different cyclic groups (e.g., aryl or heterocyclic rings), where the radical or point of attachment is on the carbocyclic ring.

As used herein, the term "heterocyclyl" refers to a "carbocyclyl" that used alone or as part of a larger moiety, contains a saturated, partially unsaturated or aromatic ring system, wherein one or more (e.g., 1, 2, 3, or 4) carbon atoms have been replaced with a heteroatom (e.g., O, N, N(O), S, S(O), or $S(O)_2$). The term heterocyclyl includes mono-, bi-, tri-, fused, bridged, and spiro ring systems, and combinations thereof. In some embodiments, a heterocyclyl refers to a 3 to 15 membered heterocyclyl ring system. In some embodiments, a heterocyclyl refers to a 3 to 12 membered heterocyclyl ring system. In some embodiments, a heterocyclyl refers to a saturated ring system, such as a 3 to 12 membered saturated heterocyclyl ring system. In some embodiments, a heterocyclyl refers to a heteroaryl ring system, such as a 5 to 14 membered heteroaryl ring system. The term heterocyclyl also includes $C_3$-$C_8$ heterocycloalkyl, which is a saturated or partially unsaturated mono-, bi-, or spiro-ring system containing 3-8 carbons and one or more (1, 2, 3 or 4) heteroatoms.

In some embodiments, a heterocyclyl group includes 3-12 ring atoms and includes monocycles, bicycles, tricycles and spiro ring systems, wherein the ring atoms are carbon, and one to 5 ring atoms is a heteroatom such as nitrogen, sulfur or oxygen. In some embodiments, heterocyclyl includes 3- to 7-membered monocycles having one or more heteroatoms selected from nitrogen, sulfur or oxygen. In some embodiments, heterocyclyl includes 4- to 6-membered monocycles having one or more heteroatoms selected from nitrogen, sulfur or oxygen. In some embodiments, heterocyclyl includes 3-membered monocycles. In some embodiments, heterocyclyl includes 4-membered monocycles. In some embodiments, heterocyclyl includes 5-6 membered monocycles. In some embodiments, the heterocyclyl group includes 0 to 3 double bonds. In any of the foregoing embodiments, heterocyclyl includes 1, 2, 3 or 4 heteroatoms. Any nitrogen or sulfur heteroatom may optionally be oxidized (e.g., NO, SO, $SO_2$), and any nitrogen heteroatom may optionally be quaternized (e.g., $[NR_4]^+Cl^-$, $[NR_4]^+OH^-$). Representative examples of heterocyclyls include oxiranyl, aziridinyl, thiiranyl, azetidinyl, oxetanyl, thietanyl, 1,2-dithietanyl, 1,3-dithietanyl, pyrrolidinyl, dihydro-1H-pyrrolyl, dihydrofuranyl, tetrahydropyranyl, dihydrothienyl, tetrahydrothienyl, imidazolidinyl, piperidinyl, piperazinyl, morpholinyl, thiomorpholinyl, 1,1-dioxo-thiomorpholinyl, dihydropyranyl, tetrahydropyranyl, hexahydrothiopyranyl, hexahydropyrimidinyl, oxazinanyl, thiazinanyl, thioxanyl, homopiperazinyl, homopiperidinyl, azepanyl, oxepanyl, thiepanyl, oxazepinyl, oxazepanyl, diazepanyl, 1,4-diazepanyl, diazepinyl, thiazepinyl, thiazepanyl, tetrahydrothiopyranyl, oxazolidinyl, thiazolidinyl, isothiazolidinyl, 1,1-dioxoisothiazolidinonyl, oxazolidinonyl, imidazolidinonyl, 4,5,6,7-tetrahydro[2H]indazolyl, tetrahydrobenzoimidazolyl, 4,5,6,7-tetrahydrobenzo[d]imidazolyl, 1,6-dihydroimidazol[4,5-d]pyrrolo[2,3-b]pyridinyl, thiazinyl, thiophenyl, oxazinyl, thiadiazinyl, oxadiazinyl, dithiazinyl, dioxazinyl, oxathiazinyl, thiatriazinyl, oxatriazinyl, dithiadiazinyl, imidazolinyl, dihydropyrimidyl, tetrahydropyrimidyl, 1-pyrrolinyl, 2-pyrrolinyl, 3-pyrrolinyl, indolinyl, thiapyranyl, 2H-pyranyl, 4H-pyranyl, dioxanyl, 1,3-dioxolanyl, pyrazolinyl, pyrazolidinyl, dithianyl, dithiolanyl, pyrimidinonyl, pyrimidindionyl, pyrimidin-2,4-dionyl, piperazinonyl, piperazindionyl, pyrazolidinylimidazolinyl, 3-azabicyclo[3.1.0]hexanyl, 3,6-diazabicyclo[3.1.1]heptanyl, 6-azabicyclo[3.1.1]heptanyl, 3-azabicyclo[3.1.1]heptanyl, 3-azabicyclo[4.1.0]heptanyl, azabicyclo[2.2.2]hexanyl, 2-azabicyclo[3.2.1]octanyl, 8-azabicyclo[3.2.1]octanyl, 2-azabicyclo[2.2.2]octanyl, 8-azabicyclo[2.2.2]octanyl, 7-oxabicyclo[2.2.1]heptane, azaspiro[3.5]nonanyl, azaspiro[2.5]octanyl, azaspiro[4.5]decanyl, 1-azaspiro[4.5]decan-2-only, azaspiro[5.5]undecanyl, tetrahydroindolyl, octahydroindolyl, tetrahydroisoindolyl, tetrahydroindazolyl, 1,1-dioxohexahydrothiopyranyl.

Examples of 5-membered heterocyclyls containing a sulfur or oxygen atom and one to three nitrogen atoms are thiazolyl, including thiazol-2-yl and thiazol-2-yl N-oxide, thiadiazolyl, including 1,3,4-thiadiazol-5-yl and 1,2,4-thiadiazol-5-yl, oxazolyl, for example oxazol-2-yl, and oxadiazolyl, such as 1,3,4-oxadiazol-5-yl, and 1,2,4-oxadiazol-5-yl. Example 5-membered ring heterocyclyls containing 2 to 4 nitrogen atoms include imidazolyl, such as imidazol-2-yl; triazolyl, such as 1,3,4-triazol-5-yl; 1,2,3-triazol-5-yl, 1,2,4-triazol-5-yl, and tetrazolyl, such as 1H-tetrazol-5-yl. Representative examples of benzo-fused 5-membered heterocyclyls are benzoxazol-2-yl, benzthiazol-2-yl and benzimidazol-2-yl. Example 6-membered heterocyclyls contain one to three nitrogen atoms and optionally a sulfur or oxygen atom, for example pyridyl, such as pyrid-2-yl, pyrid-3-yl, and pyrid-4-yl; pyrimidyl, such as pyrimid-2-yl and pyrimid-4-yl; triazinyl, such as 1,3,4-triazin-2-yl and 1,3,5-triazin-4-yl; pyridazinyl, in particular pyridazin-3-yl, and pyrazinyl.

Thus, the term heterocyclic embraces N-heterocyclyl groups which as used herein refer to a heterocyclyl group containing at least one nitrogen and where the point of attachment of the heterocyclyl group to the rest of the molecule is through a nitrogen atom in the heterocyclyl group. Representative examples of N-heterocyclyl groups include 1-morpholinyl, 1-piperidinyl, 1-piperazinyl, 1-pyrrolidinyl, pyrazolidinyl, imidazolinyl and imidazolidinyl. The term heterocyclic also embraces C-heterocyclyl groups which as used herein refer to a heterocyclyl group containing at least one heteroatom and where the point of attachment of the heterocyclyl group to the rest of the molecule is through a carbon atom in the heterocyclyl group. Representative examples of C-heterocyclyl radicals include 2-morpholinyl, 2- or 3- or 4-piperidinyl, 2-piperazinyl, and 2- or 3-pyrrolidinyl. The term heterocyclic also embraces heterocyclylalkyl groups which as disclosed above refer to a group of the formula —$R^c$-heterocyclyl where $R^c$ is an alkylene chain. The term heterocyclic also embraces heterocyclylalkoxy groups which as used herein refer to a radical bonded through an oxygen atom of the formula —O—$R^c$-heterocyclyl where $R^c$ is an alkylene chain.

As used herein, the term "aryl" used alone or as part of a larger moiety (e.g., "aralkyl", wherein the terminal carbon atom on the alkyl group is the point of attachment, e.g., a benzyl group), "aralkoxy" wherein the oxygen atom is the point of attachment, or "aroxyalkyl" wherein the point of attachment is on the aryl group) refers to a group that includes monocyclic, bicyclic or tricyclic, carbon ring system, that includes fused rings, wherein at least one ring in the system is aromatic. To the extent not defined otherwise for any particular group in the compounds of formula (I), in some embodiments, the aralkoxy group is a benzoxy group. The term "aryl" may be used interchangeably with the term "aryl ring". In one embodiment, aryl includes groups having 6-18 carbon atoms. In another embodiment, aryl includes groups having 6-10 carbon atoms. Examples of aryl groups include phenyl, naphthyl, anthracyl, biphenyl, phenanthrenyl, naphthacenyl, 1,2,3,4-tetrahydronaphthalenyl, 1H-indenyl, 2,3-dihydro-1H-indenyl, naphthyridinyl, and the like, which may be substituted or independently substituted by one or more substituents described herein. A particular aryl is phenyl. In some embodiments, an aryl group includes an aryl ring fused to one or more (e.g., 1, 2 or 3) different cyclic groups (e.g., carbocyclic rings or heterocyclic rings), where the radical or point of attachment is on the aryl ring.

Thus, the term aryl embraces aralkyl groups (e.g., benzyl) which as disclosed above refer to a group of the formula —$R^c$-aryl where $R^c$ is an alkylene chain such as methylene or ethylene. In some embodiments, the aralkyl group is an optionally substituted benzyl group. The term aryl also embraces aralkoxy groups which as used herein refer to a group bonded through an oxygen atom of the formula —O—$R^c$-aryl where $R^c$ is an alkylene chain such as methylene or ethylene.

As used herein, the term "heteroaryl" used alone or as part of a larger moiety (e.g., "heteroarylalkyl" (also "heteroaralkyl"), or "heteroarylalkoxy" (also "heteroaralkoxy"), refers to a monocyclic, bicyclic or tricyclic ring system having 5 to 14 ring atoms, wherein at least one ring is aromatic and contains at least one heteroatom. In one embodiment, heteroaryl includes 5-6 membered monocyclic aromatic groups where one or more ring atoms is nitrogen, sulfur or oxygen that is independently optionally substituted. Representative examples of heteroaryl groups include thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, imidazopyridyl, pyrazinyl, pyridazinyl, triazinyl, tetrazinyl, tetrazolo[1,5-b]pyridazinyl, purinyl, deazapurinyl, benzoxazolyl, benzofuryl, benzothiazolyl, benzothiadiazolyl, benzotriazolyl, benzoimidazolyl, indolyl, 1,3-thiazol-2-yl, 1,3,4-triazol-5-yl, 1,3-oxazol-2-yl, 1,3,4-oxadiazol-5-yl, 1,2,4-oxadiazol-5-yl, 1,3,4-thiadiazol-5-yl, 1H-tetrazol-5-yl, 1,2,3-triazol-5-yl, and pyrid-2-yl N-oxide. The term "heteroaryl" also includes groups in which a heteroaryl is fused to one or more cyclic (e.g., carbocyclyl, or heterocyclyl) rings, where the radical or point of attachment is on the heteroaryl ring. Nonlimiting examples include indolyl, indolizinyl, isoindolyl, benzothienyl, benzothiophenyl, methylenedioxyphenyl, benzofuranyl, dibenzofuranyl, indazolyl, benzimidazolyl, benzodioxazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl and pyrido[2,3-b]-1,4-oxazin-3(4H)-one. A heteroaryl group may be mono-, bi- or tri-cyclic. In some embodiments, a heteroaryl group includes a heteroaryl ring fused to one or more (e.g., 1, 2 or 3) different cyclic groups (e.g., carbocyclic rings or heterocyclic rings), where the radical or point of attachment is on the heteroaryl ring, and in some embodiments wherein the point of attachment is a heteroatom contained in the heterocyclic ring.

The term heteroaryl also embraces N-heteroaryl groups which as used herein refers to a heteroaryl group, as defined above, and which contains at least one nitrogen atom and where the point of attachment of the N-heteroaryl group to the rest of the molecule is through a nitrogen atom in the heteroaryl group. The term heteroaryl further embraces C-heteroaryl groups which as used herein refer to a heteroaryl group as defined above and where the point of attachment of the heteroaryl group to the rest of the molecule is through a carbon atom in the heteroaryl group. The term heteroaryl further embraces heteroarylalkyl groups which as disclosed above refer to a group of the formula —$R^c$-heteroaryl, wherein $R^c$ is an alkylene chain as defined above. The term heteroaryl further embraces heteroaralkoxy (or heteroarylalkoxy) groups which as used herein refer to a group bonded through an oxygen atom of the formula —O—$R^c$-heteroaryl, where $R^c$ is an alkylene group as defined above.

Unless stated otherwise, and to the extent not further defined for any particular group(s), any of the groups described herein may be substituted or unsubstituted. As used herein, the term "substituted" broadly refers to all permissible substituents with the implicit proviso that such substitution is in accordance with permitted valence of the substituted atom and the substituent, and that the substitution results in a stable compound, i.e., a compound that does not spontaneously undergo transformation such as by rearrangement, cyclization, elimination, etc. Representative substituents include halogens, hydroxyl groups, and any other organic groupings containing any number of carbon atoms, e.g., 1-14 carbon atoms, and which may include one or more (e.g., 1, 2, 3, or 4) heteroatoms such as oxygen, sulfur, and nitrogen grouped in a linear, branched, or cyclic structural format.

To the extent not disclosed otherwise for any particular group(s), representative examples of substituents may include alkyl, substituted alkyl (e.g., $C_1$-$C_6$, $C_1$-$C_5$, $C_1$-$C_4$, $C_1$-$C_3$, $C_1$-$C_2$, $C_1$), alkoxy (e.g., $C_1$-$C_6$, $C_1$-$C_5$, $C_1$-$C_4$, $C_1$-$C_3$, $C_1$-$C_2$, $C_1$), substituted alkoxy (e.g., $C_1$-$C_6$, $C_1$-$C_5$, $C_1$-$C_4$, $C_1$-$C_3$, $C_1$-$C_2$, $C_1$), haloalkyl (e.g., $CF_3$), alkenyl (e.g., $C_2$-$C_6$, $C_2$-$C_5$, $C_2$-$C_4$, $C_2$-$C_3$, $C_2$), substituted alkenyl (e.g., $C_2$-$C_6$, $C_2$-$C_5$, $C_2$-$C_4$, $C_2$-$C_3$, $C_2$), alkynyl (e.g., $C_2$-$C_6$, $C_2$-$C_5$, $C_2$-$C_4$, $C_2$-$C_3$, $C_2$), substituted alkynyl (e.g., $C_2$-$C_6$, $C_2$-$C_5$, $C_2$-$C_4$, $C_2$-$C_3$, $C_2$), cyclic (e.g., $C_3$-$C_{12}$, $C_5$-$C_6$), substituted cyclic (e.g., $C_3$-$C_{12}$, $C_5$-$C_6$), carbocyclic (e.g., $C_3$-$C_{12}$, $C_5$-$C_6$), substituted carbocyclic (e.g., $C_3$-$C_{12}$, $C_5$-$C_6$), heterocyclic (e.g., $C_3$-$C_{12}$, $C_5$-$C_6$), substituted heterocyclic (e.g., $C_3$-$C_{12}$, $C_5$-$C_6$), aryl (e.g., benzyl and phenyl), substituted aryl (e.g., substituted benzyl or phenyl), heteroaryl (e.g., pyridyl or pyrimidyl), substituted heteroaryl (e.g., substituted pyridyl or pyrimidyl), aralkyl (e.g., benzyl), substituted aralkyl (e.g., substituted benzyl), halo, hydroxyl, aryloxy (e.g., $C_6$-$C_{12}$, $C_6$), substituted aryloxy (e.g., $C_6$-$C_{12}$, $C_6$), alkylthio (e.g., $C_1$-$C_6$), substituted alkylthio (e.g., $C_1$-$C_6$), arylthio (e.g., $C_6$-$C_{12}$, $C_6$), substituted arylthio (e.g., $C_6$-$C_{12}$, $C_6$), cyano, carbonyl, substituted carbonyl, carboxyl, substituted carboxyl, amino, substituted amino, amido, substituted amido, thio, substituted thio, sulfinyl, substituted sulfinyl, sulfonyl, substituted sulfonyl, sulfinamide, substituted sulfinamide, sulfonamide, substituted sulfonamide, urea, substituted urea, carbamate, substituted carbamate, amino acid, and peptide groups.

In one aspect of the present disclosure is provided a bifunctional compound, or a pharmaceutically acceptable salt or stereoisomer thereof, having a structure represented by formula (I):

(I)

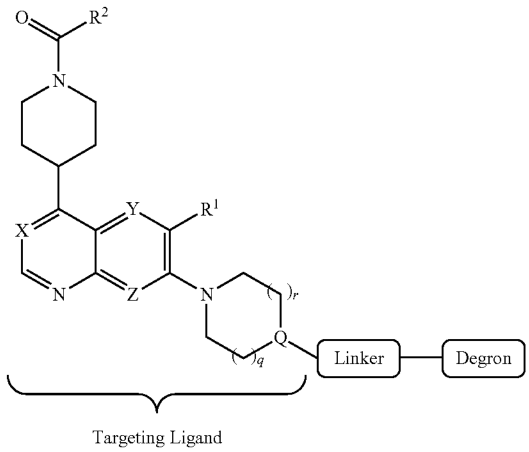

, wherein X is CH, $CR^3$, or N; Y is CH, $CR^3$, or N; Z is CH, $CR^3$, or N; Q is CH or N; $R^1$ is H, $C_1$-$C_6$ alkyl, or $C_1$-$C_6$ alkoxy; $R^2$ is a phenyl or pyridyl ring which is optionally substituted once or twice identically or differently with a substituent selected from halogen, OH, CN, $C_1$-$C_6$ alkyl, $C_1$-$C_6$ alkoxy, $C_1$-$C_6$ haloalkoxy, $C_1$-$C_6$ alkyl which is optionally substituted with a $C_1$-$C_6$ alkoxy- or $C_1$-$C_6$ haloalkoxy-substituent, $C_2$-$C_6$-alkenyl, $C_2$-$C_6$-alkynyl, $C_3$-$C_8$-cycloalkyl, —C(═O)$NR^4R^5$, —$NH_2$, —NH—C(═O)—$C_1$-$C_6$-alkyl, $C_1$-$C_6$-alkoxy which is optionally substituted with a hydroxyl or $C_1$-$C_6$-alkyl substituent, —O—$C_3$-$C_8$-cycloalkyl, —O-(4- to 7-membered heterocycloalkyl), $C_1$-$C_6$-alkylthio, $C_1$-$C_6$-haloalkylthio, or —S(═O)$_2$—$C_1$-$C_6$-alkyl group; $R^3$ is H, or $C_1$-$C_6$ alkyl; $R^4$ and $R^5$ independently represent hydrogen, a $C_1$-$C_6$-alkyl or phenyl group; each occurrence of q and r is independently 0 or 1; the targeting ligand binds ERK5; the degron ("Degron") represents a moiety that binds an E3 ubiquitin ligase; and the linker ("Linker") provides a covalent attachment between the targeting ligand and the degron.

In some aspects of the present disclosure, Y is CH and Z is CH. In some aspects of the present disclosure, q is 1 and r is 1. In some aspects of the present disclosure, Q is N. In some aspects of the present disclosure, X is N.

In some aspects of the present disclosure, $R^2$ is a phenyl which is optionally substituted once or twice identically or differently with a substituent selected from halogen, OH, CN, $C_1$-$C_6$ alkyl, $C_1$-$C_6$ alkoxy, $C_1$-$C_6$ haloalkoxy, $C_1$-$C_6$ alkyl which is optionally substituted with a $C_1$-$C_6$ alkoxy- or $C_1$-$C_6$ haloalkoxy-substituent, $C_2$-$C_6$-alkenyl, $C_2$-$C_6$-alkynyl, $C_3$-$C_8$-cycloalkyl, —C(═O)$NR^4R^5$, —$NH_2$, —NH—C(═O)—$C_1$-$C_6$-alkyl, $C_1$-$C_6$-alkoxy which is optionally substituted with a hydroxyl or $C_1$-$C_6$-alkyl substituent, —O—$C_3$-$C_8$-cycloalkyl, —O-(4- to 7-membered heterocycloalkyl), $C_1$-$C_6$-alkylthio, $C_1$-$C_6$-haloalkylthio, or —S(═O)$_2$—$C_1$-$C_6$-alkyl group, and wherein $R^4$ and $R^5$ independently represent hydrogen, a $C_1$-$C_6$-alkyl or phenyl group. In some embodiments, $R^2$ is a phenyl which is optionally substituted once or twice identically or differently with a $C_1$-$C_6$ haloalkoxy group. In some embodiments, the $C_1$-$C_6$ haloalkoxy group is a $C_1$-$C_6$ trifluoroalkoxy group. In some embodiments, the $C_1$-$C_6$ trifluoroalkoxy group is a trifluoromethoxy group.

In some aspects of the present disclosure, $R^2$ is

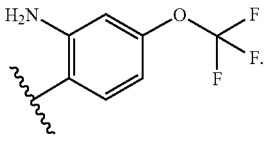 [SMILES: *c1ccc(OC(F)(F)F)cc1N]

In some embodiments, the degron binds a Von Hippel-Lindau (VHL) tumor suppressor. In some embodiments, the degron is represented by any one of the following structures:

(V1)

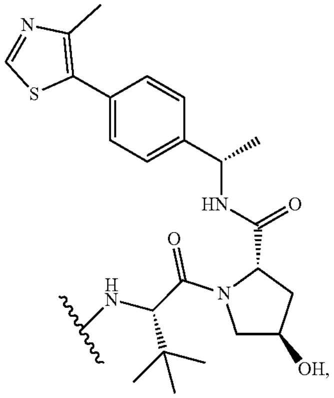

, and (V2)

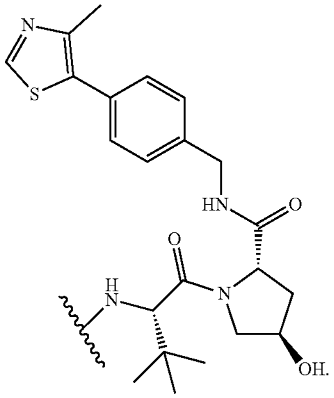

.

Yet other degrons that bind VHL, and which may be suitable for use as degrons in the present disclosure are disclosed in U.S. Patent Application Publication 2017/0121321 A1.

In some embodiments, the degron binds cereblon (CRBN). In some embodiments, the degron is represented by any one of the following structures:

(C1)

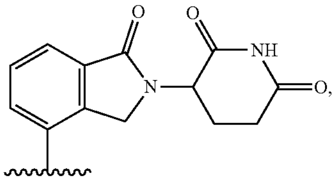

, (C2)

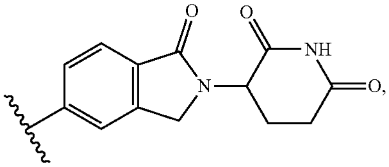

, and (C3)

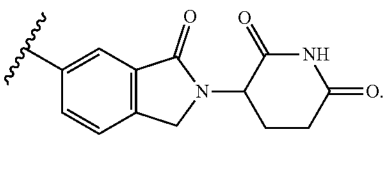

.

Yet other degrons that bind cereblon and which may be suitable for use as degrons in the present disclosure are described in U.S. Patent Application Publication 2018/0015087 (e.g., the indolinones such as isoindolinones and isoindoline-1,3-diones embraced by formulae IA ad IA' therein, and the bridged cycloalkyl compounds embraced by formulae IB and IB' therein).

In some embodiments, the linker provides a covalent attachment between the targeting ligand and the degron. The structure of the linker may not be critical, provided it does not substantially interfere with the activity of the targeting ligand or the degron.

In some embodiments, the linker comprises an alkylene chain which may be interrupted by, and/or terminate (at either or both termini) in at least one of —O—, —S—, —N(R')—, —C≡C—, —C(O)—, —C(O)O—, —OC(O)—, —OC(O)O—, —C(NOR')—, —C(O)N(R')—, —C(O)N(R')C(O)—, —C(O)N(R')C(O)N(R')—, —N(R')C(O)—, —N(R')C(O)N(R')—, —N(R')C(O)O—, —OC(O)N(R')—, —C(NR')—, —N(R')C(NR')—, —C(NR')N(R')—, —N(R')C(NR')N(R')—, —OB(Me)O—, —$S(O)_2$—, —OS(O)—, —S(O)O—, —S(O)—, —$OS(O)_2$—, —$S(O)_2O$—, —$N(R')S(O)_2$—, —$S(O)_2N(R')$—, —N(R')S(O)—, —S(O)N(R')—, —$N(R')S(O)_2N(R')$—, —N(R')S(O)N(R')—, $C_3$-$C_{12}$ carbocyclene, 3- to 12-membered heterocyclene, 5- to 12-membered heteroarylene or any combination thereof, wherein R' is H, F, or $C_1$-$C_6$ alkyl, and wherein the interrupting and the one or both terminating groups may be the same or different. In some embodiments, the alkylene chain comprises 1-10 alkylene units. In some embodiments, the alkylene group contains one to 8 carbon atoms ($C_1$-$C_8$ alkylene). In other embodiments, an alkylene group contains one to 5 carbon atoms ($C_1$-$C_5$ alkylene). In other embodiments, an alkylene group contains one to 4 carbon atoms ($C_1$-$C_4$ alkylene). In other embodiments, an alkylene contains one to three carbon atoms ($C_1$-$C_3$ alkylene). In other embodiments, an alkylene group contains one to two carbon atoms ($C_1$-$C_2$ alkylene). In other embodiments, an alkylene group contains one carbon atom ($C_1$ alkylene).

In some embodiments, the linker comprises a polyethylene glycol (PEG) chain which may terminate (at either or both termini) in at least one of —S—, —N(R')—, —C≡C—, —C(O)—, —C(O)O—, —OC(O)—, —OC(O)O—, —C(NOR')—, —C(O)N(R')—, —C(O)N(R')C(O)—, —C(O)N(R')C(O)N(R')—, —N(R')C(O)—, —N(R')C(O)N(R')—, —N(R')C(O)O—, —OC(O)N(R')—, —C(NR')—, —N(R')C(NR')—, —C(NR')N(R')—, —N(R')C(NR')N(R')—, —OB(Me)O—, —$S(O)_2$—, —OS(O)—, —S(O)O—, —S(O)—, —$OS(O)_2$—, —$S(O)_2O$—, —$N(R')S(O)_2$—, —$S(O)_2N(R')$—, —N(R')S(O)—, —S(O)N(R')—, —$N(R')S(O)_2N(R')$—, —N(R')S(O)N(R')—, $C_{3-12}$ carbocyclene, 3- to 12-membered heterocyclene, 5- to 12-membered heteroarylene or any combination thereof, wherein R' is H, F, or $C_1$-$C_6$ alkyl, and wherein the one or both terminating groups may be the same or different. In some embodiments, the polyethylene glycol chain comprises 1-6 PEG units.

In some embodiments, the linker is represented by any one of the structures:

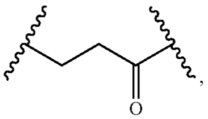

,

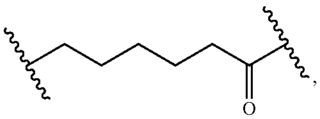

,

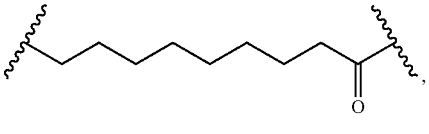

,

-continued
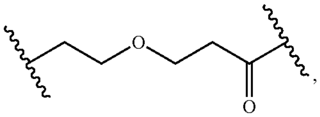,
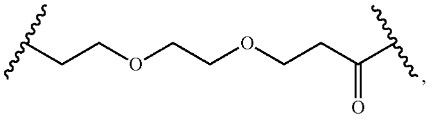,
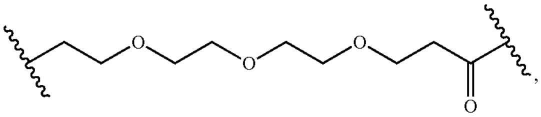,
-continued
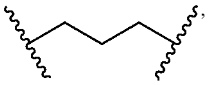,
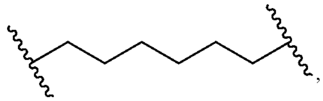, and
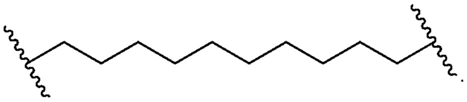.
In some embodiments, the bifunctional compound, or a pharmaceutically acceptable salt or stereoisomer thereof, is:
(1)
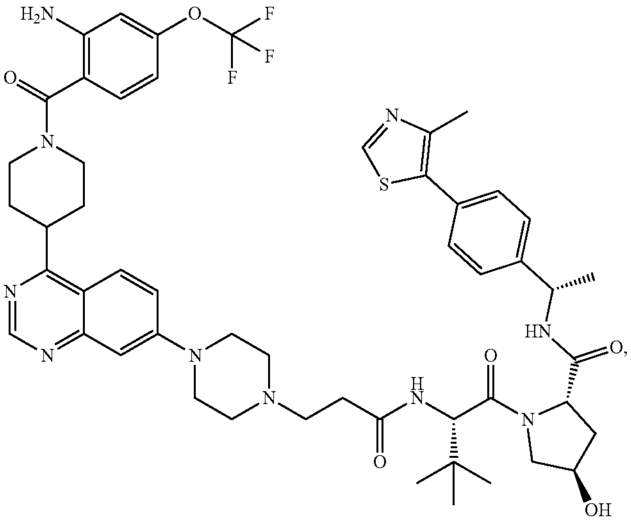
(2)
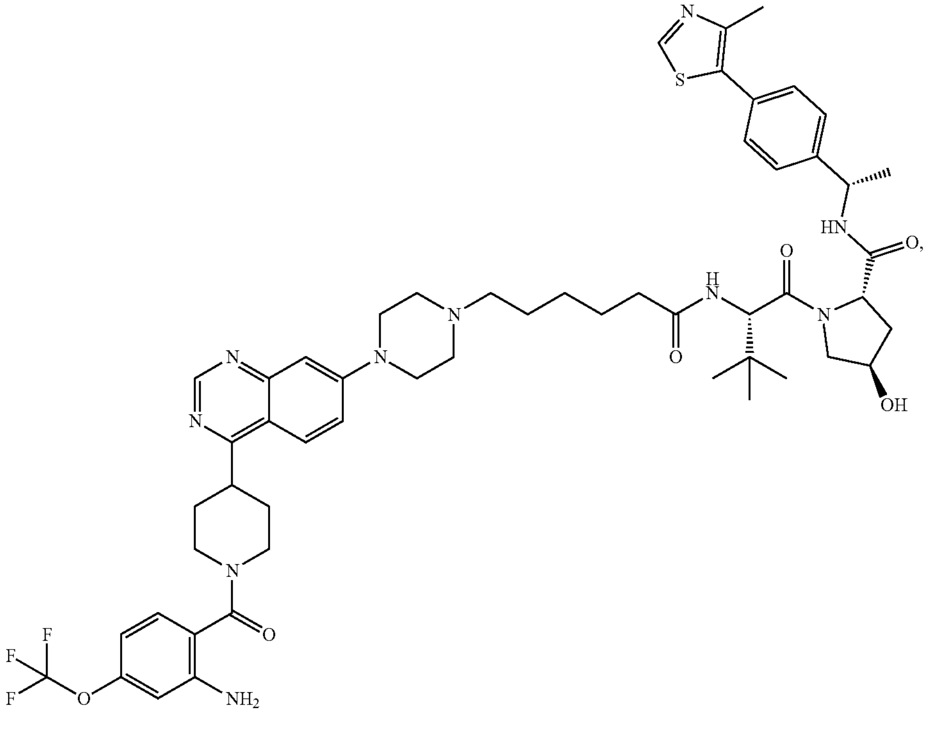

-continued
(3)
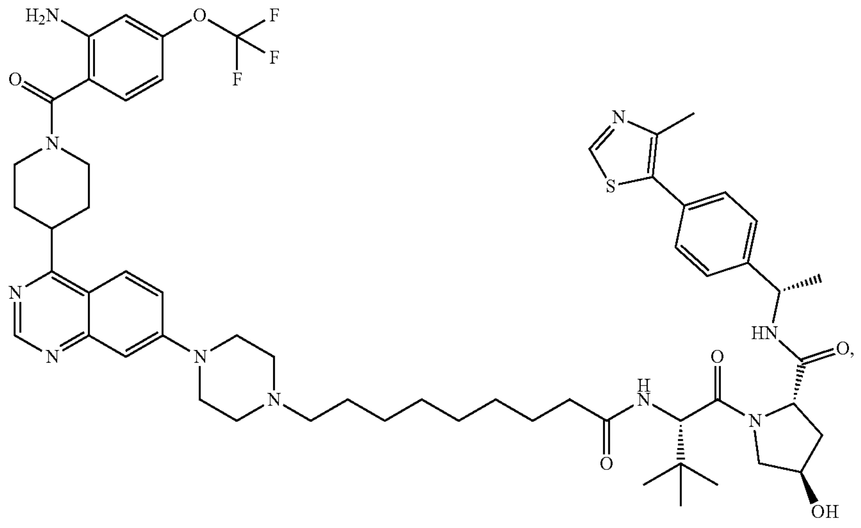
(4)
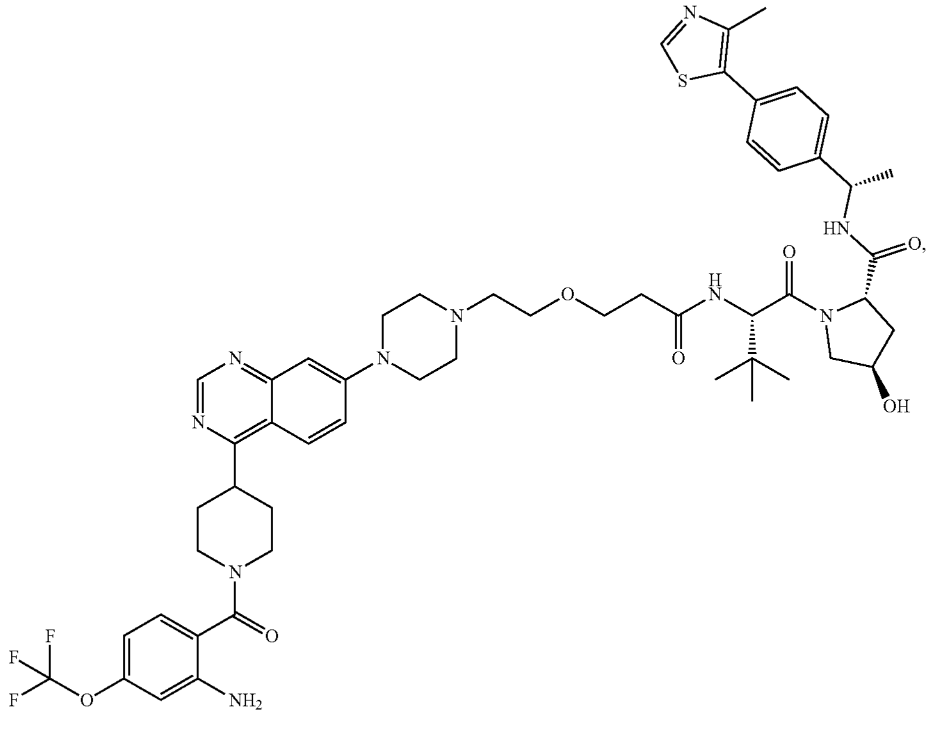

-continued
(5)
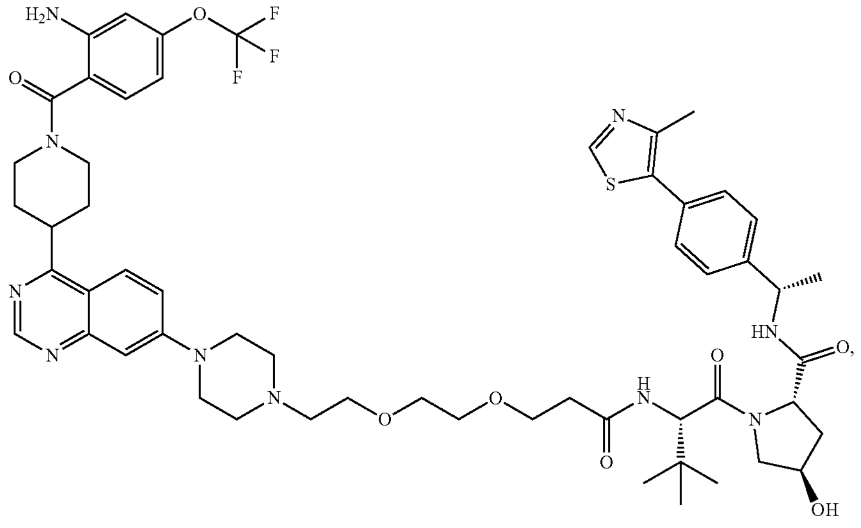
(6)
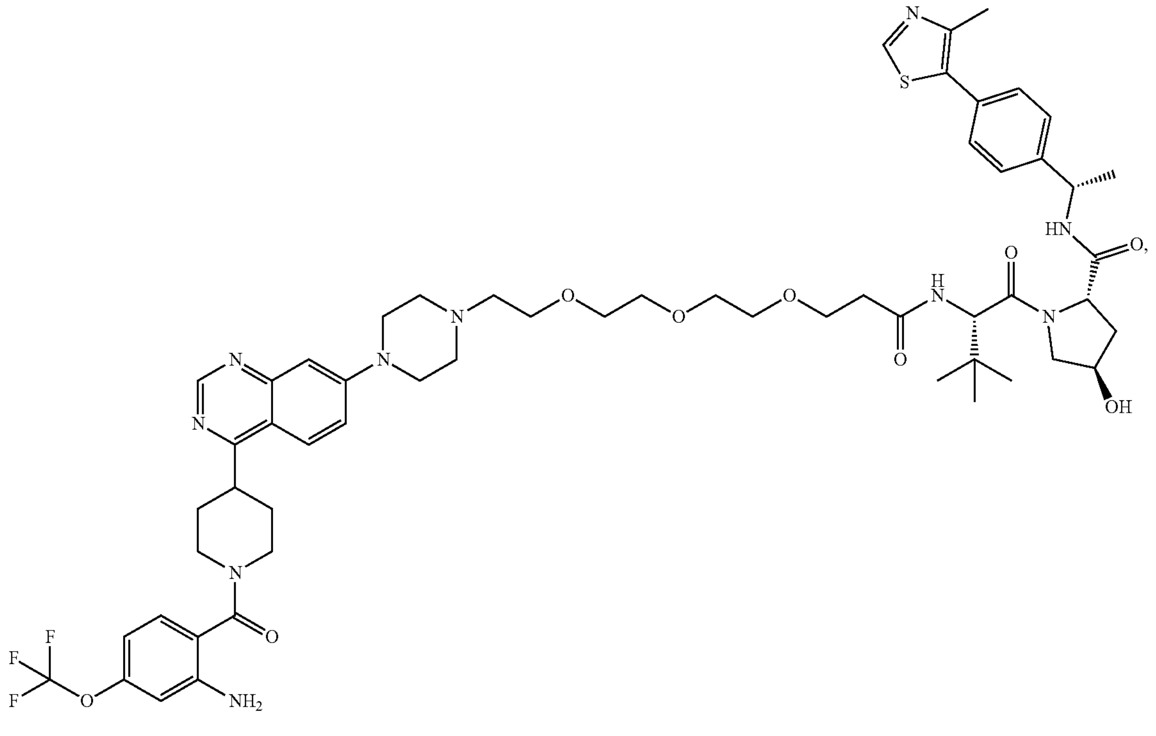

-continued
(7)
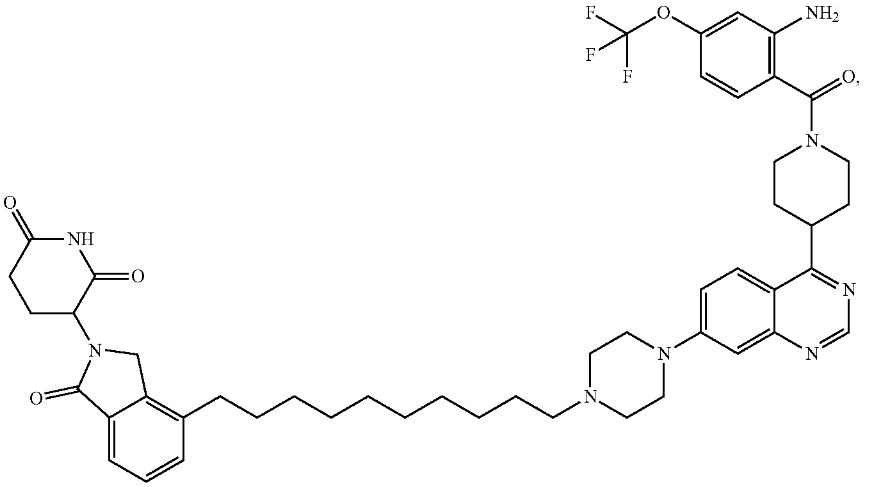
(8)
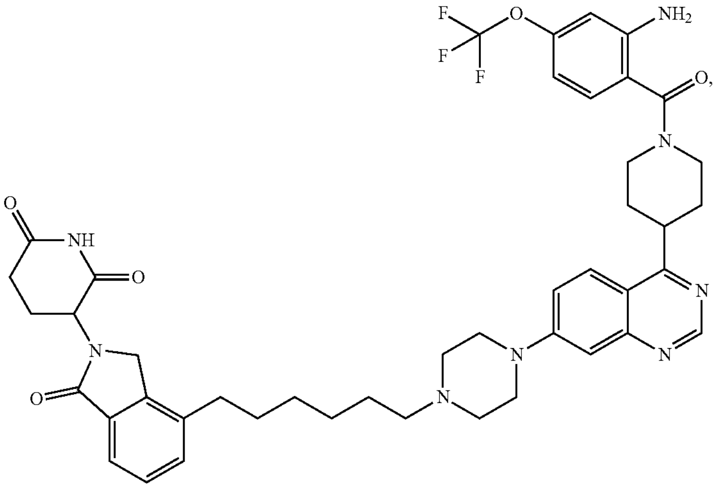
(9)
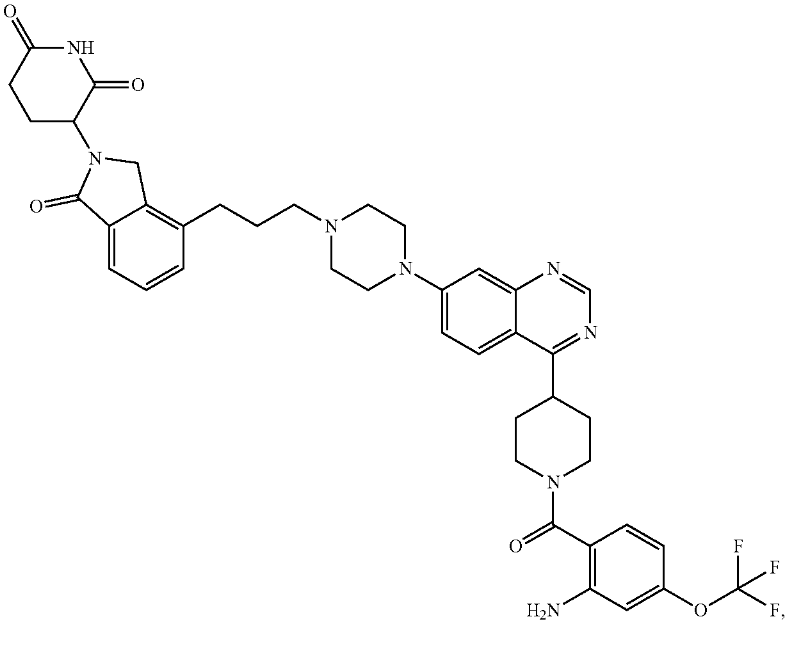

-continued
(10)
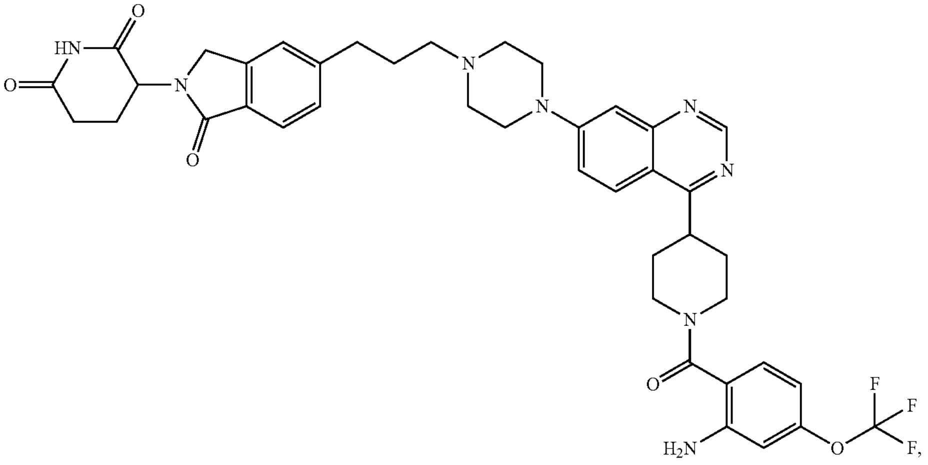
(11)
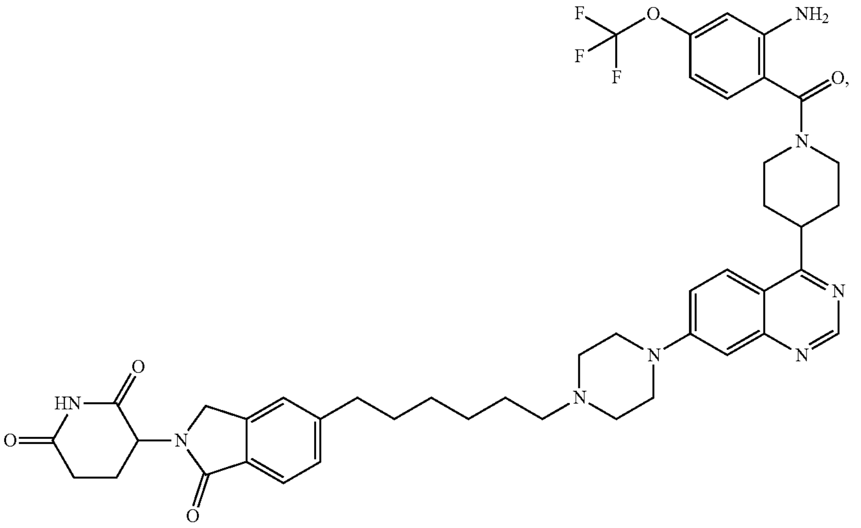
or
(12)
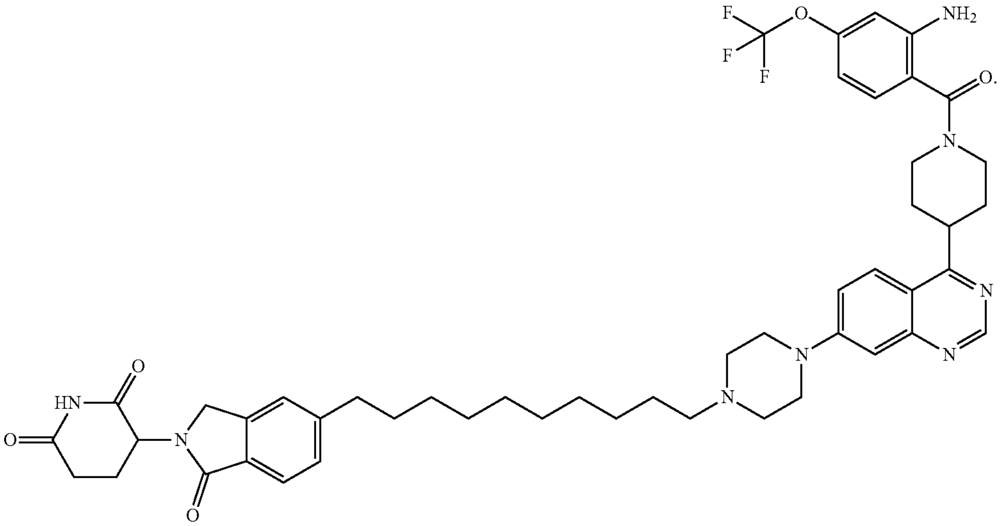

Bifunctional compounds of formula (I) may be in the form of a free acid or free base, or a pharmaceutically acceptable salt. As used herein, the term "pharmaceutically acceptable" in the context of a salt refers to a salt of the compound that does not abrogate the biological activity or properties of the compound, and is relatively non-toxic, i.e., the compound in salt form may be administered to a subject without causing undesirable biological effects (such as dizziness or gastric upset) or interacting in a deleterious manner with any of the other components of the composition in which it is contained. The term "pharmaceutically acceptable salt" refers to a product obtained by reaction of the bifunctional compound of the present disclosure with a suitable acid or a base. Examples of pharmaceutically acceptable salts of the bifunctional compounds of this disclosure include those derived from suitable inorganic bases such as Li, Na, K, Ca, Mg, Fe, Cu, Al, Zn and Mn salts. Examples of pharmaceutically acceptable, nontoxic acid addition salts are salts of an amino group formed with inorganic acids such as hydrochloride, hydrobromide, hydroiodide, nitrate, sulfate, bisulfate, phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, 4-methylbenzenesulfonate or p-toluenesulfonate salts and the like. Certain bifunctional compounds of the disclosure can form pharmaceutically acceptable salts with various organic bases such as lysine, arginine, guanidine, diethanolamine or metformin. Suitable base salts include aluminum, calcium, lithium, magnesium, potassium, sodium, or zinc salts.

Bifunctional compounds of the present disclosure may have at least one chiral center and thus may be in the form of a stereoisomer, which, as used herein, embraces all isomers of individual compounds that differ only in the orientation of their atoms in space. The term stereoisomer includes mirror image isomers (enantiomers which include the (R—) or (S—) configurations of the compounds), mixtures of mirror image isomers (physical mixtures of the enantiomers, and racemates or racemic mixtures) of compounds, geometric (cis/trans or E/Z, R/S) isomers of compounds and isomers of compounds with more than one chiral center that are not mirror images of one another (diastereoisomers). The chiral centers of the compounds may undergo epimerization in vivo; thus, for these compounds, administration of the compound in its (R—) form is considered equivalent to administration of the compound in its (S—) form. Accordingly, the compounds of the present disclosure may be made and used in the form of individual isomers and substantially free of other isomers, or in the form of a mixture of various isomers, e.g., racemic mixtures of stereoisomers.

In some embodiments, the bifunctional compound is an isotopic derivative in that it has at least one desired isotopic substitution of an atom, at an amount above the natural abundance of the isotope, i.e., enriched. In one embodiment, the bifunctional compound includes deuterium or multiple deuterium atoms. Substitution with heavier isotopes such as deuterium, i.e., $^2H$, may afford certain therapeutic advantages resulting from greater metabolic stability, for example, increased in vivo half-life or reduced dosage requirements, and thus may be advantageous in some circumstances.

Bifunctional compounds of formula (I) may also be in the form of N-oxides, crystalline forms (also known as polymorphs), active metabolites of the compounds having the same type of activity, prodrugs, tautomers, and unsolvated as well as solvated (e.g., hydrated) forms with pharmaceutically acceptable solvents such as water, ethanol, and the like, of the compounds.

The bifunctional compounds of the present disclosure may be prepared by crystallization under different conditions and may exist as one or a combination of polymorphs of the compound. For example, different polymorphs may be identified and/or prepared using different solvents, or different mixtures of solvents for recrystallization, by performing crystallizations at different temperatures, or by using various modes of cooling, ranging from very fast to very slow cooling during crystallizations. Polymorphs may also be obtained by heating or melting the compound followed by gradual or fast cooling. The presence of polymorphs may be determined by solid probe NMR spectroscopy, IR spectroscopy, differential scanning calorimetry, powder X-ray diffractogram and/or other known techniques.

In some embodiments, the pharmaceutical composition comprises a co-crystal of a bifunctional compound of the disclosure. The term "co-crystal", as used herein, refers to a stoichiometric multi-component system comprising a bifunctional compound of the disclosure and a co-crystal former wherein the bifunctional compound of the disclosure and the co-crystal former are connected by non-covalent interactions. The term "co-crystal former", as used herein, refers to compounds which can form intermolecular interactions with a bifunctional compound of the disclosure and co-crystallize with it. Representative examples of co-crystal formers include benzoic acid, succinic acid, fumaric acid, glutaric acid, trans-cinnamic acid, 2,5-dihydroxybenzoic acid, glycolic acid, trans-2-hexanoic acid, 2-hydroxycaproic acid, lactic acid, sorbic acid, tartaric acid, ferulic acid, suberic acid, picolinic acid, salicyclic acid, maleic acid, saccharin, 4,4'-bipyridine p-aminosalicyclic acid, nicotinamide, urea, isonicotinamide, methyl-4-hydroxybenzoate, adipic acid, terephthalic acid, resorcinol, pyrogallol, phloroglucinol, hydroxyquinol, isoniazid, theophylline, adenine, theobromine, phenacetin, phenazone, etofylline, and phenobarbital.

Methods of Synthesis

In another aspect, the present disclosure is directed to a method for making a bifunctional compound of formula (I), or a pharmaceutically acceptable salt or stereoisomer thereof. Broadly, the bifunctional compounds or pharmaceutically acceptable salts or stereoisomers thereof may be prepared by any process known to be applicable to the preparation of chemically related compounds. The bifunctional compounds of the present disclosure will be better understood in connection with the synthetic schemes that described in various working examples and which illustrate non-limiting methods by which the bifunctional compounds of the disclosure may be prepared.

Pharmaceutical Compositions

Another aspect of the present disclosure is directed to a pharmaceutical composition that includes a therapeutically effective amount of a bifunctional compound of formula (I) or a pharmaceutically acceptable salt or stereoisomer thereof, and a pharmaceutically acceptable carrier. The term "pharmaceutically acceptable carrier," as known in the art, refers to a pharmaceutically acceptable material, composition or vehicle, suitable for administering bifunctional compounds of the present disclosure to mammals. Suitable carriers may include, for example, liquids (both aqueous and non-aqueous alike, and combinations thereof), solids, encapsulating materials, gases, and combinations thereof (e.g., semi-solids), and gases, that function to carry or transport the compound from one organ, or portion of the body, to another organ, or portion of the body. A carrier is "acceptable" in the sense of being physiologically inert to and compatible with the other ingredients of the formulation and not injurious to the subject or patient. Depending on the type of formulation, the composition may also include one or more pharmaceutically acceptable excipients.

Broadly, bifunctional compounds of formula (I) and their pharmaceutically acceptable salts and stereoisomers may be formulated into a given type of composition in accordance with conventional pharmaceutical practice such as conventional mixing, dissolving, granulating, dragee-making, levigating, emulsifying, encapsulating, entrapping and compression processes (see, e.g., Remington: *The Science and Practice of Pharmacy* (20th ed.), ed. A. R. Gennaro, Lippincott Williams & Wilkins, 2000 and *Encyclopedia of Pharmaceutical Technology*, eds. J. Swarbrick and J. C. Boylan, 1988-1999, Marcel Dekker, New York). The type of formulation depends on the mode of administration which may include enteral (e.g., oral, buccal, sublingual and rectal), parenteral (e.g., subcutaneous (s.c.), intravenous (i.v.), intramuscular (i.m.), and intrasternal injection, or infusion techniques, intra-ocular, intra-arterial, intramedullary, intrathecal, intraventricular, transdermal, interdermal, intravaginal, intraperitoneal, mucosal, nasal, intratracheal instillation, bronchial instillation, and inhalation) and topical (e.g., transdermal). In general, the most appropriate route of administration will depend upon a variety of factors including, for example, the nature of the agent (e.g., its stability in the environment of the gastrointestinal tract), and/or the condition of the subject (e.g., whether the subject is able to tolerate oral administration). For example, parenteral (e.g., intravenous) administration may also be advantageous in that the compound may be administered relatively quickly such as in the case of a single-dose treatment and/or an acute condition.

In some embodiments, the bifunctional compounds are formulated for oral or intravenous administration (e.g., systemic intravenous injection).

Accordingly, bifunctional compounds of formula (I) may be formulated into solid compositions (e.g., powders, tablets, dispersible granules, capsules, cachets, and suppositories), liquid compositions (e.g., solutions in which the compound is dissolved, suspensions in which solid particles of the compound are dispersed, emulsions, and solutions containing liposomes, micelles, or nanoparticles, syrups and elixirs); semi-solid compositions (e.g., gels, suspensions and creams); and gases (e.g., propellants for aerosol compositions). Bifunctional compounds may also be formulated for rapid, intermediate or extended release.

Solid dosage forms for oral administration include capsules, tablets, pills, powders, and granules. In such solid dosage forms, the active compound is mixed with a carrier such as sodium citrate or dicalcium phosphate and an additional carrier or excipient such as a) fillers or extenders such as starches, lactose, sucrose, glucose, mannitol, and silicic acid, b) binders such as, for example, methylcellulose, microcrystalline cellulose, hydroxypropylmethylcellulose, carboxymethylcellulose, sodium carboxymethylcellulose, alginates, gelatin, polyvinylpyrrolidinone, sucrose, and acacia, c) humectants such as glycerol, d) disintegrating agents such as crosslinked polymers (e.g., crosslinked polyvinylpyrrolidone (crospovidone), crosslinked sodium carboxymethyl cellulose (croscarmellose sodium), sodium starch glycolate, agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also include buffering agents. Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings. They may further contain an opacifying agent.

In some embodiments, bifunctional compounds of formula (I) may be formulated in a hard or soft gelatin capsule. Representative excipients that may be used include pregelatinized starch, magnesium stearate, mannitol, sodium stearyl fumarate, lactose anhydrous, microcrystalline cellulose and croscarmellose sodium. Gelatin shells may include gelatin, titanium dioxide, iron oxides and colorants.

Liquid dosage forms for oral administration include solutions, suspensions, emulsions, micro-emulsions, syrups and elixirs. In addition to the compound, the liquid dosage forms may contain an aqueous or non-aqueous carrier (depending upon the solubility of the compounds) commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Oral compositions may also include an excipients such as wetting agents, suspending agents, coloring, sweetening, flavoring, and perfuming agents.

Injectable preparations for parenteral administration may include sterile aqueous solutions or oleaginous suspensions. They may be formulated according to standard techniques using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. The effect of the compound may be prolonged by slowing its absorption, which may be accomplished by the use of a liquid suspension or crystalline or amorphous material with poor water solubility. Prolonged absorption of the compound from a parenterally administered formulation may also be accomplished by suspending the compound in an oily vehicle.

In certain embodiments, bifunctional compounds of formula (I) may be administered in a local rather than systemic manner, for example, via injection of the conjugate directly into an organ, often in a depot preparation or sustained release formulation. In specific embodiments, long-acting formulations are administered by implantation (for example subcutaneously or intramuscularly) or by intramuscular injection. Injectable depot forms are made by forming microencapsule matrices of the compound in a biodegradable polymer, e.g., polylactide-polyglycolides, poly(orthoesters) and poly(anhydrides). The rate of release of the compound may be controlled by varying the ratio of compound to polymer and the nature of the particular polymer employed. Depot injectable formulations are also prepared by entrapping the compound in liposomes or microemulsions that are compatible with body tissues. Furthermore, in other embodiments, the compound is delivered in a targeted drug delivery system, for example, in a liposome coated with organ-specific antibody. In such embodiments, the liposomes are targeted to and taken up selectively by the organ.

The compositions may be formulated for buccal or sublingual administration, examples of which include tablets, lozenges and gels.

The bifunctional compounds of formula (I) may be formulated for administration by inhalation. Various forms suitable for administration by inhalation include aerosols, mists or powders. Pharmaceutical compositions may be delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide or other suitable gas). In some embodiments, the dosage unit of a pressurized aerosol may be determined by providing a valve to deliver a metered amount. In some embodiments, capsules and cartridges including gelatin, for example, for use in an inhaler or insufflator, may be formulated containing a powder mix of the compound and a suitable powder base such as lactose or starch.

Bifunctional compounds of formula (I) may be formulated for topical administration which as used herein, refers to administration intradermally by disclosure of the formulation to the epidermis. These types of compositions are typically in the form of ointments, pastes, creams, lotions, gels, solutions and sprays.

Representative examples of carriers useful in formulating compounds for topical application include solvents (e.g., alcohols, poly alcohols, water), creams, lotions, ointments, oils, plasters, liposomes, powders, emulsions, microemulsions, and buffered solutions (e.g., hypotonic or buffered saline). Creams, for example, may be formulated using saturated or unsaturated fatty acids such as stearic acid, palmitic acid, oleic acid, palmito-oleic acid, cetyl, or oleyl alcohols. Creams may also contain a non-ionic surfactant such as polyoxy-40-stearate.

In some embodiments, the topical formulations may also include an excipient, an example of which is a penetration enhancing agent. These agents are capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, *Percutaneous Penetration Enhancers*, Maibach H. I. and Smith H. E. (eds.), CRC Press, Inc., Boca Raton, Fla. (1995), which surveys the use and testing of various skin penetration enhancers, and Buyuktimkin et al., *Chemical Means of TransdermalDrug Permeation Enhancement in Transdermal and Topical Drug Delivery Systems*, Gosh T. K., Pfister W. R., Yum S. I. (Eds.), Interpharm Press Inc., Buffalo Grove, Ill. (1997). Representative examples of penetration enhancing agents include triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate), and N-methylpyrrolidone.

Representative examples of yet other excipients that may be included in topical as well as in other types of formulations (to the extent they are compatible), include preservatives, antioxidants, moisturizers, emollients, buffering agents, solubilizing agents, skin protectants, and surfactants. Suitable preservatives include alcohols, quaternary amines, organic acids, parabens, and phenols. Suitable antioxidants include ascorbic acid and its esters, sodium bisulfite, butylated hydroxytoluene, butylated hydroxyanisole, tocopherols, and chelating agents like EDTA and citric acid. Suitable moisturizers include glycerin, sorbitol, polyethylene glycols, urea, and propylene glycol. Suitable buffering agents include citric, hydrochloric, and lactic acid buffers. Suitable solubilizing agents include quaternary ammonium chlorides, cyclodextrins, benzyl benzoate, lecithin, and polysorbates. Suitable skin protectants include vitamin E oil, allatoin, dimethicone, glycerin, petrolatum, and zinc oxide.

Transdermal formulations typically employ transdermal delivery devices and transdermal delivery patches wherein the compound is formulated in lipophilic emulsions or buffered, aqueous solutions, dissolved and/or dispersed in a polymer or an adhesive. Patches may be constructed for continuous, pulsatile, or on demand delivery of pharmaceutical agents. Transdermal delivery of the compounds may be accomplished by means of an iontophoretic patch. Transdermal patches may provide controlled delivery of the compounds wherein the rate of absorption is slowed by using rate-controlling membranes or by trapping the compound within a polymer matrix or gel. Absorption enhancers may be used to increase absorption, examples of which include absorbable pharmaceutically acceptable solvents that assist passage through the skin.

Ophthalmic formulations include eye drops.

Formulations for rectal administration include enemas, rectal gels, rectal foams, rectal aerosols, and retention enemas, which may contain conventional suppository bases such as cocoa butter or other glycerides, as well as synthetic polymers such as polyvinylpyrrolidone, PEG, and the like. Compositions for rectal or vaginal administration may also be formulated as suppositories which can be prepared by mixing the compound with suitable non-irritating carriers and excipients such as cocoa butter, mixtures of fatty acid glycerides, polyethylene glycol, suppository waxes, and combinations thereof, all of which are solid at ambient temperature but liquid at body temperature and therefore melt in the rectum or vaginal cavity and release the compound.

Dosage Amounts

As used herein, the term, "therapeutically effective amount" refers to an amount of a bifunctional compound of formula (I) or a pharmaceutically acceptable salt or a stereoisomer thereof that is effective in producing the desired therapeutic response in a particular patient suffering from a disease or disorder mediated by aberrant ERK5 activity. The term "therapeutically effective amount" thus includes the amount of the bifunctional compound or a pharmaceutically acceptable salt or a stereoisomer thereof, that when administered, induces a positive modification in the disease or disorder to be treated, or is sufficient to prevent development or progression of the disease or disorder, or alleviate to some extent, one or more of the symptoms of the disease or disorder being treated in a subject, or which simply kills or inhibits the growth of diseased (e.g., cancer) cells, or reduces the amounts of ERK5 in diseased cells.

The total daily dosage of the bifunctional compounds and usage thereof may be decided in accordance with standard medical practice, e.g., by the attending physician using sound medical judgment. The specific therapeutically effective dose for any particular subject may depend upon a variety of factors including the disease or disorder being treated and the severity thereof (e.g., its present status); the age, body weight, general health, sex and diet of the subject; the time of administration, route of administration, and rate of excretion of the specific compound employed; the duration of the treatment; drugs used in combination or coincidental with the compound; and like factors well known in the medical arts (see, for example, *Goodman and Gilman's, The Pharmacological Basis of Therapeutics,* 10th Edition, A. Gilman, J. Hardman and L. Limbird, eds., McGraw-Hill Press, 155-173, 2001).

Bifunctional compounds of formula (I) and their pharmaceutically acceptable salts and stereoisomers may be effective over a wide dosage range. In some embodiments, the total daily dosage (e.g., for adult humans) may range from about 0.001 to about 1600 mg, from 0.01 to about 1600 mg, from 0.01 to about 500 mg, from about 0.01 to about 100 mg, from about 0.5 to about 100 mg, from 1 to about 100-400 mg per day, from about 1 to about 50 mg per day, and from about 5 to about 40 mg per day, or in yet other embodiments from about 10 to about 30 mg per day. In some embodiments, the total daily dosage may range from 400 mg to 600 mg. Individual dosages may be formulated to contain the desired dosage amount depending upon the number of times the compound is administered per day. By way of example, capsules may be formulated with from about 1 to about 200 mg of compound (e.g., 1, 2, 2.5, 3, 4, 5, 10, 15, 20, 25, 50, 100, 150, and 200 mg). In some embodiments, the compound may be administered at a dose in range from about 0.001 mg/kg to about 200 mg/kg of body weight per day. In some embodiments, a dose of from 0.1 to 100, e.g., from 1 to 30 mg/kg per day in one or more dosages per day may be effective. By way of example, a suitable dose for oral administration may be in the range of 1-30 mg/kg of body weight per day, and a suitable dose for intravenous administration may be in the range of 1-10 mg/kg of body weight per day.

In some embodiments, bifunctional compounds of formula (I) and their pharmaceutically acceptable salts and stereoisomers may be administered at dosage levels of about 0.001 mg/kg to about 50 mg/kg, from about 0.01 mg/kg to about 25 mg/kg, or from about 0.1 mg/kg to about 10 mg/kg of subject body weight per day, one or more times a day, to obtain the desired therapeutic effect.

Methods of Use

In some aspects, the present disclosure is directed to treating diseases or disorders characterized or mediated by aberrant (e.g., elevated levels of ERK5 or otherwise functionally abnormal e.g., dysfunctional ERK5 levels) ERK5 activity relative to a non-pathological state. The methods entail administering a therapeutically effective amount of a bifunctional compound of formula (I) or a pharmaceutically acceptable salt or stereoisomer thereof, to a subject in need thereof. A "disease" is generally regarded as a state of health of a subject wherein the subject cannot maintain homeostasis, and wherein if the disease is not ameliorated then the subject's health continues to deteriorate. In contrast, a "disorder" in a subject is a state of health in which the subject is able to maintain homeostasis, but in which the subject's state of health is less favorable than it would be in the absence of the disorder. Left untreated, a disorder does not necessarily cause a further decrease in the subject's state of health. In some embodiments, the disease or disorder is cancer. In some embodiments, the cancer is leukemia, breast cancer, multiple myeloma, colon cancer, renal cancer, mesothelioma, pancreatic cancer, liver cancer, melanoma, or lung cancer.

In some embodiments, the disease or disorder is an inflammatory disease. In some embodiments, the inflammatory disease is rheumatoid arthritis, coeliac disease scleroderma, Sjogren's syndrome, lupus, vasculitis, myositis, gout, ankylosing spondylitis, or inflammatory bowel disease.

A further aspect of the present disclosures is directed to methods of reducing the levels of ERK5 in a cell, either in vitro or in vivo, comprising contacting the cell with an effective amount of the bifunctional compound or pharmaceutically acceptable salt or stereoisomer thereof of the present disclosure.

The term "subject" (or "patient") as used herein includes all members of the animal kingdom prone to or suffering from the indicated disease or disorder. In some embodiments, the subject is a mammal, e.g., a human or a non-human mammal. The methods are also applicable to companion animals such as dogs and cats as well as livestock such as cows, horses, sheep, goats, pigs, and other domesticated and wild animals. A subject "in need of" treatment according to the present disclosure may be "suffering from or suspected of suffering from" a specific disease or disorder may have been positively diagnosed or otherwise presents with a sufficient number of risk factors or a sufficient number or combination of signs or symptoms such that a medical professional could diagnose or suspect that the subject was suffering from the disease or disorder. Thus, subjects suffering from a specific disease or disorder, and subjects suspected of suffering from a specific disease or disorder are not necessarily two distinct groups.

In some embodiments, the bifunctional compounds may be useful in the treatment of cell proliferative diseases and disorders (e.g., cancer or benign neoplasms). As used herein, the term "cell proliferative disease or disorder" refers to the conditions characterized by aberrant cell growth, or both, including noncancerous conditions such as neoplasms, precancerous conditions, benign tumors, and cancer.

In some embodiments, the methods are directed to treating subjects having cancer. Both adult tumors/cancers and pediatric tumors/cancers are included. The cancers may be vascularized, or not yet substantially vascularized, or non-vascularized tumors.

In some embodiments, methods of the present disclosure entail treatment of subjects having cell proliferative diseases or disorders of the hematological system.

As used herein, "cell proliferative diseases or disorders of the hematological system" include lymphoma, leukemia, myeloid neoplasms, mast cell neoplasms, myelodysplasia, benign monoclonal gammopathy, lymphomatoid papulosis, polycythemia vera, chronic myelocytic leukemia, agnogenic myeloid metaplasia, and essential thrombocythemia. Representative examples of hematologic cancers may thus include multiple myeloma, lymphoma (including T-cell lymphoma, Hodgkin's lymphoma, non-Hodgkin's lymphoma (diffuse large B-cell lymphoma (DLBCL), follicular lymphoma (FL), mantle cell lymphoma (MCL) and ALK+ anaplastic large cell lymphoma (e.g., B-cell non-Hodgkin's lymphoma selected from diffuse large B-cell lymphoma (e.g., germinal center B-cell-like diffuse large B-cell lymphoma or activated B-cell-like diffuse large B-cell lymphoma), Burkitt's lymphoma/leukemia, mantle cell lymphoma, mediastinal (thymic) large B-cell lymphoma, follicular lymphoma, marginal zone lymphoma, lymphoplasmacytic lymphoma/Waldenstrom macroglobulinemia, metastatic pancreatic adenocarcinoma, refractory B-cell non-Hodgkin's lymphoma, and relapsed B-cell non-Hodgkin's lymphoma, childhood lymphomas, and lymphomas of lymphocytic and cutaneous origin, e.g., small lymphocytic lymphoma, leukemia, including childhood leukemia, hairy-cell leukemia, acute lymphocytic leukemia, acute myelocytic leukemia, acute myeloid leukemia (e.g., acute monocytic leukemia), chronic lymphocytic leukemia, small lymphocytic leukemia, chronic myelocytic leukemia, chronic myelogenous leukemia, and mast cell leukemia, myeloid neoplasms and mast cell neoplasms.

In some embodiments, the methods are directed to treating subjects having a lymphoid malignancy. In some embodiments, the lymphoid malignancy is peripheral T-cell lymphoma (PTCL), diffuse large B-cell lymphoma (DLBCL), mantle cell lymphoma (MCL), follicular lymphoma (FL), chronic lymphocytic leukemia (CLL), acute lymphoblastic leukemia/lymphoma (ALL), cutaneous T-cell lymphoma, chronic myeloid leukemia, or B-cell non-Hodgkin's lymphoma. In some embodiments, the cancer is melanoma, breast cancer or non-small cell lung cancer.

Bifunctional compounds of formula (I) may be administered to a patient, e.g., a cancer patient, as a monotherapy or by way of combination therapy. Therapy may be "front/first-line", i.e., as an initial treatment in patients who have undergone no prior anti-cancer treatment regimens, either alone or in combination with other treatments; or "second-line", as a treatment in patients who have undergone a prior anti-cancer treatment regimen, either alone or in combination with other treatments; or as "third-line", "fourth-line", etc. treatments, either alone or in combination with other treatments. Therapy may also be given to patients who have had previous treatments which were unsuccessful or partially successful but who became unresponsive or intolerant to the particular treatment. Therapy may also be given as an adjuvant treatment, i.e., to prevent reoccurrence of cancer in patients with no currently detectable disease or after surgical removal of a tumor. Thus, in some embodiments, the compounds may be administered to a patient who has received another therapy, such as chemotherapy, radioimmunotherapy, surgical therapy, immunotherapy, radiation therapy, targeted therapy or any combination thereof.

The methods of the present disclosure may entail administration of a bifunctional compound of formula (I) or a pharmaceutical composition thereof to the patient in a single dose or in multiple doses (e.g., 1, 2, 3, 4, 5, 6, 7, 8, 10, 15, 20, or more doses). For example, the frequency of administration may range from once a day up to about once every eight weeks. In some embodiments, the frequency of administration ranges from about once a day for 1, 2, 3, 4, 5, or 6 weeks, and in other embodiments entails at least one 28-day cycle which includes daily administration for 3 weeks (21 days) followed by a 7-day "off" period. In other embodiments, the compound may be dosed twice a day (BID) over the course of two and a half days (for a total of 5 doses) or once a day (QD) over the course of two days (for a total of 2 doses). In other embodiments, the compound may be dosed once a day (QD) over the course of 5 days.

Combination Therapy

The bifunctional compounds of formula (I) and their pharmaceutically acceptable salts and stereoisomers may be used in combination or concurrently with at least one other active agent, e.g., anti-cancer agent or regimen, in treating diseases and disorders. The terms "in combination" and "concurrently" in this context mean that the agents are co-administered, which includes substantially contemporaneous administration, by way of the same or separate dosage forms, and by the same or different modes of administration, or sequentially, e.g., as part of the same treatment regimen, or by way of successive treatment regimens. Thus, if given sequentially, at the onset of administration of the second compound, the first of the two compounds is in some cases still detectable at effective concentrations at the site of treatment. The sequence and time interval may be determined such that they can act together (e.g., synergistically) to provide an increased benefit than if they were administered otherwise. For example, the therapeutics may be administered at the same time or sequentially in any order at different points in time; however, if not administered at the same time, they may be administered sufficiently close in time so as to provide the desired therapeutic effect, which may be in a synergistic fashion. Thus, the terms are not limited to the administration of the active agents at exactly the same time.

In some embodiments, the treatment regimen may include administration of a bifunctional compound of formula (I) in combination with one or more additional therapeutics known for use in treating a disease or condition (e.g., cancer). The dosage of the additional therapeutic may be the same or even lower than known or recommended doses. See, Hardman et al., eds., *Goodman & Gilman's the Pharmacological Basis of Basis of Therapeutics,* 10th ed., McGraw-Hill, New York, 2001*; Physician's Desk Reference* 60*th ed.,* 2006. For example, anti-cancer agents that may be suitable for use in combination with the bifunctional compounds are known in the art. See, e.g., U.S. Pat. No. 9,101,622 (Section 5.2 thereof) and U.S. Pat. No. 9,345,705 B2 (Columns 12-18 thereof). Representative examples of additional anti-cancer agents and treatment regimens include radiation therapy, chemotherapeutics (e.g., mitotic inhibitors, angiogenesis inhibitors, anti-hormones, autophagy inhibitors, alkylating agents, intercalating antibiotics, growth factor inhibitors, anti-androgens, signal transduction pathway inhibitors, anti-microtubule agents, platinum coordination complexes, HDAC inhibitors, proteasome inhibitors, and topoisomerase inhibitors), immunomodulators, therapeutic antibodies (e.g., mono-specific and bispecific antibodies) and CAR-T therapy.

In some embodiments, a bifunctional compound of formula (I) and the additional (e.g., anticancer) therapeutic may be administered less than 5 minutes apart, less than 30 minutes apart, less than 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. The two or more (e.g., anticancer) therapeutics may be administered within the same patient visit.

When the active components of the combination are not administered in the same pharmaceutical composition, it is understood that they can be administered in any order to a subject in need thereof. For example, a bifunctional compound of the present disclosure can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of the additional therapeutic, to a subject in need thereof. In various aspects, the therapeutics are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one example, the (e.g., anticancer) therapeutics are administered within the same office visit. In another example, the combination anticancer therapeutics may be administered at 1 minute to 24 hours apart.

In some embodiments involving cancer treatment, a bifunctional compound of formula (I) and the additional anti-cancer agent or therapeutic are cyclically administered. Cycling therapy involves the administration of one anticancer therapeutic for a period of time, followed by the administration of a second anti-cancer therapeutic for a period of time and repeating this sequential administration, i.e., the cycle, in order to reduce the development of resistance to one or both of the anticancer therapeutics, to avoid or reduce the side effects of one or both of the anticancer therapeutics, and/or to improve the efficacy of the therapies. In one example, cycling therapy involves the administration of a first anticancer therapeutic for a period of time, followed by the administration of a second anticancer therapeutic for a period of time, optionally, followed by the administration of a third anticancer therapeutic for a period of time and so forth, and repeating this sequential administration, i.e., the cycle in order to reduce the development of resistance to one of the anticancer therapeutics, to avoid or reduce the side effects of one of the anticancer therapeutics, and/or to improve the efficacy of the anticancer therapeutics.

In some embodiments, the bifunctional compound of the present disclosure may be used in combination with other anti-cancer agents, examples of which include Etoposide (e.g., lymphomas, and non-lymphocytic leukemia), Vincristine (e.g., leukemia), Daunorubicin (e.g., acute myeloid leukemia (AML), acute lymphocytic leukemia (ALL), chronic myelogenous leukemia (CML), and Kaposi's sarcoma), Rituximab (e.g., non-Hodgkin's lymphoma), Alemtuzumab (e.g., chronic lymphocytic leukemia (CLL), cutaneous T-cell lymphoma (CTCL) and T-cell lymphoma), Bortezomib (e.g., multiple myeloma and mantle cell lymphoma), Pegaspargase (e.g., acute lymphoblastic leukemia), Keytruda (e.g., Hodgkin lymphoma), and dexamethasone (e.g., acute multiple myeloma).

In some embodiments, the bifunctional compound of the present disclosure may be co-administered with a therapeutically effective amount of an immunotherapy and/or chemotherapy. In some embodiments, the immunotherapy is a checkpoint inhibitor, a cell-cycle inhibitor, or a targeted therapy. In some embodiments, the checkpoint inhibitor is anti-PD-1 or anti-PD-L1. In some embodiments, the cell-cycle inhibitor is palbociclib, ribociclib, or abemaciclib. In some embodiments, the targeted therapy is a kinase inhibitor.

Pharmaceutical Kits

The present compositions may be assembled into kits or pharmaceutical systems. Kits or pharmaceutical systems according to this aspect of the disclosure include a carrier or package such as a box, carton, tube or the like, having in close confinement therein one or more containers, such as vials, tubes, ampoules, or bottles, which contain a bifunctional compound of the present disclosure or a pharmaceutical composition which contains the compound and a pharmaceutically acceptable carrier wherein the compound and the carrier may be disposed in the same or separate containers. The kits or pharmaceutical systems of the disclosure may also include printed instructions for using the compounds and compositions.

These and other aspects of the present disclosure will be further appreciated upon consideration of the following Examples, which are intended to illustrate certain particular embodiments of the disclosure but are not intended to limit its scope, as defined by the claims.

EXAMPLES

Example 1: Synthesis of (2-amino-4-(trifluoromethoxy)phenyl)(4-(7-(piperazin-1-yl)quinazolin-4-yl)piperidin-1-yl)methanone (Intermediate 5)

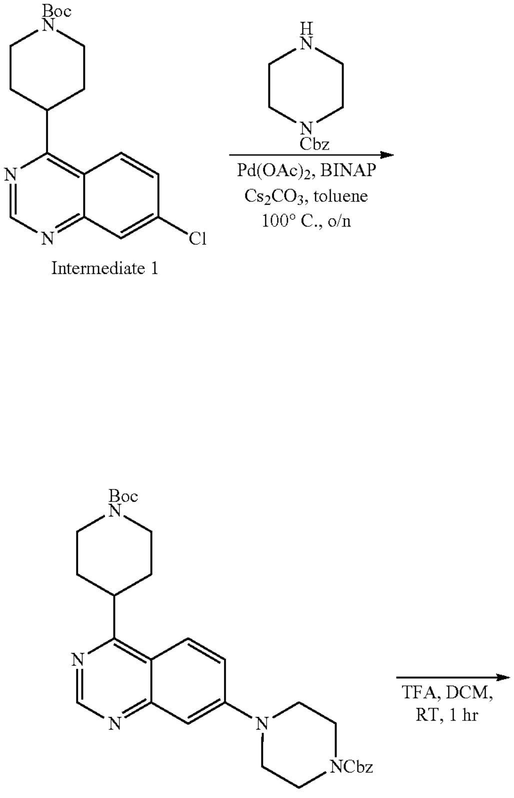

Intermediate 1

Intermediate 2

-continued

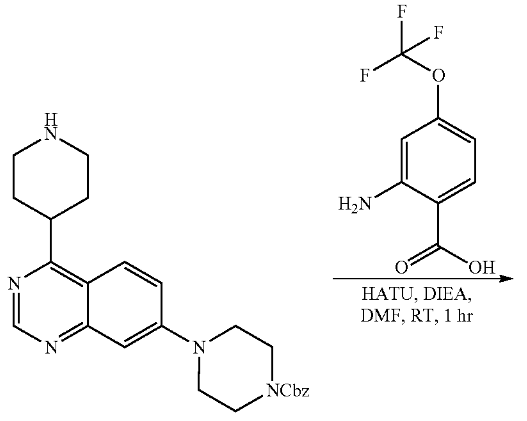

Intermediate 3

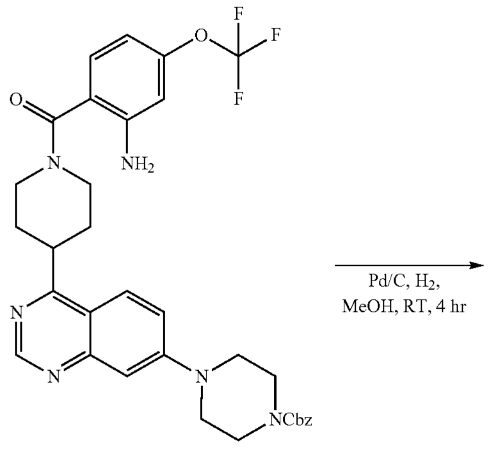

Intermediate 4

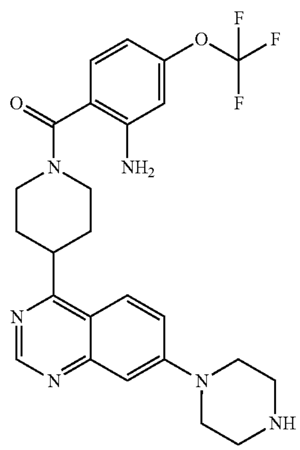

Intermediate 5

Step 1: Synthesis of benzyl 4-(4-(1-(tert-butoxycarbonyl) piperidin-4-yl)quinazolin-7-yl)piperazine-1-carboxylate (Intermediate 2): To toluene (12 mL) was added tert-butyl 4-(7-chloroquinazolin-4-yl)piperidine-1-carboxylate (389 mg, 1.12 mmol), benzyl piperazine-1-carboxylate (370 mg, 1.68 mmol), palladium (II) acetate (25 mg, 0.11 mmol), ([1,1'-Binaphthalene]-2,2'-diyl)bis(diphenylphosphine (BINAP)) (140 mg, 0.22 mmol), and cesium carbonate (1.1 g, 3.36 mmol). The reaction mixture was flushed with nitrogen for 20 minutes, and stirred at 100° C. overnight (o/n). Next day, the reaction mixture was filtered over Celite, washed with saturated sodium bicarbonate (aq.), and extracted with dichloromethane (DCM) (10 mL×3). The organic layer was concentrated in vacuo and purified by column chromatography on silica gel (0-100% ethyl acetate (EA)/DCM) to obtain benzyl 4-(4-(1-(tert-butoxycarbonyl)piperidin-4-yl) quinazolin-7-yl)piperazine-1-carboxylate (Intermediate 2) as a black oil (507 mg, 85% yield). MS m/z 532.31 $[M+H]^+$.

Step 2: Synthesis of benzyl 4-(4-(piperidin-4-yl)quinazolin-7-yl)piperazine-1-carboxylate (Intermediate 3): To Intermediate 2 (507 mg, 0.95 mmol) was added 6 mL of DCM and 2 mL of trifluoroacetic acid (TFA). The reaction mixture was stirred for 1 hour at room temperature. The reaction mixture was concentrated in vacuo to obtain crude benzyl 4-(4-(piperidin-4-yl)quinazolin-7-yl)piperazine-1-carboxylate (Intermediate 3) as the trifluoroacetic salt. Quantitative yield. MS m/z 432.27 $[M+H]^+$.

Step 3: Synthesis of benzyl 4-(4-(1-(2-amino-4-(trifluoromethoxy)benzoyl)piperidin-4-yl)quinazolin-7-yl)piperazine-1-carboxylate (Intermediate 4): To Intermediate 3 (490 mg, 0.9 mmol) was added 2-amino-4-(trifluoromethoxy) benzoic acid (200 mg, 0.9 mmol), 1-[bis(dimethylamino) methylene]-1H-1,2,3-triazolo[4,5-b]pyridinium 3-oxide hexafluorophosphate (HATU) (342 mg, 0.9 mmol), N,N-diisopropylethylamine (DIEA) (1.6 mL, 9 mmol), and dimethylformamide (DMF) (10 mL). The reaction was stirred at room temperature for 1 hour. The reaction mixture was diluted with ethyl acetate and washed with brine (15 mL×4). The organic layer was collected, dried with anhydrous sodium sulfate, and concentrated in vacuo. The crude residue was purified by column chromatography on silica gel (0-20% MeOH/DCM) to obtain benzyl 4-(4-(1-(2-amino-4-(trifluoromethoxy)benzoyl)piperidin-4-yl)quinazolin-7-yl) piperazine-1-carboxylate (Intermediate 4) as a black oil (495 mg, 87% yield). MS m/z 635.32 $[M+H]^+$.

Step 4: Synthesis of (2-amino-4-(trifluoromethoxy)phenyl)(4-(7-(piperazin-1-yl)quinazolin-4-yl)piperidin-1-yl) methanone (Intermediate 5): To Intermediate 4 (495 mg, 0.78 mmol) was added Pd/C (50 mg) and MeOH (15 mL). $H_2$ (g) was introduced to the reaction mixture, which was stirred at room temperature for 4 hours. The reaction mixture was filtered over Celite, concentrated in vacuo to obtain crude (2-amino-4-(trifluoromethoxy)phenyl)(4-(7-(piperazin-1-yl)quinazolin-4-yl)piperidin-1-yl)methanone (Intermediate 5) as a black oil. MS m/z 501.23 $[M+H]^+$.

Example 2: Synthesis of (2S,4R)-1-((S)-2-(3-(4-(4-(1-(2-amino-4-(trifluoromethoxy)benzoyl)piperidin-4-yl)quinazolin-7-yl)piperazin-1-yl)propanamido)-3,3-dimethylbutanoyl)-4-hydroxy-N—((S)-1-(4-(4-methylthiazol-5-yl)phenyl)ethyl)pyrrolidine-2-carboxamide (1)
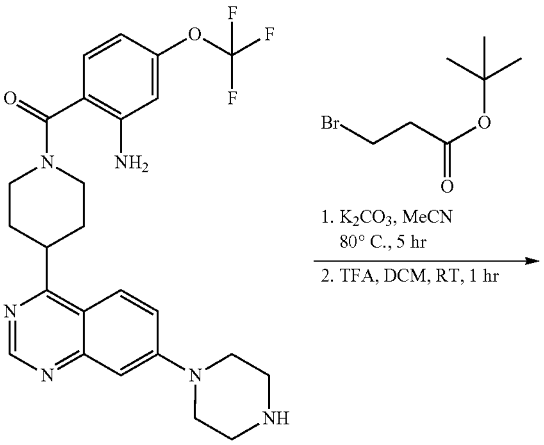
Intermediate 5
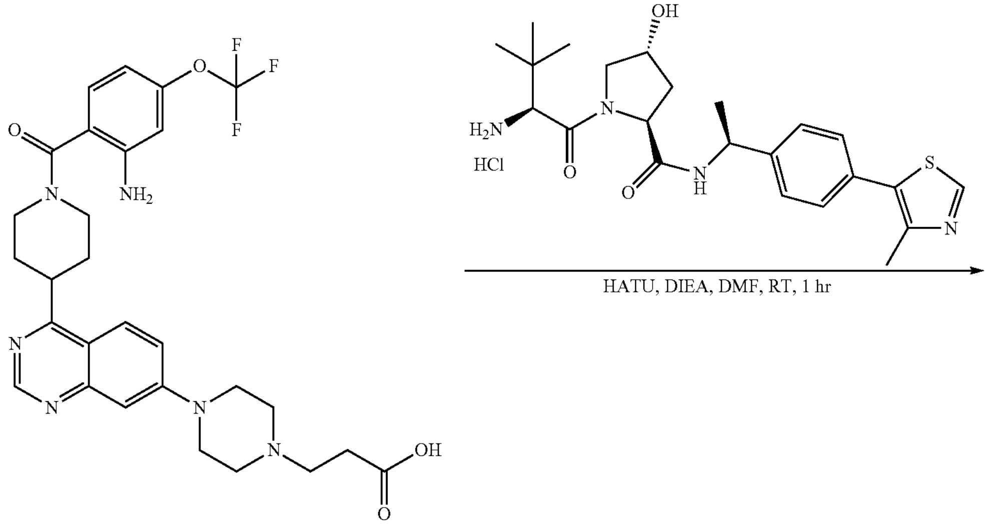

-continued

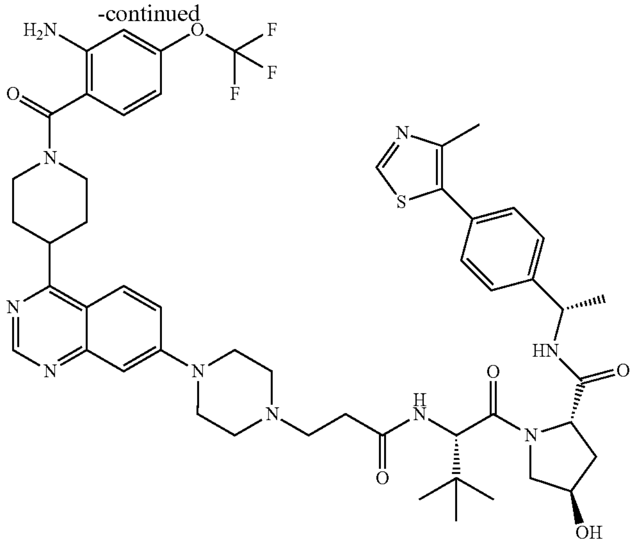

1

Step 1: Synthesis of 3-(4-(4-(1-(2-amino-4-(trifluoromethoxy)benzoyl)piperidin-4-yl)quinazolin-7-yl)piperazin-1-yl)propanoic acid: To Intermediate 5 (27 mg, 0.054 mmol) was added tert-butyl 3-bromopropanoate (23 mg, 0.11 mmol), potassium carbonate (30 mg, 0.22 mmol), and acetonitrile (1 mL). The reaction mixture was stirred at 80° C. for 5 hours. Subsequently, the reaction mixture was concentrated in vacuo and purified by column chromatography on silica gel (0-20% MeOH/DCM) to obtain tert-butyl 3-(4-(4-(1-(2-amino-4-(trifluoromethoxy)benzoyl)piperidin-4-yl)quinazolin-7-yl)piperazin-1-yl)propanoate (20 mg, 51% yield) as a tan solid. MS m/z 629.35 $[M+H]^+$.

Step 2: Synthesis of 3-(4-(4-(1-(2-amino-4-(trifluoromethoxy)benzoyl)piperidin-4-yl)quinazolin-7-yl)piperazin-1-yl)propanoic acid: To tert-butyl 3-(4-(4-(1-(2-amino-4-(trifluoromethoxy)benzoyl)piperidin-4-yl)quinazolin-7-yl)piperazin-1-yl)propanoate (20 mg, 0.03 mmol) was added 750 μL of DCM and 250 μL of TFA. The reaction mixture was stirred at room temperature for 1 hour and concentrated in vacuo to obtain crude 3-(4-(4-(1-(2-amino-4-(trifluoromethoxy)benzoyl)piperidin-4-yl)quinazolin-7-yl)piperazin-1-yl)propanoic acid (quantitative yield). MS m/z 573.27 $[M+H]^+$.

Step 3: Synthesis of (2S,4R)-1-((S)-2-(3-(4-(4-(1-(2-amino-4-(trifluoromethoxy)benzoyl)piperidin-4-yl)quinazolin-7-yl)piperazin-1-yl)propanamido)-3,3-dimethylbutanoyl)-4-hydroxy-N—((S)-1-(4-(4-methylthiazol-5-yl)phenyl)ethyl)pyrrolidine-2-carboxamide (1): To 3-(4-(4-(1-(2-amino-4-(trifluoromethoxy)benzoyl)piperidin-4-yl)quinazolin-7-yl)piperazin-1-yl)propanoic acid (18 mg, 0.032 mmol) was added (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide hydrochloride (15 mg, 0.032 mmol), HATU (12 mg, 0.032 mmol), DIEA (30 μL, 0.16 mmol), and DMF (1 mL). The reaction mixture was stirred at room temperature for 1 hour. The reaction was purified by reverse phase HPLC (10-70% MeOH in $H_2O$) to obtain (2S,4R)-1-((S)-2-(3-(4-(4-(1-(2-amino-4-(trifluoromethoxy)benzoyl)piperidin-4-yl)quinazolin-7-yl)piperazin-1-yl)propanamido)-3,3-dimethylbutanoyl)-4-hydroxy-N—((S)-1-(4-(4-methylthiazol-5-yl)phenyl)ethyl)pyrrolidine-2-carboxamide (1) as a yellow solid (15 mg, 38% yield). $^1H$ NMR (500 MHz, DMSO-$d_6$) δ 9.85 (s, 1H), 9.04 (s, 1H), 9.00 (s, 1H), 8.39 (d, J=7.8 Hz, 1H), 8.34 (d, J=9.5 Hz, 1H), 8.28 (d, J=9.2 Hz, 1H), 7.62 (dd, J=9.4, 2.5 Hz, 1H), 7.45 (d, J=8.0 Hz, 2H), 7.39 (d, J=8.0 Hz, 2H), 7.36-7.30 (m, 1H), 7.28 (d, J=2.4 Hz, 1H), 7.14 (d, J=8.4 Hz, 1H), 6.68 (d, J=2.2 Hz, 1H), 6.51 (d, J=8.5 Hz, 1H), 4.93 (p, J=7.0 Hz, 1H), 4.56 (d, J=9.2 Hz, 1H), 4.43 (t, J=8.0 Hz, 1H), 4.29 (d, J=19.0 Hz, 3H), 3.96 (d, J=10.9 Hz, 2H), 3.68-3.54 (m, 4H), 3.43 (t, J=7.4 Hz, 2H), 3.22 (s, 7H), 2.79 (dq, J=22.6, 8.1 Hz, 2H), 2.46 (s, 3H), 2.05 (dd, J=21.1, 9.7 Hz, 1H), 1.90-1.77 (m, 5H), 1.39 (d, J=6.9 Hz, 3H), 0.96 (s, 9H). MS m/z 999.50 $[M+H]^+$.

Example 3: Synthesis of (2S,4R)-1-((S)-2-(6-(4-(4-(1-(2-amino-4-(trifluoromethoxy)benzoyl)piperidin-4-yl)quinazolin-7-yl)piperazin-1-yl)hexanamido)-3,3-dimethylbutanoyl)-4-hydroxy-N—((S)-1-(4-(4-methylthiazol-5-yl)phenyl)ethyl)pyrrolidine-2-carboxamide (2)

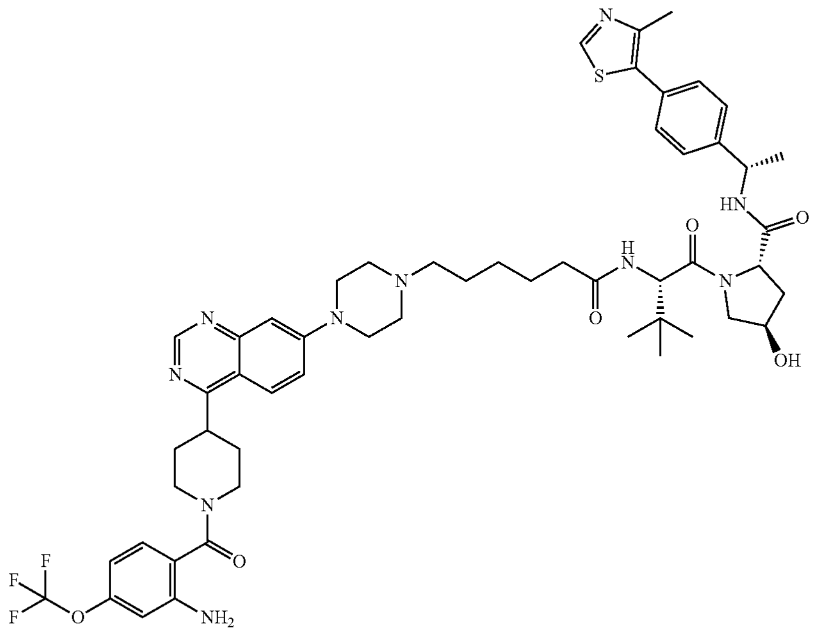 [SMILES: Cc1ncsc1-c1ccc([C@H](C)NC(=O)[C@@H]2C[C@@H](O)CN2C(=O)[C@@H](NC(=O)CCCCCN2CCN(c3ccc4c(C5CCN(C(=O)c6ccc(OC(F)(F)F)cc6N)CC5)ncnc4c3)CC2)C(C)(C)C)cc1]

Following the general procedure used for compound 1, tert-butyl 6-bromohexanoate was used to synthesize (2S,4R)-1-((S)-2-(6-(4-(4-(1-(2-amino-4-(trifluoromethoxy)benzoyl)piperidin-4-yl)quinazolin-7-yl)piperazin-1-yl)hexanamido)-3,3-dimethylbutanoyl)-4-hydroxy-N—((S)-1-(4-(4-methylthiazol-5-yl)phenyl)ethyl)pyrrolidine-2-carboxamide (2) as a yellow solid. $^1$H NMR (500 MHz, DMSO-$d_6$) δ 11.40 (s, 1H), 9.10 (s, 1H), 9.02 (s, 1H), 8.46 (d, J=9.6 Hz, 1H), 8.41 (d, J=7.8 Hz, 1H), 7.83 (d, J=9.3 Hz, 1H), 7.71 (dd, J=9.8, 2.5 Hz, 1H), 7.45-7.42 (m, 2H), 7.41-7.38 (m, 2H), 7.32 (d, J=2.4 Hz, 1H), 7.17 (d, J=8.4 Hz, 1H), 6.69 (dd, J=2.4, 1.1 Hz, 1H), 6.51 (ddd, J=8.4, 2.4, 1.2 Hz, 1H), 4.94-4.90 (m, 1H), 4.53 (d, J=9.3 Hz, 2H), 4.44 (d, J=8.1 Hz, 1H), 4.36-4.27 (m, 4H), 4.06 (t, J=11.7 Hz, 2H), 3.65-3.54 (m, 6H), 3.11 (td, J=12.9, 7.6 Hz, 5H), 2.46 (s, 3H), 2.29 (dt, J=14.6, 7.5 Hz, 1H), 2.18 (dt, J=14.4, 7.2 Hz, 1H), 2.06-2.00 (m, 1H), 2.00-1.92 (m, 2H), 1.88-1.82 (m, 2H), 1.82-1.73 (m, 3H), 1.61-1.47 (m, 3H), 1.38 (d, J=7.0 Hz, 3H), 1.29 (p, J=7.6 Hz, 2H), 0.95 (s, 9H). MS m/z 1041.65 $[M+H]^+$.

Example 4: Synthesis of (2S,4R)-1-((S)-2-(9-(4-(4-(1-(2-amino-4-(trifluoromethoxy)benzoyl)piperidin-4-yl)quinazolin-7-yl)piperazin-1-yl)nonanamido)-3,3-dimethylbutanoyl)-4-hydroxy-N—((S)-1-(4-(4-methylthiazol-5-yl)phenyl)ethyl)pyrrolidine-2-carboxamide (3)

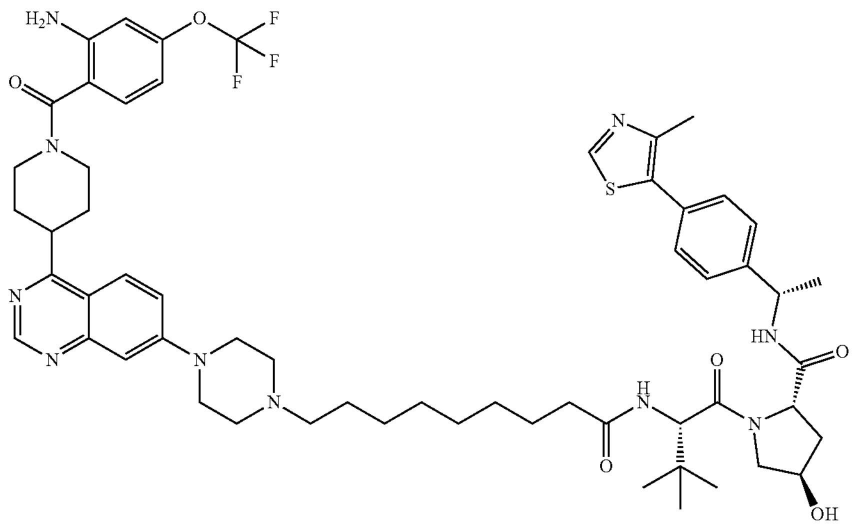 [SMILES: Cc1ncsc1-c1ccc([C@H](C)NC(=O)[C@@H]2C[C@@H](O)CN2C(=O)[C@@H](NC(=O)CCCCCCCCN2CCN(c3ccc4c(C5CCN(C(=O)c6ccc(OC(F)(F)F)cc6N)CC5)ncnc4c3)CC2)C(C)(C)C)cc1]

Following the general procedure used for compound 1, tert-butyl 9-bromononanoate was used to synthesize (2S,4R)-1-((S)-2-(9-(4-(4-(1-(2-amino-4-(trifluoromethoxy)benzoyl)piperidin-4-yl)quinazolin-7-yl)piperazin-1-yl)nonanamido)-3,3-dimethylbutanoyl)-4-hydroxy-N—((S)-1-(4-(4-methylthiazol-5-yl)phenyl)ethyl)pyrrolidine-2-carboxamide (3) as a yellow solid. $^1$H NMR (500 MHz, DMSO-$d_6$) δ 9.59 (s, 1H), 9.09 (s, 1H), 9.02 (s, 1H), 8.43 (d, J=9.7 Hz, 1H), 8.36 (d, J=7.8 Hz, 1H), 7.79 (d, J=9.3 Hz, 1H), 7.68 (dd, J=9.6, 2.5 Hz, 1H), 7.50-7.42 (m, 2H), 7.42-7.35 (m, 2H), 7.27 (d, J=2.4 Hz, 1H), 7.15 (d, J=8.4 Hz, 1H), 6.68 (d, J=2.3 Hz, 1H), 6.52 (dd, J=8.4, 2.3 Hz, 1H), 4.94-4.91 (m, 1H), 4.53 (d, J=9.4 Hz, 1H), 4.42 (t, J=8.0 Hz, 1H), 4.35-4.29 (m, 3H), 4.02 (s, 1H), 3.63 (td, J=11.7, 7.5 Hz, 3H), 3.33 (t, J=12.8 Hz, 2H), 3.17 (s, 6H), 2.46 (s, 3H), 2.28 (dd, J=14.7, 7.4 Hz, 1H), 2.15-2.09 (m, 1H), 2.01 (d, J=9.2 Hz, 1H), 1.90-1.84 (m, 3H), 1.80 (ddd, J=12.9, 8.6, 4.7 Hz, 2H), 1.68 (s, 2H), 1.54-1.46 (m, 3H), 1.38 (d, J=7.0 Hz, 2H), 1.34-1.23 (m, 11H), 0.94 (s, 9H). MS m/z 1083.61 $[M+H]^+$.

Example 5: Synthesis of (2S,4R)-1-((S)-2-(3-(2-(4-(4-(1-(2-amino-4-(trifluoromethoxy)benzoyl)piperidin-4-yl)quinazolin-7-yl)piperazin-1-yl)ethoxy)propanamido)-3,3-dimethylbutanoyl)-4-hydroxy-N—((S)-1-(4-(4-methylthiazol-5-yl)phenyl)ethyl) pyrrolidine-2-carboxamide (4)

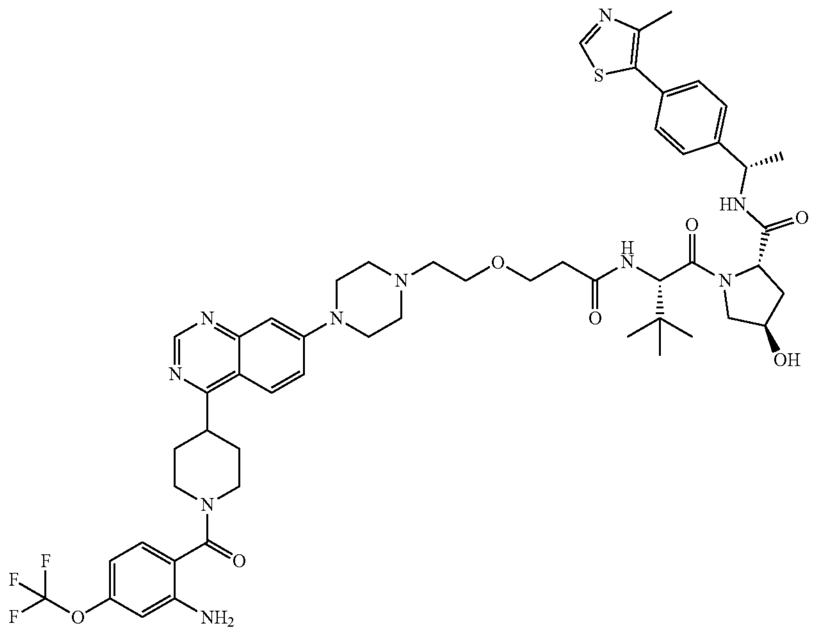 [SMILES: Cc1ncsc1-c1ccc([C@H](C)NC(=O)[C@@H]2C[C@@H](O)CN2C(=O)[C@@H](NC(=O)CCOCCN2CCN(c3ccc4c(C5CCN(C(=O)c6ccc(OC(F)(F)F)cc6N)CC5)ncnc4c3)CC2)C(C)(C)C)cc1]

Following the general procedure used for compound 1, tert-butyl 3-(2-bromoethoxy)propanoate was used to synthesize (2S,4R)-1-((S)-2-(3-(2-(4-(4-(1-(2-amino-4-(trifluoromethoxy)benzoyl)piperidin-4-yl)quinazolin-7-yl)piperazin-1-yl)ethoxy)propanamido)-3,3-dimethylbutanoyl)-4-hydroxy-N—((S)-1-(4-(4-methylthiazol-5-yl)phenyl)ethyl) pyrrolidine-2-carboxamide (4) as a yellow solid. MS m/z 1043.54 $[M+H]^+$.

Example 6: Synthesis of (2S,4R)-1-((S)-2-(3-(2-(2-(4-(4-(1-(2-amino-4-(trifluoromethoxy)benzoyl)piperidin-4-yl)quinazolin-7-yl)piperazin-1-yl)ethoxy) ethoxy)propanamido)-3,3-dimethylbutanoyl)-4-hydroxy-N—((S)-1-(4-(4-methylthiazol-5-yl)phenyl) ethyl)pyrrolidine-2-carboxamide (5)

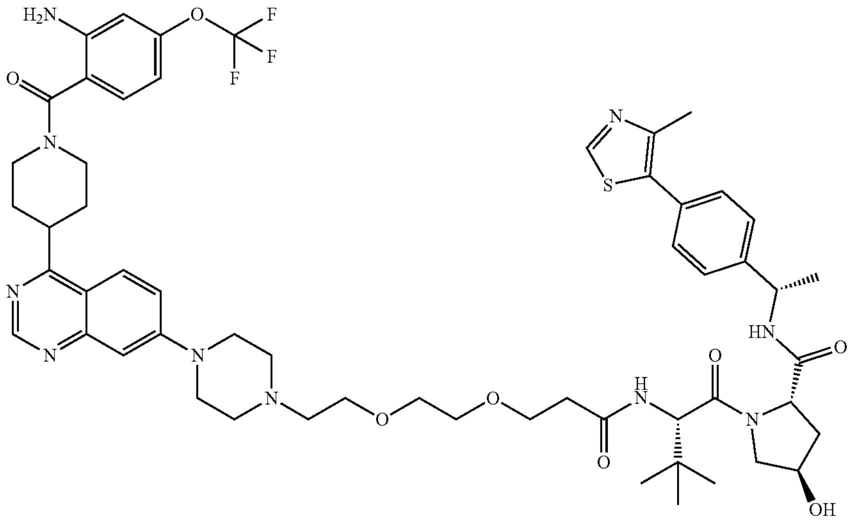 [SMILES: Cc1ncsc1-c1ccc([C@H](C)NC(=O)[C@@H]2C[C@@H](O)CN2C(=O)[C@@H](NC(=O)CCOCCOCCN2CCN(c3ccc4c(C5CCN(C(=O)c6ccc(OC(F)(F)F)cc6N)CC5)ncnc4c3)CC2)C(C)(C)C)cc1]

Following the general procedure used for compound 1, tert-butyl 3-(2-(2-bromoethoxy)ethoxy)propanoate was used to synthesize (2S,4R)-1-((S)-2-(3-(2-(2-(4-(4-(1-(2-amino-4-(trifluoromethoxy)benzoyl)piperidin-4-yl)quinazolin-7-yl)piperazin-1-yl)ethoxy)ethoxy)propanamido)-3,3-dimethylbutanoyl)-4-hydroxy-N—((S)-1-(4-(4-methylthiazol-5-yl)phenyl)ethyl)pyrrolidine-2-carboxamide (5) as a yellow solid. $^1$H NMR (500 MHz, DMSO-$d_6$) δ 9.92 (s, 1H), 9.04 (s, 1H), 9.00 (s, 1H), 8.35 (dd, J=14.6, 8.7 Hz, 2H), 7.89 (d, J=9.4 Hz, 1H), 7.62 (dd, J=9.5, 2.6 Hz, 1H), 7.45-7.42 (m, 2H), 7.38 (d, J=8.4 Hz, 2H), 7.28 (d, J=2.6 Hz, 1H), 7.14 (d, J=8.3 Hz, 1H), 6.68 (dd, J=2.4, 1.1 Hz, 1H), 6.51 (ddd, J=8.4, 2.5, 1.2 Hz, 1H), 4.93 (q, J=7.1 Hz, 1H), 4.56 (d, J=9.3 Hz, 1H), 4.43 (t, J=8.1 Hz, 1H), 4.32-4.23 (m, 3H), 3.98-3.90 (m, 1H), 3.83-3.77 (m, 2H), 3.70-3.51 (m, 10H), 3.41 (t, J=4.9 Hz, 2H), 3.34 (s, 2H), 3.30-3.14 (m, 4H), 2.58-2.53 (m, 1H), 2.46 (s, 3H), 2.39 (dd, J=14.7, 6.1 Hz, 1H), 2.08-2.00 (m, 1H), 1.94-1.74 (m, 5H), 1.37 (d, J=7.0 Hz, 3H), 1.29-1.22 (m, 1H), 0.94 (s, 9H). MS m/z 1087.59 [M+H]$^+$.

Example 7: Synthesis of (2S,4R)-1-((S)-1-(4-(4-(1-(2-amino-4-(trifluoromethoxy)benzoyl)piperidin-4-yl)quinazolin-7-yl)piperazin-1-yl)-14-(tert-butyl)-12-oxo-3,6,9-trioxa-13-azapentadecan-15-oyl)-4-hydroxy-N—((S)-1-(4-(4-methylthiazol-5-yl)phenyl)ethyl)pyrrolidine-2-carboxamide (6)

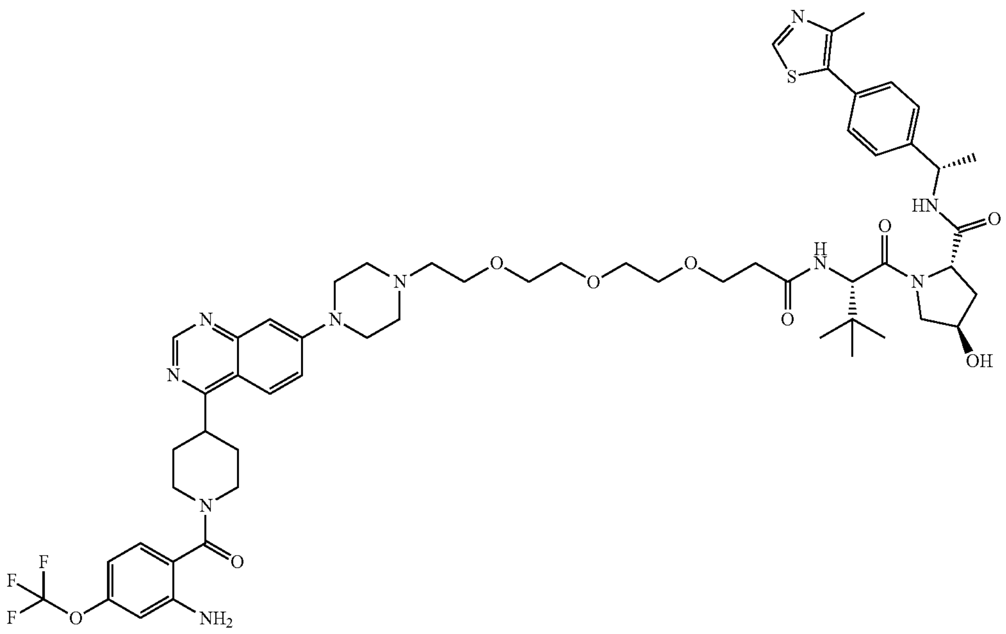 [SMILES: Cc1ncsc1-c1ccc([C@H](C)NC(=O)[C@@H]2C[C@@H](O)CN2C(=O)[C@@H](NC(=O)CCOCCOCCOCCN2CCN(c3ccc4c(C5CCN(C(=O)c6ccc(OC(F)(F)F)cc6N)CC5)ncnc4c3)CC2)C(C)(C)C)cc1]

Following the general procedure used for compound 1, tert-butyl 3-(2-(2-(2-bromoethoxy)ethoxy)ethoxy)propanoate was used to synthesize (2S,4R)-1-((S)-1-(4-(4-(1-(2-amino-4-(trifluoromethoxy)benzoyl)piperidin-4-yl)quinazolin-7-yl)piperazin-1-yl)-14-(tert-butyl)-12-oxo-3,6,9-trioxa-13-azapentadecan-15-oyl)-4-hydroxy-N—((S)-1-(4-(4-methylthiazol-5-yl)phenyl)ethyl)pyrrolidine-2-carboxamide (6) as a yellow solid. $^1$H NMR (500 MHz, DMSO-$d_6$) δ 9.93 (s, 1H), 9.02 (d, J=20.4 Hz, 2H), 8.36 (dd, J=15.9, 8.7 Hz, 2H), 7.87 (d, J=9.3 Hz, 1H), 7.62 (dd, J=9.5, 2.6 Hz, 1H), 7.47-7.42 (m, 2H), 7.38 (d, J=8.4 Hz, 2H), 7.28 (d, J=2.6 Hz, 1H), 7.14 (d, J=8.4 Hz, 1H), 6.68 (dd, J=2.4, 1.2 Hz, 1H), 6.51 (ddd, J=8.4, 2.4, 1.2 Hz, 1H), 4.92 (p, J=7.1 Hz, 1H), 4.54 (d, J=9.4 Hz, 1H), 4.42 (t, J=8.0 Hz, 1H), 4.31-4.23 (m, 3H), 3.94 (dt, J=12.1, 6.1 Hz, 1H), 3.81 (t, J=5.0 Hz, 2H), 3.61 (dtt, J=16.5, 6.6, 3.3 Hz, 10H), 3.55-3.47 (m, 5H), 3.42 (d, J=6.4 Hz, 2H), 3.34 (t, J=12.9 Hz, 2H), 3.16 (d, J=19.2 Hz, 5H), 2.60-2.53 (m, 1H), 2.46 (s, 3H), 2.36 (dt, J=14.7, 6.1 Hz, 2H), 2.02 (t, J=10.8 Hz, 1H), 1.92-1.76 (m, 5H), 1.38 (d, J=7.0 Hz, 3H), 0.93 (s, 9H). MS m/z 1131.56 [M+H]$^+$.

Example 8: Synthesis of 3-(4-(10-(4-(4-(1-(2-amino-4-(trifluoromethoxy)benzoyl)piperidin-4-yl)quinazolin-7-yl)piperazin-1-yl)decyl)-1-oxoisoindolin-2-yl)piperidine-2,6-dione (7)

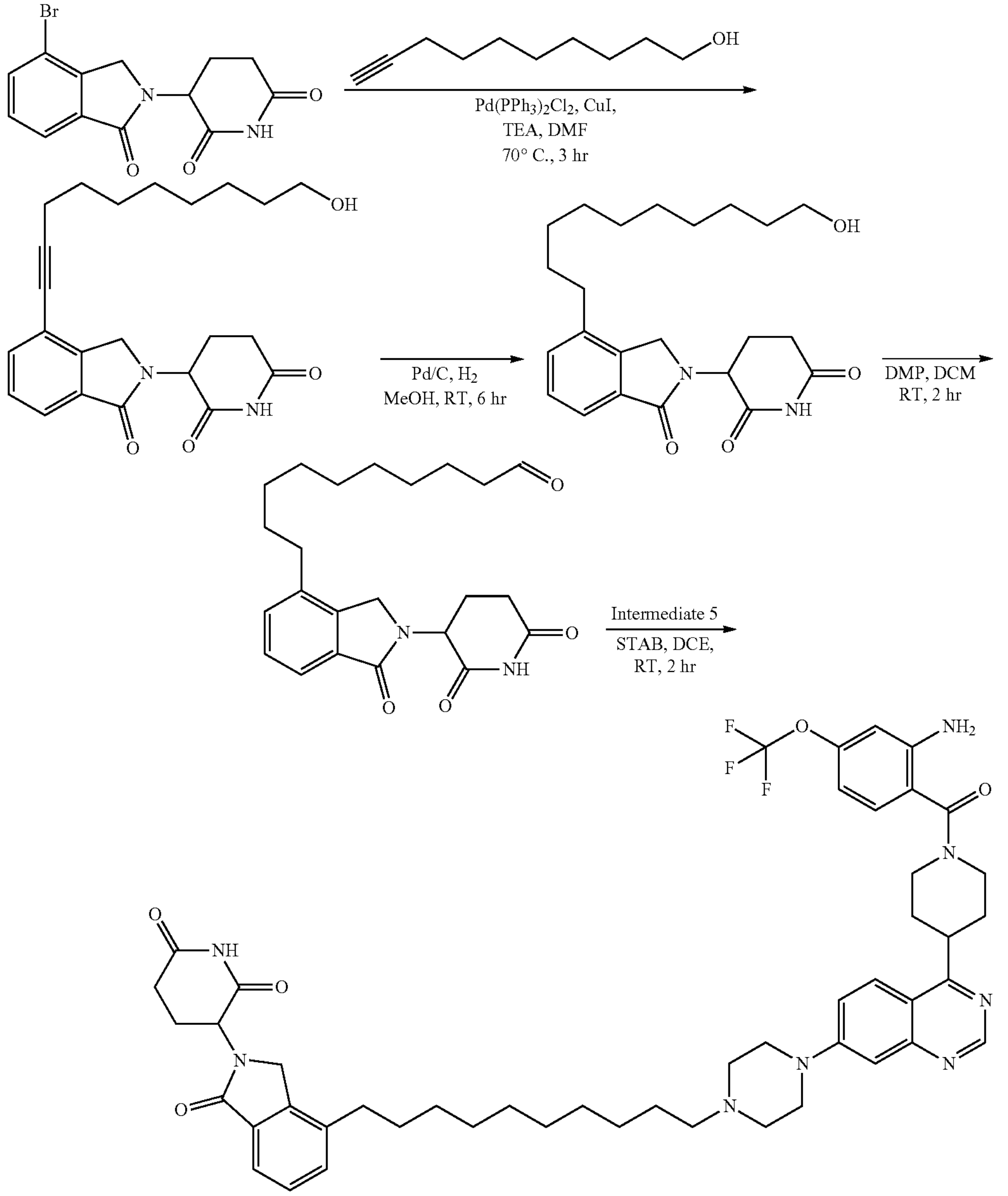

7

Step 1: Synthesis of 3-(4-(10-hydroxydec-1-yn-1-yl)-1-oxoisoindolin-2-yl)piperidine-2,6-dione: To 3-(4-bromo-1-oxoisoindolin-2-yl)piperidine-2,6-dione (323 mg, 1 mmol) was added dec-9-yn-1-ol (309 mg, 2 mmol), $Pd(PPh_3)_2Cl_2$ (70 mg, 0.1 mmol), copper iodide (38 mg, 0.2 mmol), triethylamine (TEA) (2.5 mL) and DMF (5 mL). The reaction mixture was flushed with nitrogen for 20 minutes and stirred at 70° C. for 3 hours. The reaction mixture was filtered over Celite, diluted with ethyl acetate, and washed with brine (10 mL×4). The organic layer was dried with anhydrous sodium sulfate, concentrated in vacuo and purified by reverse phase HPLC (35-99% MeOH in $H_2O$) to obtain 3-(4-(10-hydroxydec-1-yn-1-yl)-1-oxoisoindolin-2-yl)piperidine-2,6-dione as a yellow solid (174 mg, 44% yield). MS m/z 397.3 $[M+H]^+$.

Step 2: Synthesis of 3-(4-(10-hydroxydecyl)-1-oxoisoindolin-2-yl)piperidine-2,6-dione: To 3-(4-(10-hydroxydec-1-yn-1-yl)-1-oxoisoindolin-2-yl)piperidine-2,6-dione (35 mg, 0.087 mmol) was added Pd/C (4 mg) and MeOH (10 mL). To the reaction mixture was added $H_2$ (g), which was stirred at room temperature for 6 hours. The reaction mixture was filtered over Celite and concentrated in vacuo to obtain crude 3-(4-(10-hydroxydecyl)-1-oxoisoindolin-2-yl)piperidine-2,6-dione as a tan solid (quantitative yield). MS m/z 401.31 $[M+H]^+$.

Step 3: Synthesis of 10-(2-(2,6-dioxopiperidin-3-yl)-1-oxoisoindolin-4-yl)decanal: To 3-(4-(10-hydroxydecyl)-1-oxoisoindolin-2-yl)piperidine-2,6-dione (35 mg, 0.087 mmol) was added Dess-Martin periodinane (DMP) (74 mg, 0.174 mmol) and DCM (2 mL). The reaction was stirred at room temperature for 2 hours. The reaction mixture was concentrated in vacuo to obtain crude 10-(2-(2,6-dioxopiperidin-3-yl)-1-oxoisoindolin-4-yl)decanal as an off-white solid (quantitative yield). MS m/z 399.24 $[M+H]^+$.

Step 4: Synthesis of 3-(4-(10-(4-(4-(1-(2-amino-4-(trifluoromethoxy)benzoyl)piperidin-4-yl)quinazolin-7-yl)piperazin-1-yl)decyl)-1-oxoisoindolin-2-yl)piperidine-2,6-dione (7): To 10-(2-(2,6-dioxopiperidin-3-yl)-1-oxoisoindolin-4-yl)decanal (35 mg, 0.087 mmol) was added Intermediate 5 (20 mg, 0.04 mmol), sodium triacetoxyborohydride (STAB) (17 mg, 0.08 mmol), and 1,2-dichloroethane (DCE) (1 mL). The reaction was stirred for 2 hours at room temperature. The reaction mixture was washed with saturated sodium bicarbonate (aq.) and extracted with DCM (10 mL×3). The organic layer was dried with anhydrous sodium sulfate, concentrated in vacuo, and purified by reverse phase HPLC (10-70% MeOH in $H_2O$) to obtain 3-(4-(10-(4-(4-(1-(2-amino-4-(trifluoromethoxy)benzoyl)piperidin-4-yl)quinazolin-7-yl)piperazin-1-yl)decyl)-1-oxoisoindolin-2-yl)piperidine-2,6-dione (7) as a yellow solid (9 mg, 25% yield). $^1$H NMR (500 MHz, DMSO-$d_6$) δ 11.00 (s, 1H), 8.95 (s, 1H), 8.21 (d, J=9.4 Hz, 1H), 7.59-7.51 (m, 2H), 7.45 (d, J=4.2 Hz, 2H), 7.13 (t, J=9.2 Hz, 2H), 6.70-6.66 (m, 1H), 6.53-6.48 (m, 1H), 5.60 (s, 2H), 5.14 (dd, J=13.3, 5.1 Hz, 1H), 4.46 (d, J=17.1 Hz, 1H), 4.31 (d, J=17.1 Hz, 1H), 3.85 (d, J=13.5 Hz, 1H), 3.42 (s, 3H), 3.32 (s, 5H), 2.93 (ddd, J=17.3, 13.6, 5.4 Hz, 1H), 2.66-2.58 (m, 4H), 2.43 (td, J=13.2, 4.5 Hz, 2H), 2.32 (s, 2H), 2.02 (dtd, J=12.8, 5.4, 2.3 Hz, 1H), 1.89-1.80 (m, 4H), 1.64-1.56 (m, 2H), 1.47 (s, 2H), 1.34-1.23 (m, 14H). MS m/z 883.51 $[M+H]^+$.

Example 9: Synthesis of 3-(4-(6-(4-(4-(1-(2-amino-4-(trifluoromethoxy)benzoyl)piperidin-4-yl)quinazolin-7-yl)piperazin-1-yl)hexyl)-1-oxoisoindolin-2-yl)piperidine-2,6-dione (8)

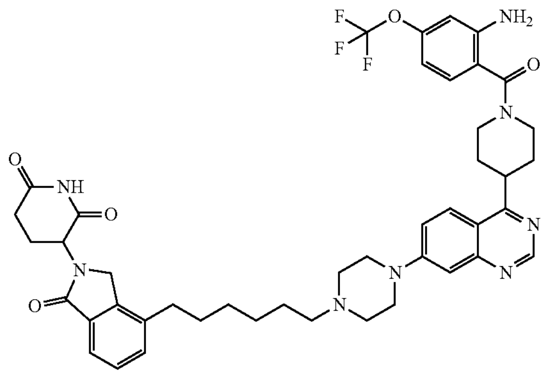 [SMILES: Nc1cc(OC(F)(F)F)ccc1C(=O)N1CCC(c2ncnc3cc(N4CCN(CCCCCCc5cccc6c5CN(C5CCC(=O)NC5=O)C6=O)CC4)ccc23)CC1]

Following the general procedure used for compound 7, hex-5-yn-1-ol was used to synthesize 3-(4-(6-(4-(4-(1-(2-amino-4-(trifluoromethoxy)benzoyl)piperidin-4-yl)quinazolin-7-yl)piperazin-1-yl)hexyl)-1-oxoisoindolin-2-yl)piperidine-2,6-dione (8) as a yellow solid. $^1$H NMR (500 MHz, DMSO-$d_6$) δ 11.01 (s, 1H), 9.79 (s, 1H), 9.03 (s, 1H), 8.33 (d, J=9.6 Hz, 1H), 7.60 (ddd, J=10.9, 6.3, 3.0 Hz, 2H), 7.50-7.46 (m, 2H), 7.27 (d, J=2.5 Hz, 1H), 7.14 (d, J=8.3 Hz, 1H), 6.68 (dd, J=2.4, 1.2 Hz, 1H), 6.51 (ddd, J=8.4, 2.4, 1.2 Hz, 1H), 5.16 (dd, J=13.3, 5.1 Hz, 1H), 4.48 (d, J=17.1 Hz, 1H), 4.32 (d, J=17.1 Hz, 1H), 4.26 (d, J=13.5 Hz, 2H), 3.94 (dd, J=10.3, 4.9 Hz, 1H), 3.63 (d, J=11.8 Hz, 2H), 3.26 (t, J=12.6 Hz, 2H), 3.13 (s, 5H), 2.94 (ddd, J=17.3, 13.6, 5.4 Hz, 1H), 2.69-2.59 (m, 3H), 2.43 (qd, J=13.2, 4.5 Hz, 2H), 2.03 (dtd, J=12.8, 5.4, 2.4 Hz, 1H), 1.93-1.80 (m, 4H), 1.67 (dt, J=22.7, 7.9 Hz, 4H), 1.41-1.32 (m, 4H). MS m/z 827.42 $[M+H]^+$.

Example 10: Synthesis of 3-(4-(3-(4-(4-(1-(2-amino-4-(trifluoromethoxy)benzoyl)piperidin-4-yl)quinazolin-7-yl)piperazin-1-yl)propyl)-1-oxoisoindolin-2-yl)piperidine-2,6-dione (9)

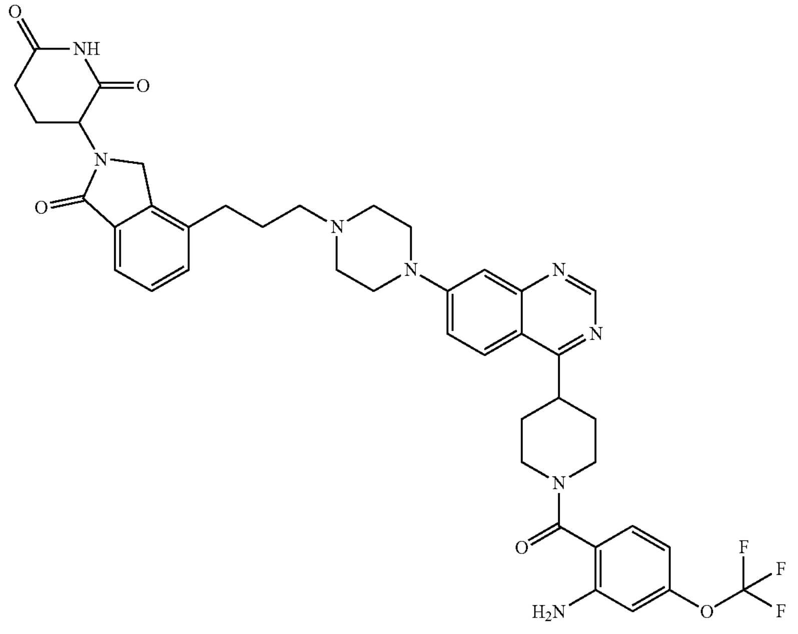 [SMILES: Nc1cc(OC(F)(F)F)ccc1C(=O)N1CCC(c2ncnc3cc(N4CCN(CCCc5cccc6c5CN(C5CCC(=O)NC5=O)C6=O)CC4)ccc23)CC1]

Following the general procedure used for compound 7, prop-2-yn-1-ol was used to synthesize 3-(4-(3-(4-(4-(1-(2-amino-4-(trifluoromethoxy)benzoyl)piperidin-4-yl)quinazolin-7-yl)piperazin-1-yl)propyl)-1-oxoisoindolin-2-yl)piperidine-2,6-dione (9) as a yellow solid. MS m/z 785.37 $[M+H]^+$.

Example 11: Synthesis of 3-(5-(3-(4-(4-(1-(2-amino-4-(trifluoromethoxy)benzoyl)piperidin-4-yl)quinazolin-7-yl)piperazin-1-yl)propyl)-1-oxoisoindolin-2-yl)piperidine-2,6-dione (10)

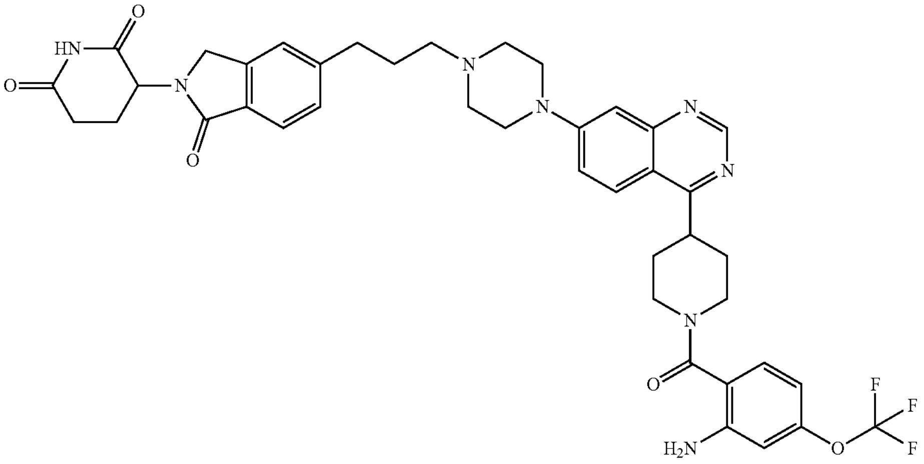 [SMILES: Nc1cc(OC(F)(F)F)ccc1C(=O)N1CCC(c2ncnc3cc(N4CCN(CCCc5ccc6c(c5)CN(C5CCC(=O)NC5=O)C6=O)CC4)ccc23)CC1]

Following the general procedure used for compound 7, 3-(5-bromo-1-oxoisoindolin-2-yl)piperidine-2,6-dione and prop-2-yn-1-ol was used to synthesize 3-(5-(3-(4-(4-(1-(2-amino-4-(trifluoromethoxy)benzoyl)piperidin-4-yl)quinazolin-7-yl)piperazin-1-yl)propyl)-1-oxoisoindolin-2-yl)piperidine-2,6-dione (10) as a yellow solid. $^1$H NMR (500 MHz, DMSO-$d_6$) δ 11.03 (s, 1H), 9.90 (s, 1H), 9.04 (s, 1H), 8.34 (d, J=9.6 Hz, 1H), 7.65-7.61 (m, 2H), 7.56-7.49 (m, 2H), 7.28 (d, J=2.5 Hz, 1H), 7.14 (d, J=8.4 Hz, 1H), 6.68 (dd, J=2.4, 1.2 Hz, 1H), 6.51 (ddd, J=8.4, 2.4, 1.2 Hz, 1H), 5.18 (dd, J=13.3, 5.2 Hz, 1H), 4.51 (d, J=17.1 Hz, 1H), 4.35 (d, J=17.0 Hz, 1H), 4.28 (d, J=13.3 Hz, 2H), 3.95 (dq, J=11.8, 6.2 Hz, 1H), 3.67 (d, J=11.3 Hz, 2H), 3.26 (d, J=13.1 Hz, 8H), 2.96 (ddd, J=17.3, 13.7, 5.4 Hz, 1H), 2.78-2.69 (m, J=7.4, 6.9 Hz, 2H), 2.64 (dt, J=17.2, 3.8 Hz, 1H), 2.39 (qd, J=13.3, 4.5 Hz, 1H), 2.13-2.01 (m, 3H), 1.94-1.78 (m, 4H). MS m/z 785.36 $[M+H]^+$.

Example 12: Synthesis of 3-(5-(6-(4-(4-(1-(2-amino-4-(trifluoromethoxy)benzoyl)piperidin-4-yl)quinazolin-7-yl)piperazin-1-yl)hexyl)-1-oxoisoindolin-2-yl)piperidine-2,6-dione (11)

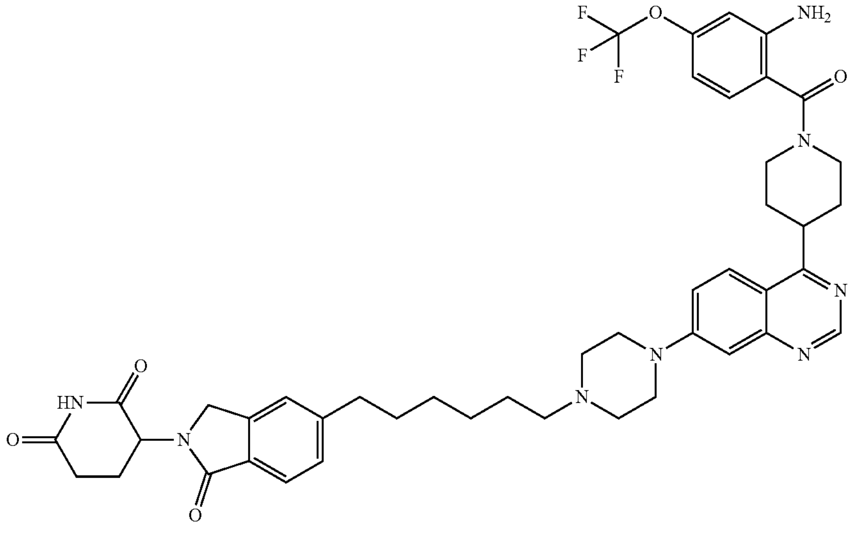 [SMILES: Nc1cc(OC(F)(F)F)ccc1C(=O)N1CCC(c2ncnc3cc(N4CCN(CCCCCCc5ccc6c(c5)CN(C5CCC(=O)NC5=O)C6=O)CC4)ccc23)CC1]

Following the general procedure used for compound 7, 3-(5-bromo-1-oxoisoindolin-2-yl)piperidine-2,6-dione and hex-5-yn-1-ol was used to synthesize 3-(5-(6-(4-(4-(1-(2-amino-4-(trifluoromethoxy)benzoyl)piperidin-4-yl)quinazolin-7-yl)piperazin-1-yl)hexyl)-1-oxoisoindolin-2-yl)piperidine-2,6-dione (11) as a yellow solid. $^1$H NMR (500 MHz, DMSO-$d_6$) δ 10.99 (s, 1H), 9.78 (s, 1H), 9.03 (s, 1H), 8.33 (d, J=9.5 Hz, 1H), 7.66 (d, J=7.8 Hz, 1H), 7.61 (dd, J=9.5, 2.6 Hz, 1H), 7.44 (s, 1H), 7.36 (dd, J=7.8, 1.4 Hz, 1H), 7.27 (d, J=2.5 Hz, 1H), 7.14 (d, J=8.4 Hz, 1H), 6.68 (d, J=2.3 Hz, 1H), 6.54-6.48 (m, 1H), 5.11 (dd, J=13.3, 5.1 Hz, 1H), 4.43 (d, J=17.2 Hz, 1H), 4.33-4.22 (m, 3H), 3.94 (dt, J=11.8, 7.4 Hz, 1H), 3.62 (d, J=11.8 Hz, 2H), 3.26 (t, J=12.8 Hz, 2H), 3.14 (d, J=8.8 Hz, 5H), 2.92 (ddd, J=17.4, 13.6, 5.4 Hz, 1H), 2.73 (t, J=7.6 Hz, 2H), 2.65-2.57 (m, 1H), 2.40 (qd, J=13.2, 4.6 Hz, 1H), 2.00 (dtd, J=12.9, 5.5, 2.4 Hz, 1H), 1.93-1.77 (m, 4H), 1.74-1.58 (m, 5H), 1.35 (q, J=3.8 Hz, 4H). MS m/z 827.42 [M+H]$^+$.

Example 13: Synthesis of 3-(5-(10-(4-(4-(1-(2-amino-4-(trifluoromethoxy)benzoyl)piperidin-4-yl)quinazolin-7-yl)piperazin-1-yl)decyl)-1-oxoisoindolin-2-yl)piperidine-2,6-dione (12)

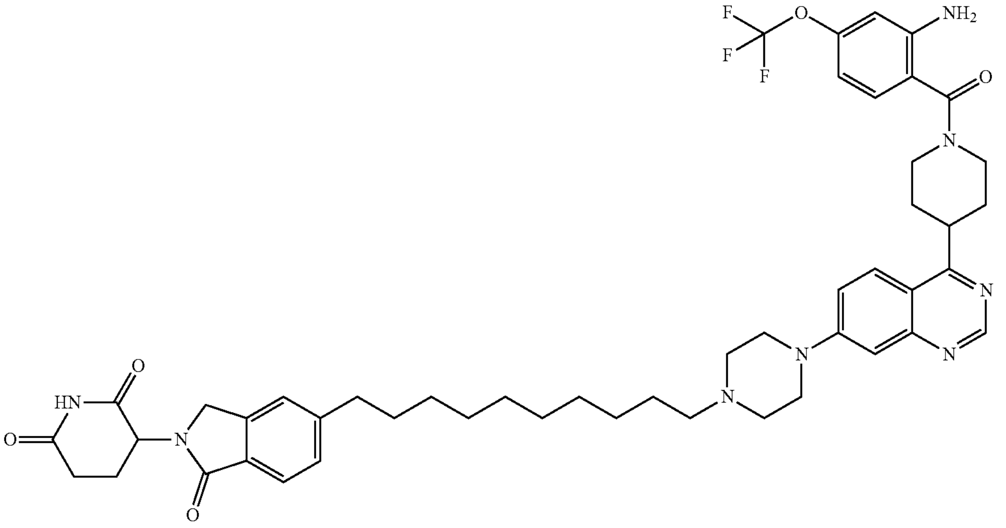 [SMILES: Nc1cc(OC(F)(F)F)ccc1C(=O)N1CCC(c2ncnc3cc(N4CCN(CCCCCCCCCCc5ccc6c(c5)CN(C5CCC(=O)NC5=O)C6=O)CC4)ccc23)CC1]

Following the general procedure used for compound 7, 3-(5-bromo-1-oxoisoindolin-2-yl)piperidine-2,6-dione and dec-9-yn-1-ol was used to synthesize 3-(5-(10-(4-(4-(1-(2-amino-4-(trifluoromethoxy)benzoyl)piperidin-4-yl)quinazolin-7-yl)piperazin-1-yl)decyl)-1-oxoisoindolin-2-yl)piperidine-2,6-dione (12) as a yellow solid. $^1$H NMR (500 MHz, DMSO-$d_6$) δ 10.99 (s, 1H), 9.80 (s, 1H), 9.03 (s, 1H), 8.33 (d, J=9.6 Hz, 1H), 7.63 (dd, J=17.6, 8.7 Hz, 2H), 7.43 (s, 1H), 7.34 (d, J=7.7 Hz, 1H), 7.27 (d, J=2.5 Hz, 1H), 7.14 (d, J=8.4 Hz, 1H), 6.68 (d, J=2.4 Hz, 1H), 6.51 (dd, J=8.4, 2.4 Hz, 1H), 5.11 (dd, J=13.3, 5.2 Hz, 1H), 4.42 (d, J=17.2 Hz, 1H), 4.32-4.22 (m, 3H), 3.93 (tq, J=11.5, 6.0 Hz, 1H), 3.63 (d, J=11.8 Hz, 2H), 3.26 (t, J=12.6 Hz, 2H), 3.15 (t, J=10.1 Hz, 6H), 2.92 (ddd, J=17.3, 13.6, 5.4 Hz, 1H), 2.70 (t, J=7.6 Hz, 2H), 2.61 (dt, J=17.7, 3.5 Hz, 1H), 2.43-2.36 (m, 1H), 2.00 (dtd, J=12.9, 5.4, 2.4 Hz, 1H), 1.89-1.78 (m, 4H), 1.71-1.57 (m, 4H), 1.37-1.12 (m, 14H). MS m/z 883.47 [M+H]$^+$.

Example 14: Compounds Degrade ERK5 in Molt4 Cells

Figure 2A:
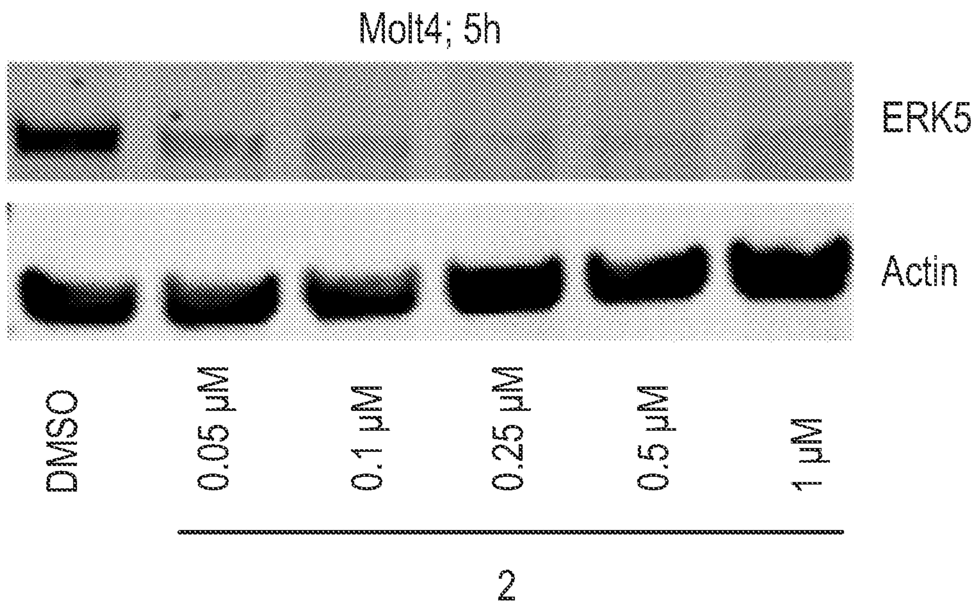
FIG. 2A is an immunoblot showing ERK5 degradation for compound 2 at 0.05 μM, 0.1 μM, 0.25 μM, 0.5 μM and 1 μM in Molt4 cells after 5 hours, showing that compound 2 displays potent ERK5 degradation at concentrations as low as 0.05 μM.
Figure 2B:
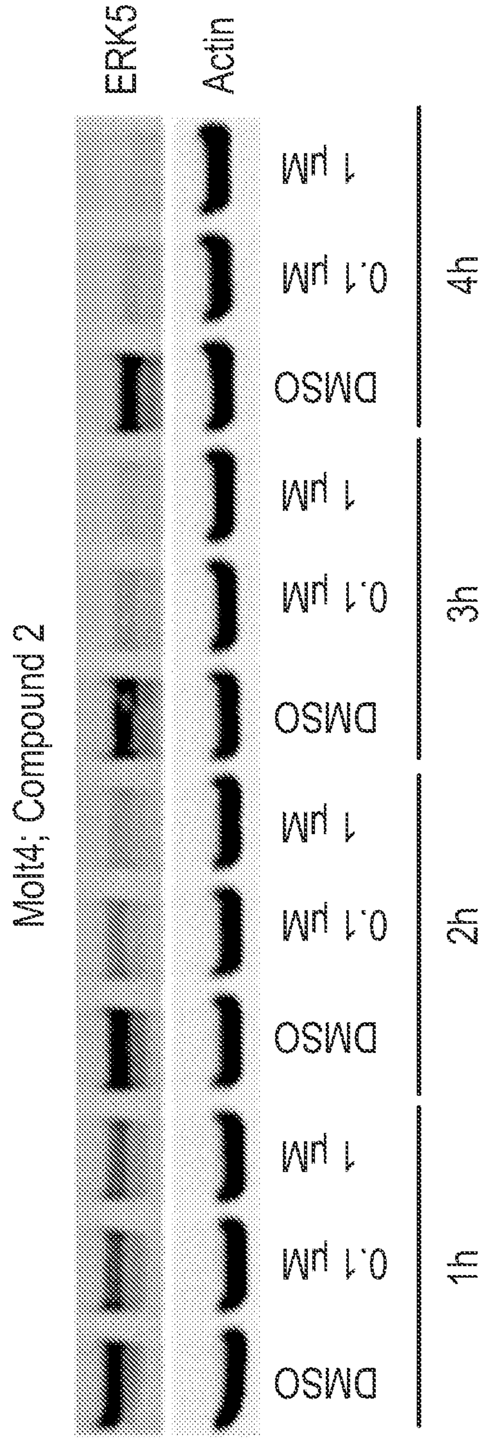
FIG. 2B is a time course immunoblot showing ERK5 degradation for compound 2 at 0.1 μM and 1 μM in Molt4 cells after 1 h, 2 h, 3 h, and 4 h, showing that compound 2 induces ERK5 degradation within 2 hours of treatment.
Figure 2C:
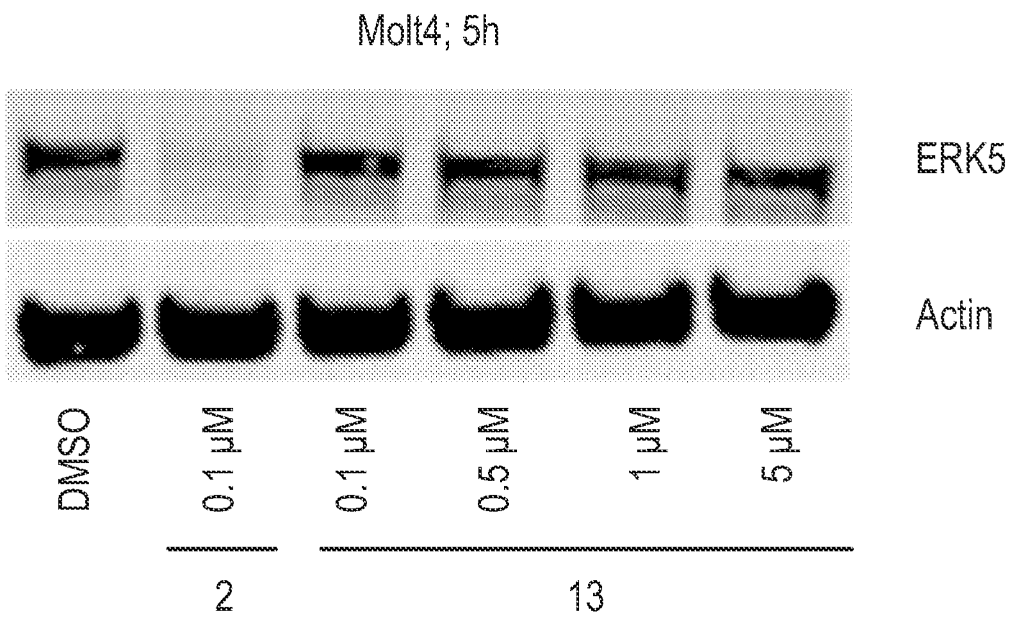
FIG. 2C is an immunoblot comparing ERK5 degradation for compound 2 at 0.1 μM in Molt4 cells after 5 h, showing that the negative control, compound 13, which cannot recruit the E3 ligase von Hippel-Lindau disease tumor suppressor (VHL), does not induce ERK5 degradation up to 5 μM.

Molt4 cells were maintained in RPMI 1640 supplemented with 10% FBS and 100 U/mL Penicillin-Streptomycin at 37° C. in the presence of 5% $CO_2$. Molt4 cells were treated with 0.1 μM or 1 μM of the corresponding compounds for 5 hours. The cells were then lysed with RIPA buffer containing phosphatase/protease inhibitor, and cell extracts were pre-cleared by centrifugation at 21000×g for 5 minutes at 4° C. The Pierce BCA protein assay kit was used to assess protein lysate concentration and normalized using SDS sample buffer. Lysates were resolved on 4-12% Tris-Base gels and transferred to an Immuno-Blot PVDF membrane. The membrane was blocked for 1 hour, then incubated with primary antibodies against ERK5 (Cell Signaling) and j-Actin (Cell Signaling). The next day, membranes were washed with TBS-T, then incubated at room temperature for 1 hour with IRDye® 800-labeled goat anti-rabbit IgG and IRDye® 800-labeled goat anti-mouse IgG (LI-COR) secondary antibodies. The membranes were detected on Odyssey® CLx system. FIG. 1A shows that compound 2 potently degraded ERK5 in Molt4 cell lines. FIG. 2A shows that compound 2 induced ERK5 degradation at concentrations as low as 50 nM after 5 hours of treatment in Molt4 cells. FIG. 2B demonstrates that compound 2 displayed potent ERK5 degradation at both 0.1 μM and 1 μM within 2 hours of treatment in Molt4 cells. FIG. 2C demonstrates that compound 2 degraded ERK5 in a VHL-dependent manner and that the negative control, compound 13, did not recruit the VHL E3 ligase or induce ERK5 degradation.

Figure 3:
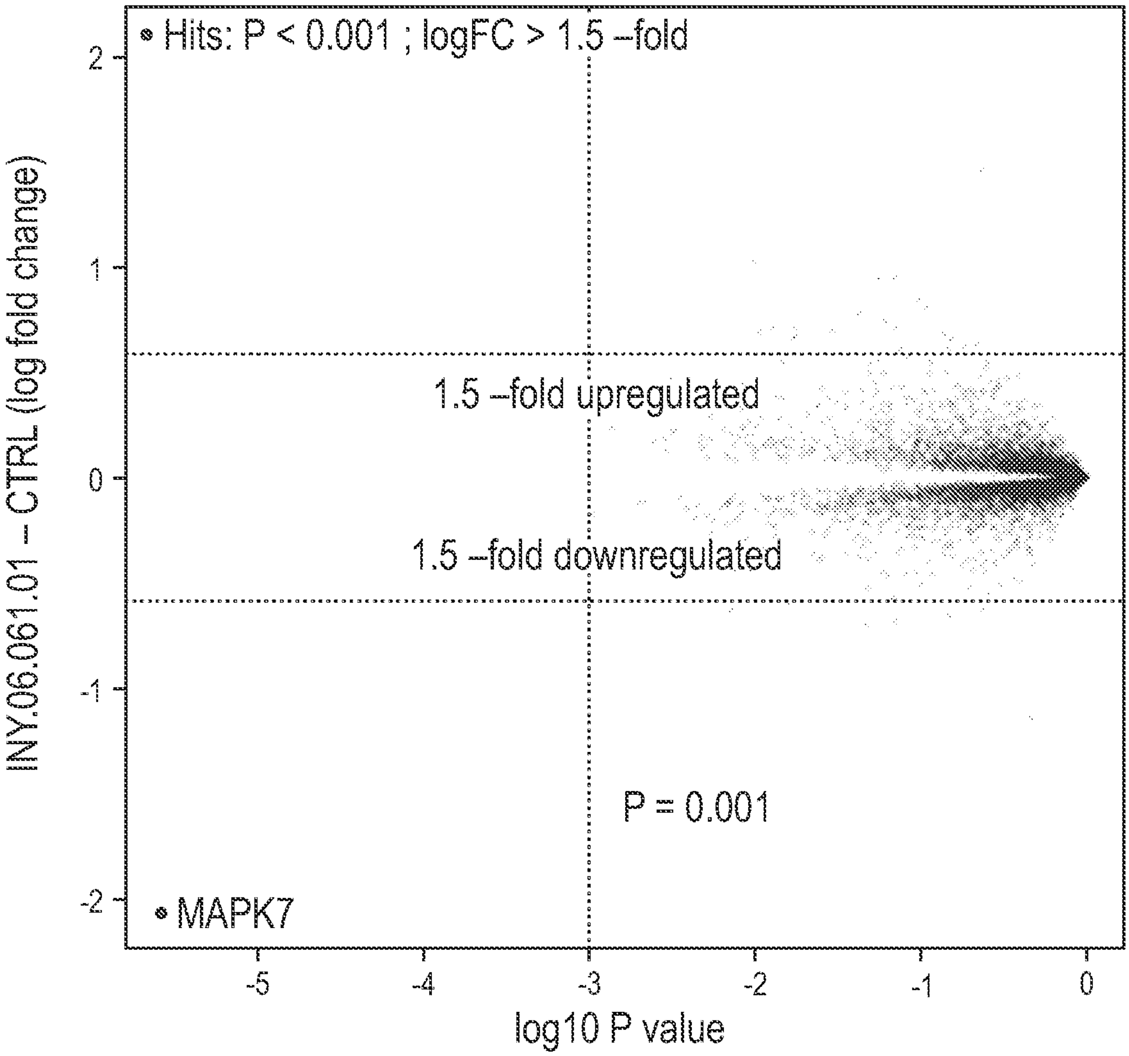
FIG. 3 is a scatterplot that depicts the change in relative protein abundance of compound 2 (100 nM, 5 h)-treated MOLT4 cells compared with DMSO vehicle control-treated cells. Protein abundance measurements were made using tandem mass tag quantitative mass spectrometry. The log 2fold change (log 2FC) is shown on the y axis and negative log 10p value (−log 10p value) on the x axis.

FIG. 3 shows significant downregulation of only ERK5 protein levels in an unbiased, multiplexed mass spectrometry-based proteomics analysis after treating Molt4 cells with 100 nM of compound 2 for 5 hours.

Structure of compound 13; (2R,4S)-1-((S)-2-(6-(4-(4-(1-(2-amino-4-(trifluoromethoxy)benzoyl)piperidin-4-yl)quinazolin-7-yl)piperazin-1-yl)hexanamido)-3,3-dimethylbutanoyl)-4-hydroxy-N—((S)-1-(4-(4-methylthiazol-5-yl)phenyl)ethyl)pyrrolidine-2-carboxamide, used as a negative control in the degradation experiments.

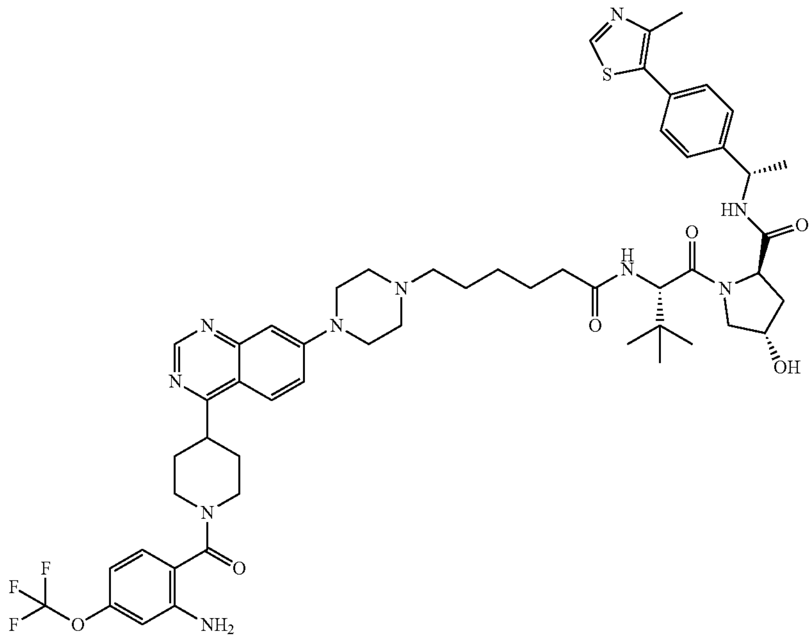 [SMILES: Cc1ncsc1-c1ccc([C@H](C)NC(=O)[C@H]2C[C@H](O)CN2C(=O)[C@@H](NC(=O)CCCCCN2CCN(c3ccc4c(C5CCN(C(=O)c6ccc(OC(F)(F)F)cc6N)CC5)ncnc4c3)CC2)C(C)(C)C)cc1]

All patent publications and non-patent publications are indicative of the level of skill of those skilled in the art to which this disclosure pertains. All these publications are herein incorporated by reference to the same extent as if each individual publication were specifically and individually indicated as being incorporated by reference.

Although the disclosure herein has been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims.

What is claimed is:

1. A compound, or a pharmaceutically acceptable salt or stereoisomer thereof, having a structure represented by formula (I):

(I)

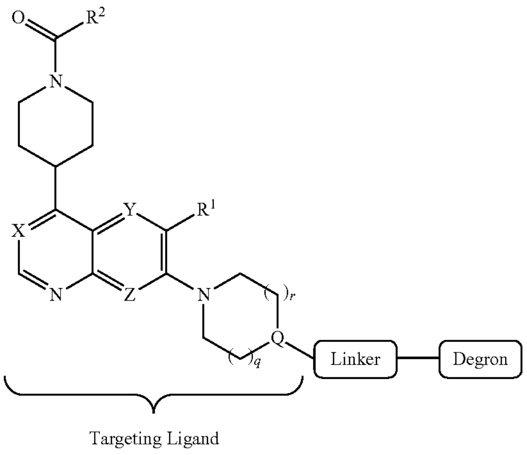

, wherein X is CH, $CR^3$, or N;

Y is CH, $CR^3$, or N;

Z is CH, $CR^3$, or N;

Q is CH or N;

$R^1$ is H, $C_1$-$C_6$ alkyl, or $C_1$-$C_6$ alkoxy;

$R^2$ is a phenyl or pyridyl ring which is optionally substituted once or twice identically or differently with a substituent selected from halogen, OH, CN, $C_1$-$C_6$ alkyl, $C_1$-$C_6$ alkoxy, $C_1$-$C_6$ haloalkoxy, $C_1$-$C_6$ alkyl which is optionally substituted with a $C_1$-$C_6$ alkoxy- or $C_1$-$C_6$ haloalkoxy-substituent, $C_2$-$C_6$-alkenyl, $C_2$-$C_6$-alkynyl, $C_3$-$C_8$-cycloalkyl, —C(═O)$NR^4R^5$, —$NH_2$, —NH—C(═O)—$C_1$-$C_6$-alkyl, $C_1$-$C_6$-alkoxy which is optionally substituted with a hydroxyl or $C_1$-$C_6$-alkyl substituent, —O—$C_3$-$C_8$-cycloalkyl, —O-(4- to 7-membered heterocycloalkyl), $C_1$-$C_6$-alkylthio, $C_1$-$C_6$-haloalkylthio, or —S(═O)$_2$-$C_1$-$C_6$-alkyl group;

$R^3$ is H, or $C_1$-$C_6$ alkyl;

$R^4$ and $R^5$ independently represent hydrogen, a $C_1$-$C_6$-alkyl or phenyl group;

each occurrence of q and r is independently 0 or 1;

the degron ("Degron") is represented by any one of the following structures:

(V1)

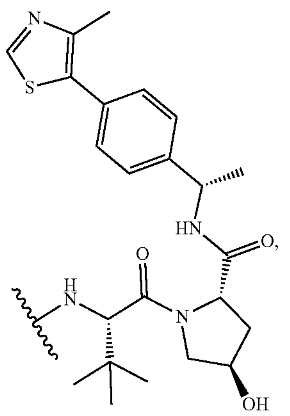

(V2)

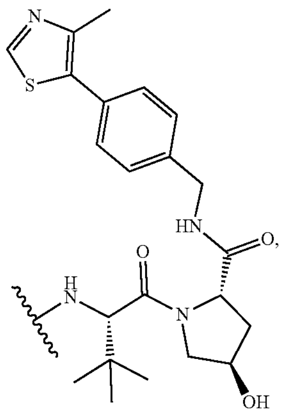

(C1)

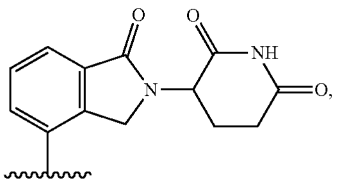

(C2)

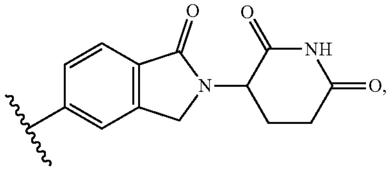

and

-continued (C3)

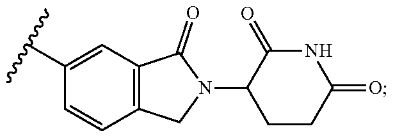

and the linker ("Linker") comprises an alkylene chain which may be interrupted by, and/or terminate (at either or both termini) in at least one of —O—, —S—, —N(R')—, —C≡C—, —C(O)—, —C(O)O—, —OC(O)—, —OC(O)O—, —C(NOR')—, —C(O)N(R')—, —C(O)N(R')C(O)—, —C(O)N(R')C(O)N(R')—, —N(R')C(O)—, —N(R')C(O)N(R'), —N(R')C(O)O—, —OC(O)N(R')—, —C(NR')—, —N(R')C(NR')—, —C(NR')N(R')—, —N(R')C(NR')N(R')—, —OB(Me)O—, —S(O)$_2$—, —OS(O)—, —S(O)O—, —S(O)—, —OS(O)$_2$—, —S(O)$_2$O—, —N(R')S(O)$_2$—, —S(O)$_2$N(R')—, —N(R')S(O)—, —S(O)N(R')—, —N(R')S(O)$_2$N(R)—, —N(R')S(O)N(R')—, $C_3$-$C_{12}$ carbocyclene, 3- to 12-membered heterocyclene, 5- to 12-membered heteroarylene or any combination thereof, wherein R' is H, F, or $C_1$-$C_6$ alkyl, and wherein the interrupting and the one or both terminating groups may be the same or different, or the linker comprises a polyethylene glycol (PEG) chain which may terminate (at either or both termini) in at least one of —S—, —N(R')—, —C≡C—, —C(O)—, —C(O)O—, —OC(O)—, —OC(O)O—, —C(NOR')—, —C(O)N(R')—, —C(O)N(R')C(O)—, —C(O)N(R')C(O)N(R')—, —N(R')C(O)—, —N(R')C(O)N(R')—, —N(R')C(O)O—, —OC(O)N(R')—, —C(NR')—, —N(R')C(NR')—, —C(NR')N(R')—, —N(R')C(NR')N(R')—, —OB(Me)O—, —S(O)$_2$—, —OS(O)—, —S(O)O—, —S(O)—, —OS(O)$_2$—, —S(O)$_2$O—, —N(R')S(O)$_2$—, —S(O)$_2$N(R')—, —N(R')S(O)—, —S(O)N(R')—, —N(R')S(O)$_2$N(R')—, —N(R')S(O)N(R')—, $C_{3-12}$ carbocyclene, 3- to 12-membered heterocyclene, 5- to 12-membered heteroarylene or any combination thereof, wherein R' is H, F, or $C_1$-$C_6$ alkyl, and wherein the one or both terminating groups may be the same or different.

2. The compound of claim 1, or a pharmaceutically acceptable salt or stereoisomer thereof, wherein Y is CH and Z is CH.

3. The compound of any claim 1, or a pharmaceutically acceptable salt or stereoisomer thereof, wherein q is 1 and r is 1.

4. The compound of claim 1, or a pharmaceutically acceptable salt or stereoisomer thereof, wherein Q is N.

5. The compound of claim 1, or a pharmaceutically acceptable salt or stereoisomer thereof, wherein X is N.

6. The compound of claim 1, or a pharmaceutically acceptable salt or stereoisomer thereof, wherein $R^2$ is a phenyl which is optionally substituted once or twice identically or differently with a substituent selected from halogen, OH, CN, $C_1$-$C_6$ alkyl, $C_1$-$C_6$ alkoxy, $C_1$-$C_6$ haloalkoxy, $C_1$-$C_6$ alkyl which is optionally substituted with a $C_1$-$C_6$ alkoxy- or $C_1$-$C_6$ haloalkoxy-substituent, $C_2$-$C_6$-alkenyl, $C_2$-$C_6$-alkynyl, $C_3$-$C_8$-cycloalkyl, —C(═O)$NR^4R^5$, —$NH_2$, —NH—C(═O)—$C_1$-$C_6$-alkyl, $C_1$-$C_6$-alkoxy which is optionally substituted with a hydroxyl or $C_1$-$C_6$-alkyl substituent, —O—$C_3$-$C_8$-cycloalkyl, —O-(4- to 7-membered heterocycloalkyl), $C_1$-$C_6$-alkylthio, $C_1$-$C_6$-haloalkylthio, or —S(═O)$_2$—$C_1$-$C_6$-alkyl group, and wherein $R^4$ and $R^5$ independently represent hydrogen, a $C_1$-$C_6$-alkyl or phenyl group.

7. The compound of claim 6, or a pharmaceutically acceptable salt or stereoisomer thereof, wherein $R^2$ is a phenyl which is optionally substituted once or twice identically or differently with a $C_1$-$C_6$ haloalkoxy group.

8. The compound of claim 7, or a pharmaceutically acceptable salt or stereoisomer thereof, wherein the $C_1$-$C_6$ haloalkoxy group is a $C_1$-$C_6$ trifluoroalkoxy group.

9. The compound of claim 8, or a pharmaceutically acceptable salt or stereoisomer thereof, wherein the $C_1$-$C_6$ trifluoroalkoxy group is a trifluoromethoxy group.

10. The compound of claim 1, or a pharmaceutically acceptable salt or stereoisomer thereof, wherein $R^2$ is

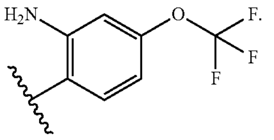 [SMILES: *c1ccc(OC(F)(F)F)cc1N]

11. The compound of claim 1, or a pharmaceutically acceptable salt or stereoisomer thereof, wherein the degron is represented by any one of the following structures:

(VI)

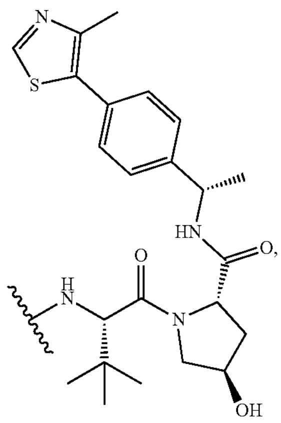

and (V2)

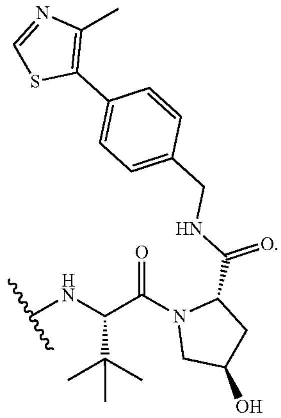

12. The compound of claim 1, or a pharmaceutically acceptable salt or stereoisomer thereof, wherein the degron is represented by any one of the following structures:

(C1)

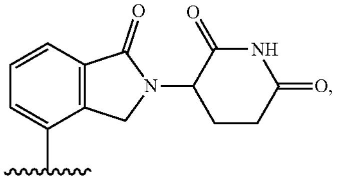

-continued (C2)

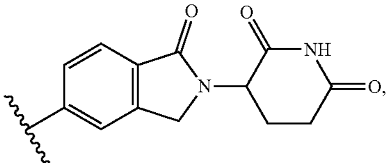

and (C3)

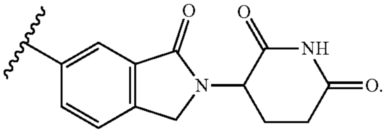

13. The compound of claim 1, or a pharmaceutically acceptable salt or stereoisomer thereof, wherein the linker comprises an alkylene chain which may be interrupted by, and/or terminate (at either or both termini) in at least one of —O—, —S—, —N(R')—, —C≡C—, —C(O)—, —C(O)O—, —OC(O)—, —OC(O)O—, —C(NOR')—, —C(O)N(R')—, —C(O)N(R')C(O)—, —C(O)N(R')C(O)N(R')—, —N(R')C(O)—, —N(R')C(O)N(R')—, —N(R')C(O)O—, —OC(O)N(R')—, —C(NR')—, —N(R')C(NR')—, —C(NR')N(R')—, —N(R')C(NR')N(R')—, —OB(Me)O—, —$S(O)_2$—, —OS(O)—, —S(O)O—, —S(O)—, —$OS(O)_2$—, —$S(O)_2O$—, —$N(R')S(O)_2$—, —$S(O)_2N(R')$—, —N(R')S(O)—, —S(O)N(R')—, —$N(R')S(O)_2N(R')$—, —N(R')S(O)N(R')—, $C_3$-$C_{12}$ carbocyclene, 3- to 12-membered heterocyclene, 5- to 12-membered heteroarylene or any combination thereof, wherein R' is H, F, or $C_1$-$C_6$ alkyl, and wherein the interrupting and the one or both terminating groups may be the same or different.

14. The compound of claim 13, or a pharmaceutically acceptable salt or stereoisomer thereof, wherein the alkylene chain comprises 1-10 alkylene units.

15. The compound of claim 1, or a pharmaceutically acceptable salt or stereoisomer thereof, wherein the linker comprises a polyethylene glycol (PEG) chain which may terminate (at either or both termini) in at least one of —S—, —N(R')—, —C≡C—, —C(O)—, —C(O)O—, —OC(O)—, —OC(O)O—, —C(NOR')—, —C(O)N(R')—, —C(O)N(R')C(O)—, —C(O)N(R')C(O)N(R')—, —N(R')C(O)—, —N(R')C(O)N(R')—, —N(R')C(O)O—, —OC(O)N(R')—, —C(NR')—, —N(R')C(NR')—, —C(NR')N(R')—, —N(R')C(NR')N(R')—, —OB(Me)O—, —$S(O)_2$—, —OS(O)—, —S(O)O—, —S(O)—, —$OS(O)_2$—, —$S(O)_2O$—, —$N(R')S(O)_2$—, —$S(O)_2N(R')$—, —N(R')S(O)—, —S(O)N(R')—, —$N(R')S(O)_2N(R')$—, —N(R')S(O)N(R')—, $C_{3-12}$ carbocyclene, 3- to 12-membered heterocyclene, 5- to 12-membered heteroarylene or any combination thereof, wherein R' is H, F, or $C_1$-$C_6$ alkyl, and wherein the one or both terminating groups may be the same or different.

16. The compound of claim 15, or a pharmaceutically acceptable salt or stereoisomer thereof, wherein the polyethylene glycol chain comprises 1-6 PEG units.

17. The compound of claim 1, or a pharmaceutically acceptable salt or stereoisomer thereof, wherein the linker is represented by any one of the structures:

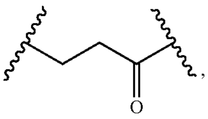
,
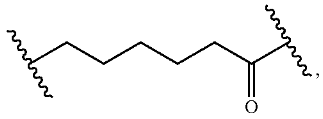
,

-continued
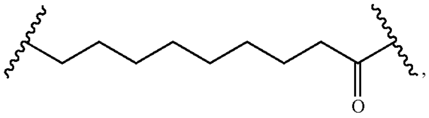
,
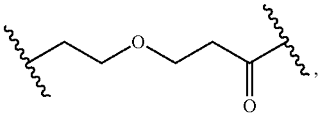
,
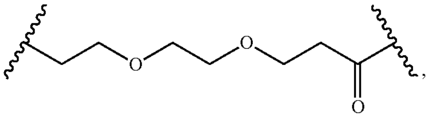
,
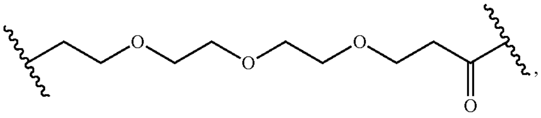
,
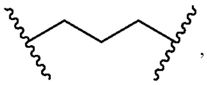
,
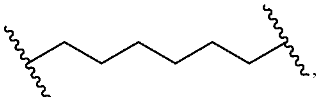
, and
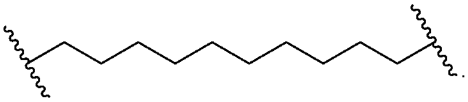
.
18. A compound which is:
(1)
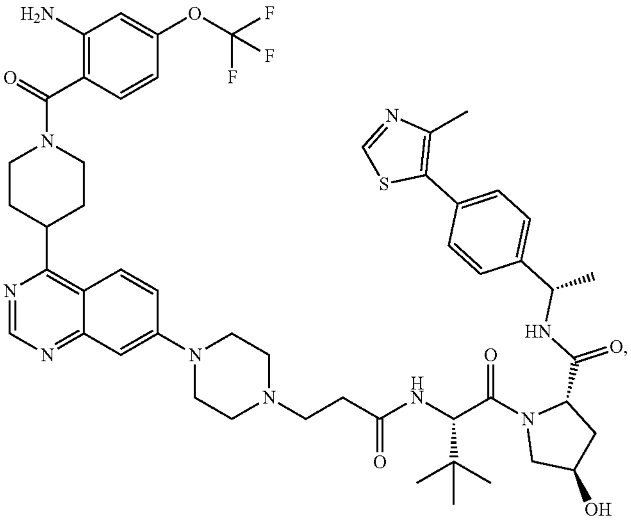
(2)
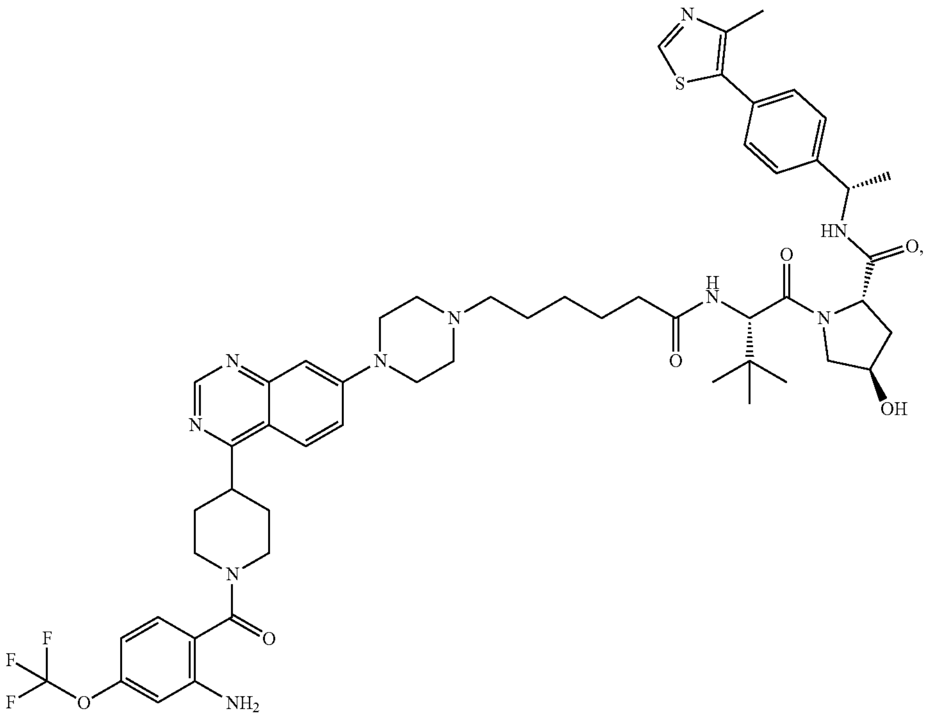

-continued
(3)
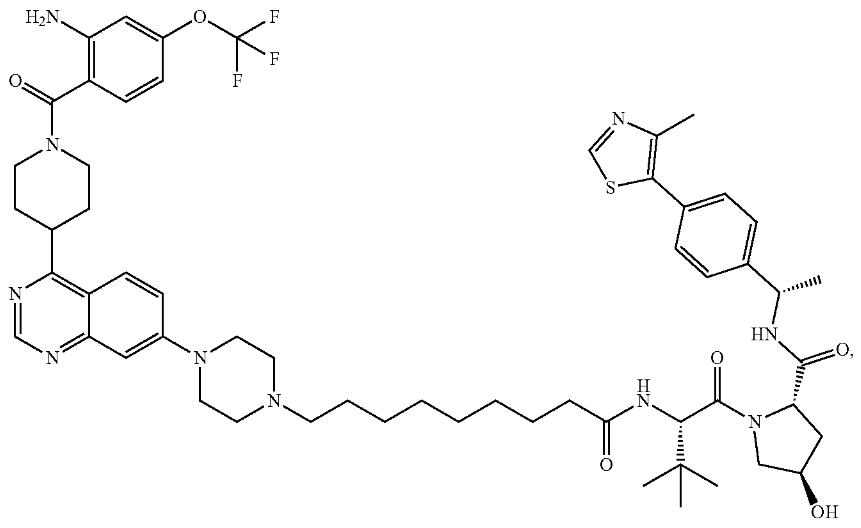
(4)
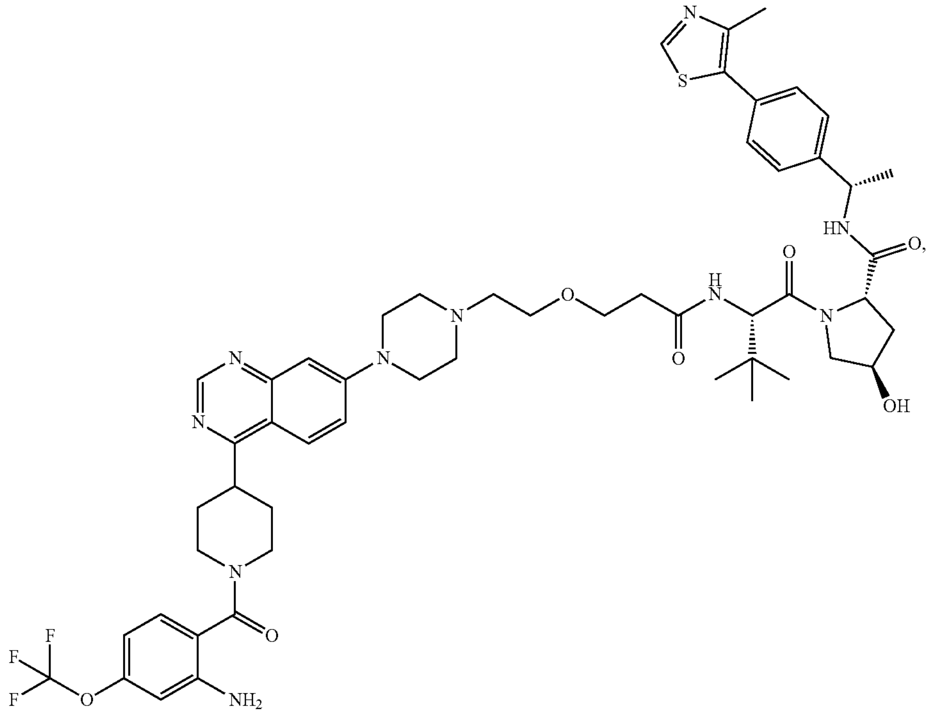

-continued
(5)
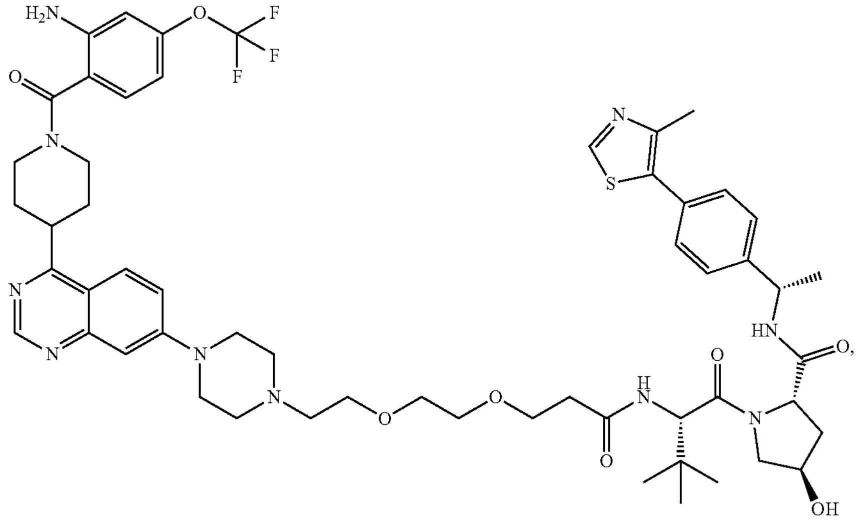
(6)
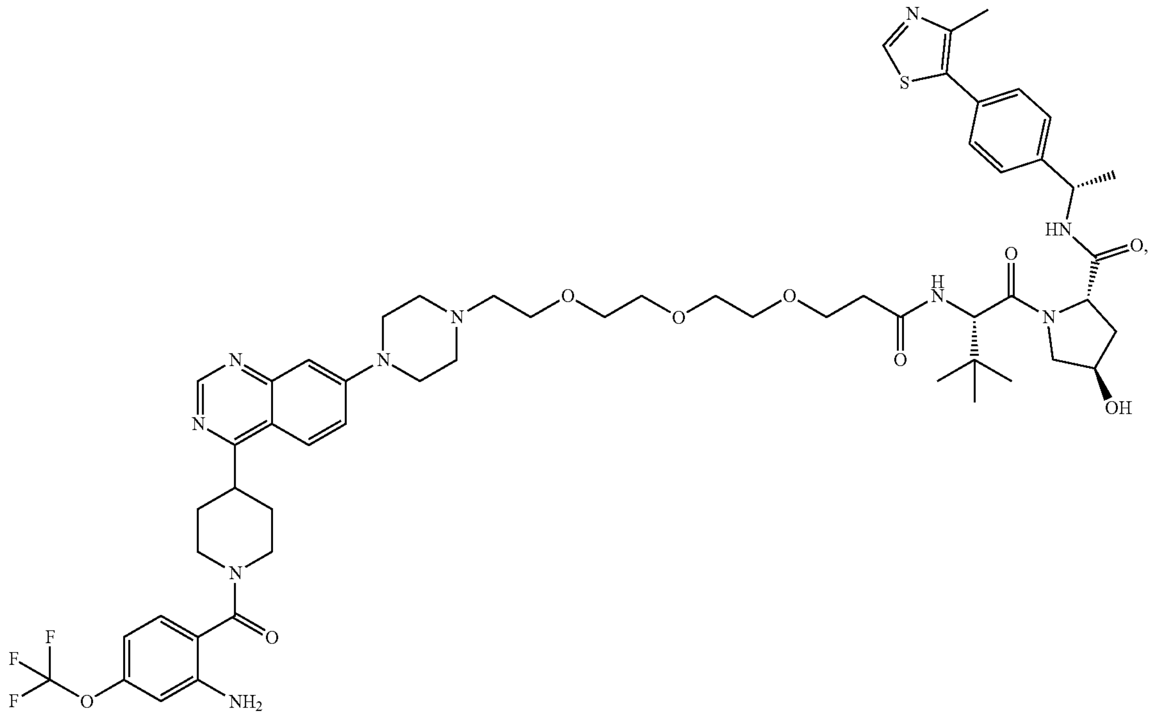

-continued
(7)
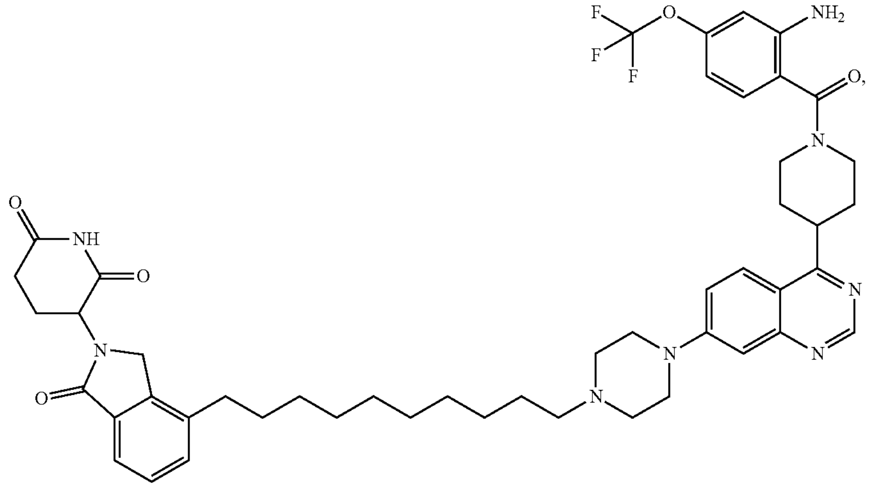
(8)
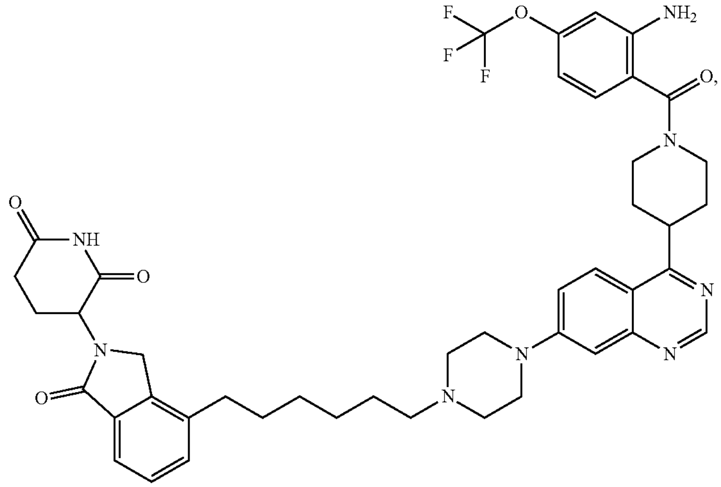
(9)
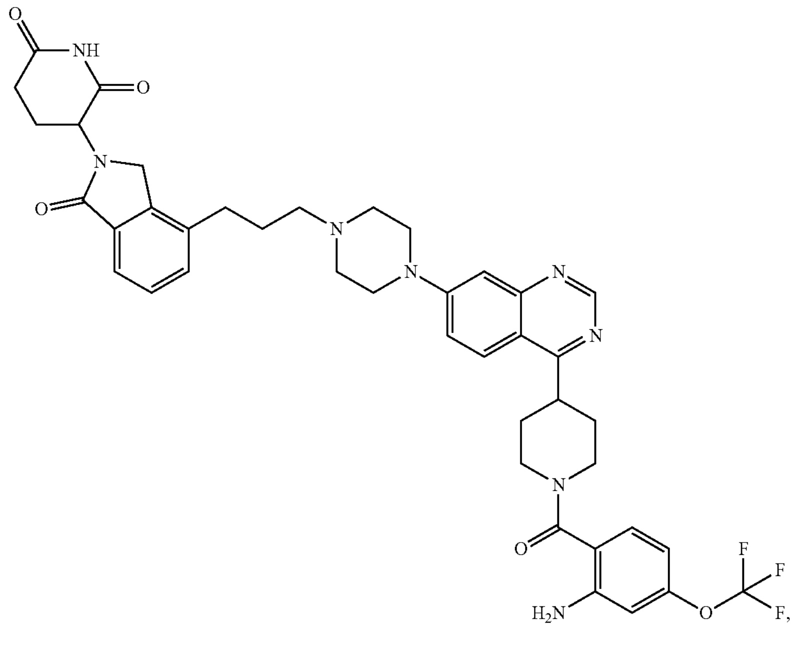

-continued
(10)
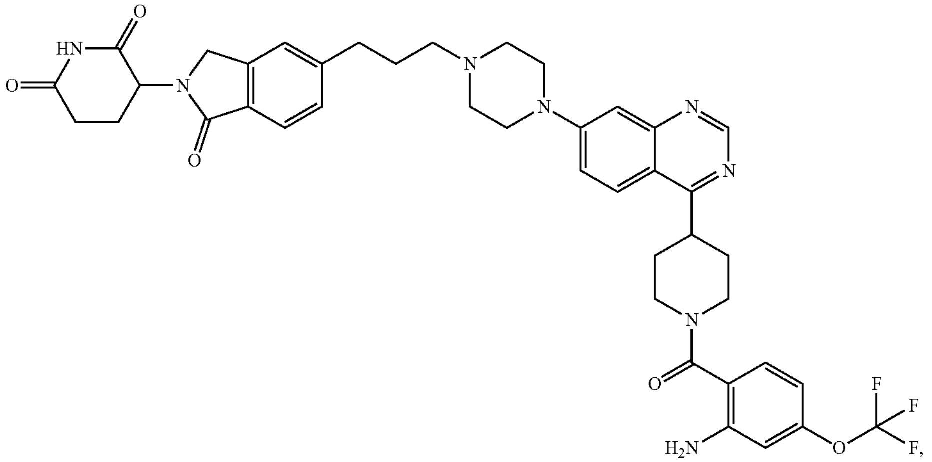
(11)
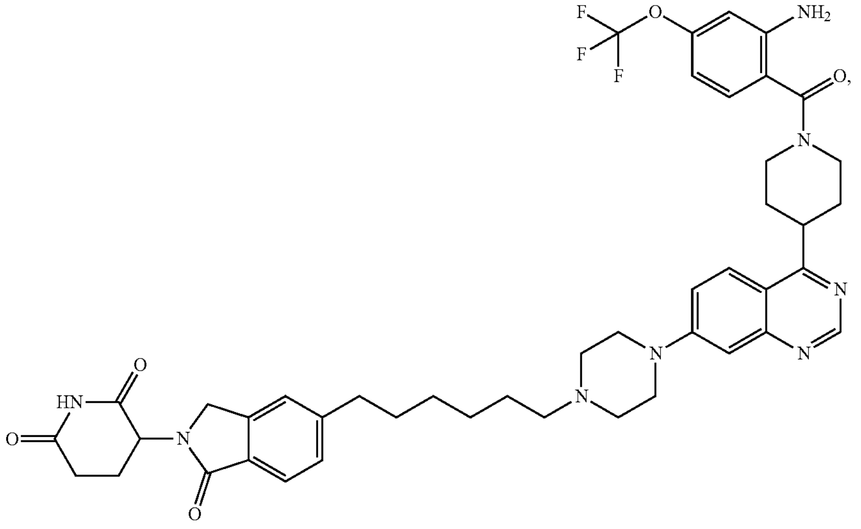
or
(12)
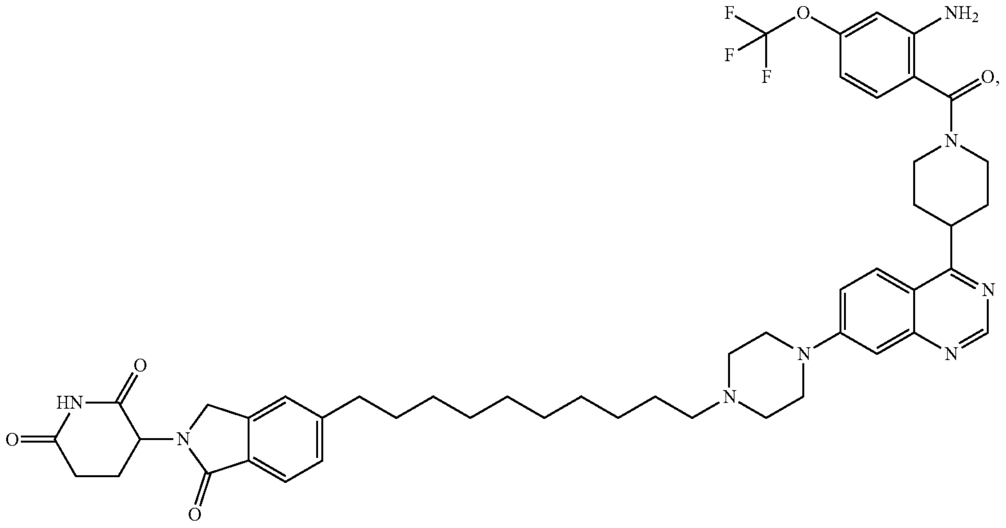
or a pharmaceutically acceptable salt or stereoisomer thereof.

19. A pharmaceutical composition, comprising a therapeutically effective amount of the compound of claim 1, or a pharmaceutically acceptable salt or stereoisomer thereof, and a pharmaceutically acceptable carrier.

20. A method of treating a disease or disorder that is characterized by aberrant ERK5 activity, comprising administering to a subject in need thereof a therapeutically effective amount of the compound or pharmaceutically acceptable salt or stereoisomer thereof of claim 1.

21. The method of claim 20, wherein the disease or disorder is cancer or an inflammatory disease.

22. The method of claim 21, wherein the cancer is leukemia, breast cancer, multiple myeloma, colon cancer, renal cancer, mesothelioma, pancreatic cancer, liver cancer, melanoma, or lung cancer, or wherein the inflammatory disease is rheumatoid arthritis, coeliac disease scleroderma, Sjögren's syndrome, lupus, vasculitis, myositis, gout, ankylosing spondylitis, or inflammatory bowel disease.

23. The method of claim 20, further comprising co-administering a therapeutically effective amount of an immunotherapy and/or chemotherapy.

24. The method of claim 23, wherein the immunotherapy is a checkpoint inhibitor, a cell-cycle inhibitor, or a targeted therapy.

25. The method of claim 24, wherein the checkpoint inhibitor is anti-PD-1 or anti-PD-L1, or wherein the cell-cycle inhibitor is palbociclib, ribociclib, or abemaciclib, or wherein the targeted therapy is a kinase inhibitor.

26. A method of reducing the levels of ERK5 in a cell, either in vitro or in vivo, comprising contacting the cell with an effective amount of the compound or pharmaceutically acceptable salt or stereoisomer thereof of claim 1.

* * * * *